(12) United States Patent
Okamoto et al.

(10) Patent No.: US 6,225,023 B1
(45) Date of Patent: May 1, 2001

(54) SULFONAMIDE COMPOUND AND METHOD FOR ITS PRODUCTION, METAL CHELATE COMPOUND EMPLOYING THE SULFONAMIDE COMPOUND, AND OPTICAL RECORDING MEDIUM EMPLOYING THE METAL CHELATE COMPOUND

(75) Inventors: Yuko Okamoto; Yutaka Kurose; Shuichi Maeda; Yuki Suzuki, all of Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/168,435

(22) Filed: Oct. 7, 1998

Related U.S. Application Data

(63) Continuation-in-part of application No. 08/974,506, filed on Nov. 19, 1997, now abandoned.

(30) Foreign Application Priority Data

| Nov. 20, 1996 | (JP) | 8-309178 |
| Dec. 11, 1996 | (JP) | 8-330864 |
| Mar. 6, 1997 | (JP) | 9-51986 |
| Jun. 9, 1997 | (JP) | 9-150700 |

(51) Int. Cl.[7] ........................................ G11B 7/24
(52) U.S. Cl. .................. 430/270.16; 430/945; 534/592; 534/707; 534/723
(58) Field of Search .................. 430/223, 226, 430/562, 945, 270.16; 8/471, 670, 686, 691, 696, 692; 534/592, 702, 707, 629, 641, 723

(56) References Cited

U.S. PATENT DOCUMENTS

| 3,468,871 | * | 9/1969 | Leverenz et al. | 8/692 |
| 3,980,427 | * | 9/1976 | Neeff | 8/692 |
| 4,341,700 | * | 7/1982 | Matzinger | 8/692 |
| 4,406,661 | * | 9/1983 | Buhler et al. | 8/691 |
| 5,233,028 | * | 8/1993 | Ohsuka et al. | 430/562 |
| 5,389,419 | * | 2/1995 | Maeda et al. | 430/270.19 |
| 5,441,299 | * | 8/1995 | Raue et al. | 534/579 |
| 5,446,136 | * | 8/1995 | Pape et al. | 534/592 |

FOREIGN PATENT DOCUMENTS

| 0053040 | * | 6/1982 | (EP) | 430/223 |
| 0717403 | * | 6/1996 | (EP) | 430/270.16 |
| 62-006987 | * | 1/1987 | (JP) | 8/691 |
| 9-198714 | * | 7/1997 | (JP) | 430/270.16 |

* cited by examiner

*Primary Examiner*—Martin Angebranndt
(74) *Attorney, Agent, or Firm*—Oblon, Spivak, McClelland, Maier & Neustadt, P.C.

(57) ABSTRACT

A sulfonamide compound of the formula (1):

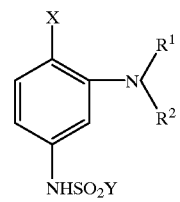

(1)

wherein X is a hydrogen atom, an alkyl or alkoxy group which may be substituted, or a halogen atom, Y Is an alkyl group having at least two fluorine atoms, and each of $R^1$ and $R^2$ which are independent of each other, is an alkyl group which may be substituted, or R1 may be bonded to X or $R^2$ to form a ring.

17 Claims, 22 Drawing Sheets

SULFONAMIDE COMPOUND AND METHOD FOR ITS PRODUCTION, METAL CHELATE COMPOUND EMPLOYING THE SULFONAMIDE COMPOUND, AND OPTICAL RECORDING MEDIUM EMPLOYING THE METAL CHELATE COMPOUND

This application is a continuation in part of U.S. patent application Ser. No. 08/974,506 filed Nov. 19, 1997, now abandoned, and incorporated entirely herein by reference.

The present invention relates to a novel sulfonamide compound and a method for its production, a metal chelate compound employing the sulfonamide compound, and an optical recording medium employing the metal chelate compound. The sulfonamide compound of the present invention is useful in the field of colorants, e.g. as a colorant for plastics, a dye for fibers, a dye for optical filters, a dye for printing inks or a dye for heat transfer printing, and it is further useful as a metal ion indicator.

Various type of optical discs have been proposed. Among them, there is one containing an organic dye in the recording layer. As the inorganic dye, various types have been studied, but none of them has been fully satisfactory.

It is an object of the present invention to provide an intermediate useful for the synthesis of an azo dye suitable for an optical disc, particularly an optical disc having a metal reflective layer and designed to use a semiconductor laser of a short wavelength.

In recent years, development of semiconductor lasers having short wavelengths has been progressed, and an optical recording medium capable of recording and retrieving information in a high density by means of a laser beam having a shorter wavelength than conventional 780 nm or 830 nm, has been desired. Optical recording media heretofore proposed include a magneto-optical recording medium, a phase-change recording medium, a chalcogen oxide optical recording medium, and an organic dye type optical recording medium. Among them, the organic dye type optical recording medium is considered to have a significance in that it is inexpensive and can be readily prepared. Further, the organic dye type optical recording medium includes a recordable compact disc (CD-R) which is widely known as a type wherein a metal layer having high reflectance is laminated on an organic dye layer.

With an organic dye type optical recording medium for recording by means of a semiconductor laser having a short wavelength, high density recording can be carried out by reducing the diameter of the laser beam by employing a laser having a wavelength shorter than the wavelength of the laser for CD-R. However, discs currently used for CD-R have a problem that when a laser having a wavelength of e.g. 680 nm, 650 nm or 635 nm, is used, the reflectance tends to be so low that record retrieving can hardly be carried out. The recording media currently proposed have problems such that deformation of the recording layer due to decomposition of the dye during recording, is substantial, no adequate degree of modulation can be obtained, and the light resistance or durability is inadequate.

The present inventors have previously proposed in JP-A-3-268994 an optical recording medium employing a metal chelate compound comprising a novel azo compound and a metal, which is excellent in light resistance and durability. However, as an optical recording medium having a metal reflective layer, the recording and retrieving properties by means of a semiconductor laser having a short wavelength, have been inadequate.

Further, in Japanese Patent Application No. 8-187794, the present inventors have proposed an optical recording medium employing a metal chelate compound comprising an azo type compound and a metal, which is capable of recording and retrieving information by means of a semiconductor laser having a short wavelength. However, the recording medium employing a metal chelate compound of the present invention, is one whereby the recording and retrieving characteristics and the light resistance and durability have been further improved.

It is an object of the present invention to provide a metal chelate compound made of an azo compound and a metal, which is useful for an optical recording medium which solves the above problems, and an optical recording medium prepared by employing such a metal chelate compound, which is excellent in information recording and retrieving characteristics by means of a semiconductor laser having a short wavelength and which has good light resistance and durability.

The intermediate of the present invention is a sulfonamide compound of the formula (1):

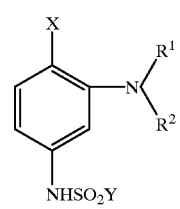

(1)

wherein X is a hydrogen atom, an alkyl or alkoxy group which may be substituted, or a halogen atom, Y is an alkyl group having at least two fluorine atoms, and each of $R^1$ and $R^2$ which are independent of each other, is an alkyl group which may be substituted, or $R^1$ may be bonded to X or $R^2$ to form a ring.

Preferably, X is a hydrogen atom, a methyl group, an ethyl group, a methoxy group, an ethoxy group or a methoxyethoxy group, Y is a $C_{1-3}$ alkyl group having at least two fluorine atoms, particularly a trifluoromethyl group or a 2,2,2-trifluoroethyl group, each of $R^1$ and $R^2$ which are independent each other, is a $C_{1-6}$ alkyl group which may have a substituent. The substituent may, for example, be a $C_{1-6}$ alkoxy group, a phenyl group, a cyclohexyl group or a vinyl group. Further, when $R^1$ is bonded to X or $R^2$ to form a ring, the ring is preferably a six-membered ring which may contain an oxygen atom or the like, and a $C_{1-4}$ alkyl group such as a methyl group or an ethyl group, may be substituted on the ring.

Typical examples of the sulfonamide compound of the present invention will be given in the following Table 1.

TABLE 1

| No. 1 | ![structure with NHSO₂CF₃ and N(C₂H₅)₂] |
|---|---|

TABLE 1-continued

| No. | Structure |
|-----|-----------|
| No. 2 | 3-(NHSO₂CF₃)-C₆H₄-N(C₄H₉(n))₂ |
| No. 3 | 3-(NHSO₂CF₃)-C₆H₄-N(C₂H₄OCH₃)₂ |
| No. 4 | 3-(NHSO₂CF₃)-C₆H₄-N(C₂H₄OC₄H₉(n))₂ |
| No. 5 | 3-(NHSO₂CH₂CF₃)-C₆H₄-N(C₂H₅)₂ |
| No. 6 | 3-(NHSO₂CF₃)-C₆H₄-N(CH₂CH=CH₂)₂ |
| No. 7 | 3-(NHSO₂CF₃)-C₆H₄-(N-morpholino) |
| No. 8 | 2-OCH₃-5-(NHSO₂CF₃)-C₆H₃-N(C₂H₅)₂ |
| No. 9 | 1-C₄H₉(n)-7-(NHSO₂CF₃)-1,2,3,4-tetrahydroquinoline |
| No. 10 | 1-C₂H₅-2,2,4-trimethyl-7-(NHSO₂CF₃)-1,2,3,4-tetrahydroquinoline |
| No. 11 | 2-Cl-5-(NHSO₂CF₃)-C₆H₃-N(C₂H₅)₂ |
| No. 12 | 2-F-5-(NHSO₂CF₃)-C₆H₃-N(C₂H₅)₂ |
| No. 13 | 3-(NHSO₂CF₃)-C₆H₄-N(C₂H₅)(CH₂C₆H₅) |
| No. 14 | 2-CH₃-5-(NHSO₂CF₃)-C₆H₃-N(C₂H₅)₂ |
| No. 15 | 2-C₂H₅-5-(NHSO₂CF₃)-C₆H₃-N(C₂H₅)₂ |
| No. 16 | 2-OC₂H₄OCH₃-5-(NHSO₂CF₃)-C₆H₃-N(C₂H₅)₂ |

The sulfonamide compound of the present invention can be produced by reacting an aniline of the following formula (2) with an alkyl sulfonyl halide or an alkyl sulfonic anhydride, which has at least two fluorine atoms in the alkyl group:

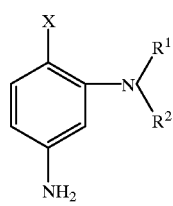

(2)

wherein X, $R^1$ and $R^2$ are as defined in the formula (1).

This reaction is carried out usually at a temperature of from −20 to +80° C. Preferably, the reaction is initiated at a-temperature of at most 20° C., more preferably at most 0° C., and the reaction is terminated at a temperature of from 20 to 30° C. This reaction is preferably conducted in a solvent. As the solvent, various types may be employed, such as benzene, toluene, xylene, n-hexane or methylene chloride. Preferred is methylene chloride or toluene.

When trifluoromethane sulfonic anhydride is used as the alkyl sulfonic anhydride, a trifluoromethane sulfonate of the sulfonamide compound can be obtained. The trifluoromethane sulfonate may be reacted with an alkali such as sodium acetate or sodium hydrogen carbonate in a suitable solvent such as methanol, ethanol or N,N-dimethylformamide, to obtain the desired free sulfonamide compound.

In the following step of diazotization coupling, the trifluoroethane sulfonate may be used as it is.

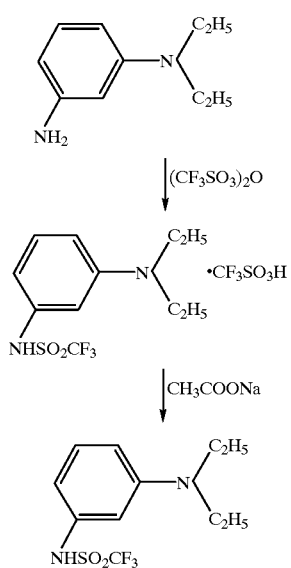

The compound of the formula (2) can be produced by various known methods. For example, a compound of the formula (2) wherein X is a hydrogen atom, and each of $R^1$ and $R^2$ is an alkyl group which may be substituted, can be readily produced by alkylating 3-aminoacetanilide which is commercially readily available, followed by hydrolysis. Further, a compound wherein X and $R^1$ together form a ring, such as a compound corresponding to No. 9 in Table 1, can be produced by alkylating tetrahydroquinoline by means of an alkylating agent such as n-butyl bromide, followed by nitration and reduction. A compound wherein $R^1$ and $R^2$ are bonded to form a ring, such as a compound corresponding to No. 7 in Table 1, can be produced by nitrating N-phenylmorpholine, followed by reduction.

The sulfonamide compound of the present invention can be used as the coupling component in preparation of an azo dye. The azo dye thereby obtainable, can be used for various applications such as for optical recording media, for liquid crystals, for heat transfer printing, for fibers or for coloring plastics. For example, a nickel-containing azo dye obtainable by the following reaction, is useful as a dye for absorbing a laser beam for an optical recording medium. In the formulae, D is a $C_{1-3}$ alkyl group.

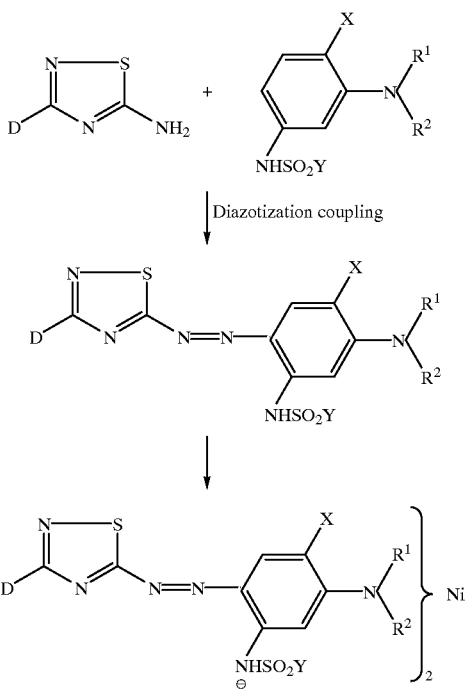

The present invention provides a metal chelate compound obtained from an azo compound of the following formula [a] or [b] and a metal salt, and an optical recording medium which contains such a metal chelate compound in its recording layer.

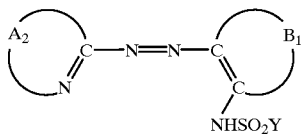

[a]

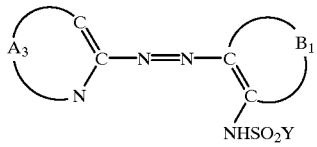

[b]

wherein each of $A_2$ and $A_3$ is a residue forming, together with the carbon atom and the nitrogen atom to which $A_2$ or $A_3$ is bonded, a heterocyclic ring which may be substituted, $B_1$ is a residue forming, together with the carbon atoms to which $B_1$ is bonded, an aromatic or heterocyclic ring which may be substituted, and Y is a $C_{1-6}$ linear or branched alkyl group substituted by at least two fluorine atoms.

Preferably, the present invention provides a metal chelate compound obtained from an azo compound of the following formula [c] or [d] and a metal salt, and an optical recording medium which contains such a metal chelate compound in its recording layer.

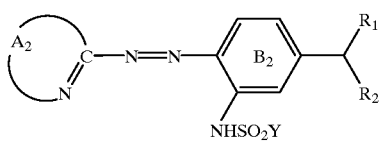

[c]

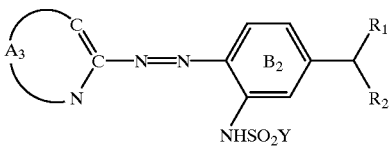

[d]

wherein each of $A_2$ and $A_3$ is a residue forming, together with the carbon atom and the nitrogen atom to which $A_2$ or $A_3$ is bonded, a heterocyclic ring which may be substituted, $B_2$ is a benzene ring which may have a substituent in addition to $-NR_1R_2$ and $-NHSO_2Y$ groups, Y is a $C_{1-6}$ linear or branched alkyl group substituted by at least two fluorine atoms, and each of $R_1$ and $R_2$ which are independent of each other, is an alkyl group which may be substituted, or $R_1$ and $R_2$ together form a ring.

More preferably, the present invention provides a metal chelate compound obtained from an azo compound of the following formula (I) and a metal salt, and an optical recording medium which contains such a metal chelate compound in its recording layer.

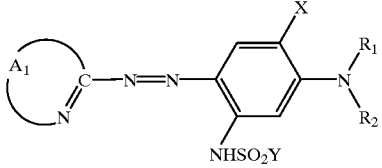

[I]

wherein $A_1$ is a residue forming, together with the carbon atom and the nitrogen atom to which $A_1$ is bonded, a heterocyclic ring selected from the group consisting of thiadiazole, isoxazole, imidazole, pyrazole, thiazole, triazole and pyridine, X is a hydrogen atom, an alkyl group, an alkoxy group or a halogen atom, Y is a $C_{1-6}$ linear or branched alkyl group substituted by at least two fluorine atoms, and each of $R_1$ and $R_2$ which are independent of each other, is an alkyl group which may be substituted, or $R_1$ and $R_2$ together form a ring.

Now, the present invention will be described in detail.

In the above formulae [a], [b], [c], [d] and [I] for the azo compound of the present invention, Y is preferably $C_{1-6}$ linear or branched alkyl group having at least two fluorine atoms, specifically, it may, for example, be a $C_{1-6}$ perfluoroalkyl group such as a trifluoromethyl group, a pentafluoroethyl group or a heptafluoropropyl group, or an alkyl group substituted by a perfluoroalkyl group having a total number of carbon atoms of from 2 to 6, such as a 2,2,2-trifluoroethyl group, a 3,3,3-trifluoropropyl group or a 2,2,3,3,3-pentafluoropropyl group. Particularly preferred is $-CH_2CF_3$ or $-CF_3$ from the viewpoint of the absorption spectrum, as well as light resistance and durability.

In the formulae [a], [b], [c] and [d], examples of the structure includes the following groups:

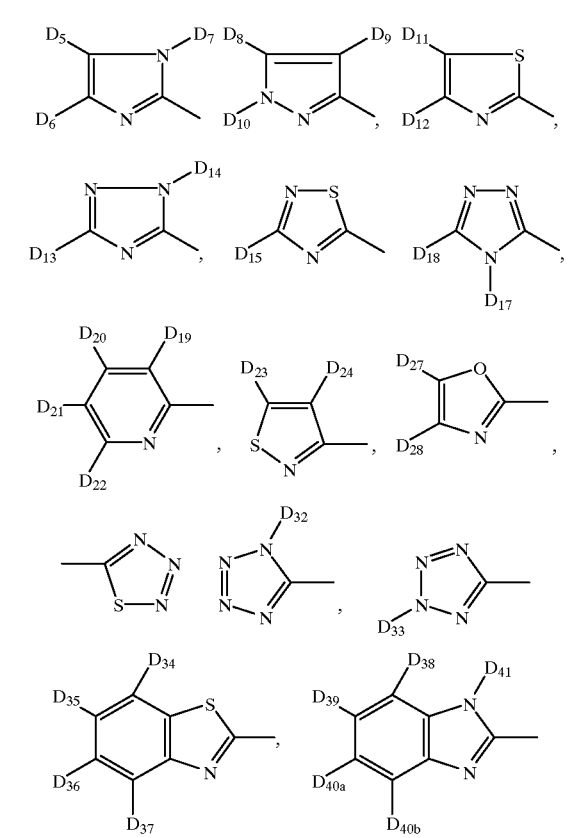

Also, examples of the structure

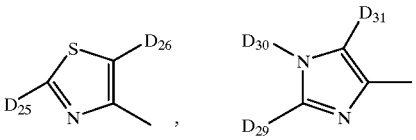

include:

In the above formulae, each of $D_1$ to $D_{41}$ is a hydrogen atom, a $C_{1-6}$ linear or branched alkyl group such as a methyl group, an ethyl group, a n-propyl group, an isopropyl group, a n-butyl group, a sec-butyl group, a tert-butyl group, a n-pentyl group or a n-hexyl group; a $C_{3-6}$ cycloalkyl group such as a cyploroyl group, a cyclobutyl group, a cyclopentyl group or a cyclohexyl group; a $C_{1-6}$ alkoxy group such as a methoxy group, an ethoxy group, a n-propoxy group, an isopropoxy group, a n-butoxy group, a tert-butoxy group, a sec-butoxy group, a n-pentyloxy group or a n-hexyloxy group; a $C_{1-6}$ alkyl carbonyl group such as an acetyl group, a propionyl group, a butyryl group, an isobutyryl group, a valeryl group, an isovaleryl group, a pivaloyl group, a hexanoyl group or a heptanoyl group; a $C_{2-6}$ linear or branched alkenyl group such as a vinyl group, a propenyl group, a butenyl group, a pentenyl group or a hexenyl group; a $C_{3-6}$ cycloalkenyl group such as a cyclopentenyl group or a cyclohexenyl group; a halogen atom such as a fluorine atom, a chlorine atom or a bromine atom; a formyl group; a hydroxyl group; a carboxyl group; a $C_{1-6}$ hydroxyalkyl group such as a hydroxymethyl group or a hydroxyethyl group; a $C_{2-7}$ alkoxycarbonyl group such as a methoxycarbonyl group, an ethoxycarbonyl group, a n-propoxycarbonyl group, an isopropoxycarbonyl group, a n-butoxycarbonyl group, a tert-butoxycarbonyl group, a sec-butoxycarbonyl group, a n-pentyloxycarbonyl group or a n-hexyloxycarbonyl group; a nitro group; a cyano group; a cyano group; an amino group; a $C_{1-10}$ alkylamino group such as a methylamino group, an ethylamino group, a n-propylamino group, a n-butylamino group, a dimethylamino group, a diethylamino group, a di-n-propylamino group or a di-n-butylamino group; a $C_{3-7}$ alkoxycarbonylalkyl group such as a methoxycarbonylmethyl group, an ethoxycarbonylmethyl group, a n-propoxycarbonylmethyl group or an isopropoxycarbonylethyl group; a $C_{1-6}$ alkylthio group such as a methylthio group, an ethylthio group, a n-propylthio group, a tert-butylthio group, a sec-butylthio group, a n-pentylthio group or a n-hexylthio group; a $C_{1-6}$ alkylsulfonyl group such as a methylsulfonyl group, an ethylsulfonyl group, a n-propylsulfonyl group, an isopropylsulfonyl group, a n-butylsulfonyl group, a tert-butylsulfonyl group, a sec-butylsulfonyl group, a n-pentylsulfonyl group or a n-hexylsulfonyl group; a $C_{6-16}$ aryl group which may have a substituent; a $C_{7-17}$ arylcarbonyl group which may have a substituent; —$CD_{42}$=C(CN)$D_{43}$, (wherein $D_{42}$ is a hydrogen atom, or a C1-6 alkyl group such as a methyl group, an ethyl group, a n-propyl group, an isopropyl group, a n-butyl group, a sec-butyl group, a tert-butyl group, a n-pentyl group or a n-hexyl group, and $D_{43}$ is a cyano group, or a $C_{2-7}$ alkoxycarbonyl group such as a methoxycarbonyl group, an ethoxycarbonyl group, a n-propoxylcarbonyl group, an isopropoxycarbonyl group, a n-butoxycarbonyl group, a tert-butoxycarbonyl group, a sec-butoxycarbonyl group, a n-pentylcarbonyl group or a n-hexyloxycarbonyl group;

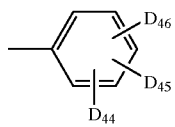

wherein each of $D_{44}$ to $D_{46}$ which are independent of one another, is a hydrogen atom, a nitro group, a halogen atom such as a fluorine atom, a chlorine atom or a bromine atom, a $C_{1-6}$ linear or branched alkyl group such as a methyl group, an ethyl group, a n-propyl group, an isopropyl group, a n-butyl group, a sec-butyl group, a tert-butyl group, a n-pentyl group or a n-hexyl group, a $C_{3-6}$ cycloalkyl group such as a cyclopropyl group, a cyclobutyl group, a cyclopentyl group or a cyclohexyl group, or a $C_{1-6}$ alkoxy group such as a methoxy group, an ethoxy group, a n-propoxy group, an isopropoxy group, a n-butoxy group, a tert-butoxy group, a sec-butoxy group, a n-pentyloxy group or a n-hexyloxy group;

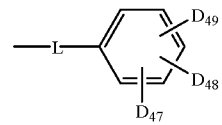

wherein each of $D_{47}$ to $D_{49}$ which are independent of one another, is a hydrogen atom, a nitro group, a halogen atom such as a fluorine atom, a chlorine atom or a bromine atom, a $C_{1-6}$ linear or branched alkyl group such as a methyl group, an ethyl group, a n-propyl group, an isopropyl group, a n-butyl group, a sec-butyl group, a tert-butyl group, a n-pentyl group or a n-hexyl group, a $C_{3-5}$ cycloalkyl group such as a cyclopropyl group, a cyclobutyl group, a cyclopentyl group or a cyclohexyl group, or a $C_{1-6}$ alkoxy group such as a methoxy group, an ethoxy group, a n-propoxy group, an isopropoxy group, a n-butoxy group, a tert-butoxy group, a sec-butoxy group, a n-pentyloxy group or a n-hexyloxy group, and L is $SCH_2$ or $SO_2$; a $C_{1-6}$ fluoroalkyl group such as a trifluoromethyl group, a pentafluoroethyl group, a heptafluoro-n-propyl group, a heptafluoroisopropyl group, a perfluoro-n-butyl group, a perfluoro-sec-butyl group, a perfluoro-n-pentyl group or a perfluoro-n-hexyl group; a $C_{1-6}$ fluoroalkoxy group such as a trifluoromethoxy group, a pentafluoroethoxy group, a trifluoroethoxyl group, a pentafluoroethoxy group, a perfluoro-n-butoxy group, a perfluoro-tert-butoxy group, a perfluoro-sec-butoxy group, a perfluoro-n-pentyloxy group or a perfluoro-n-hexyloxy group; or a $C_{1-6}$ fluoroalkylthio group such as a trifluoromethylthio group, a trifluoroethylthio group, a pentafluoroethylthio group, a heptafluoro-n-propylthio group, a heptafluoroisopropylthio group, a perfluoro-n-butylthio group, a perfluoro-t-butylthio group, a perfluoro-sec-butylthio group, a perfluoro-n-pentylthio group or a perfluoro-n-hexylthio group.

Preferable examples of a heterocyclic ring having $A_2$ or $A_3$ residues include thiadiazole, isoxazole, imidazole, pyrazole, thiazole, isothiazole, triazole, pyridine, benzothiazole and benzimidazole, all of which may be substituted.

Preferable examples of a structure having $B_1$ residue in the above formulae [a], [b], [c] and [d] include:

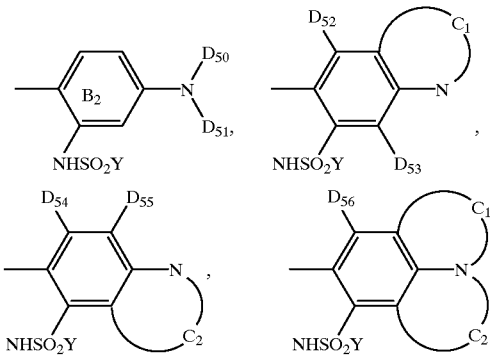

wherein $B_3$ is a benzene ring which may have a substituent in addition to —$ND_{50}D_{51}$ and —$NHSO_2Y$ groups, each $C_1$ and $C_2$ which are independent of each other, is a residue forming a heterocyclic ring which may be substituted, and each of $D_{50}$ to $D_{56}$ is a hydrogen atom or an arbitrary substituent.

Among the structures mentioned above, concrete examples of a structure having a $B_1$ residue include:
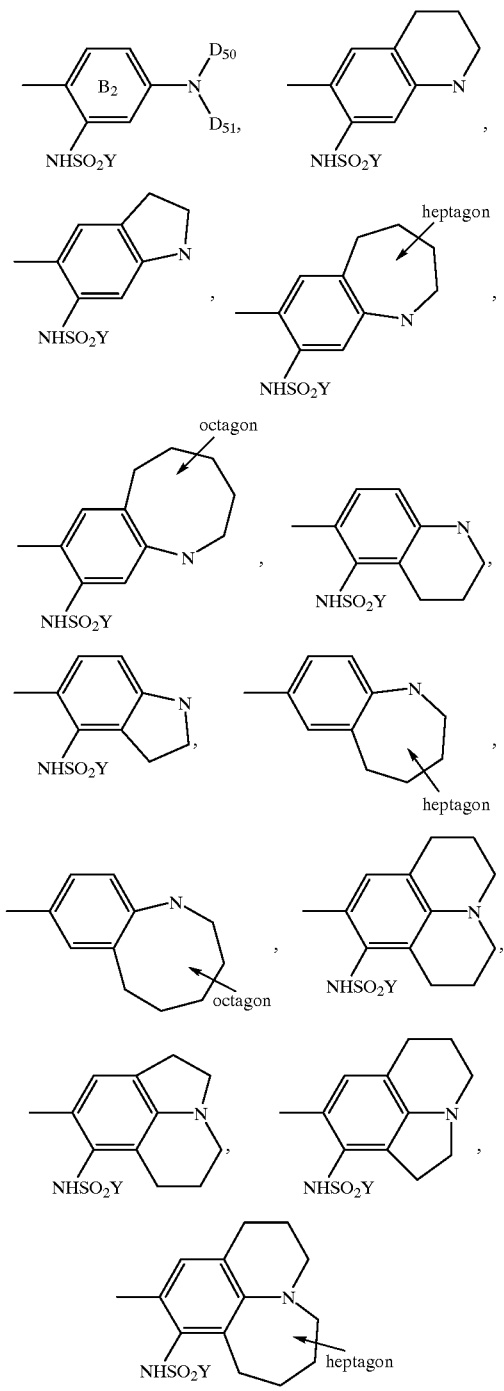
Each of the above formulae may have a substituent in addition to a —NHSO2Y group, and examples of the substituent include the above examples illustrated with regard to $D_1$ to $D_{41}$.
Examples of a dye of the formula [a] or [b] include the following compounds.
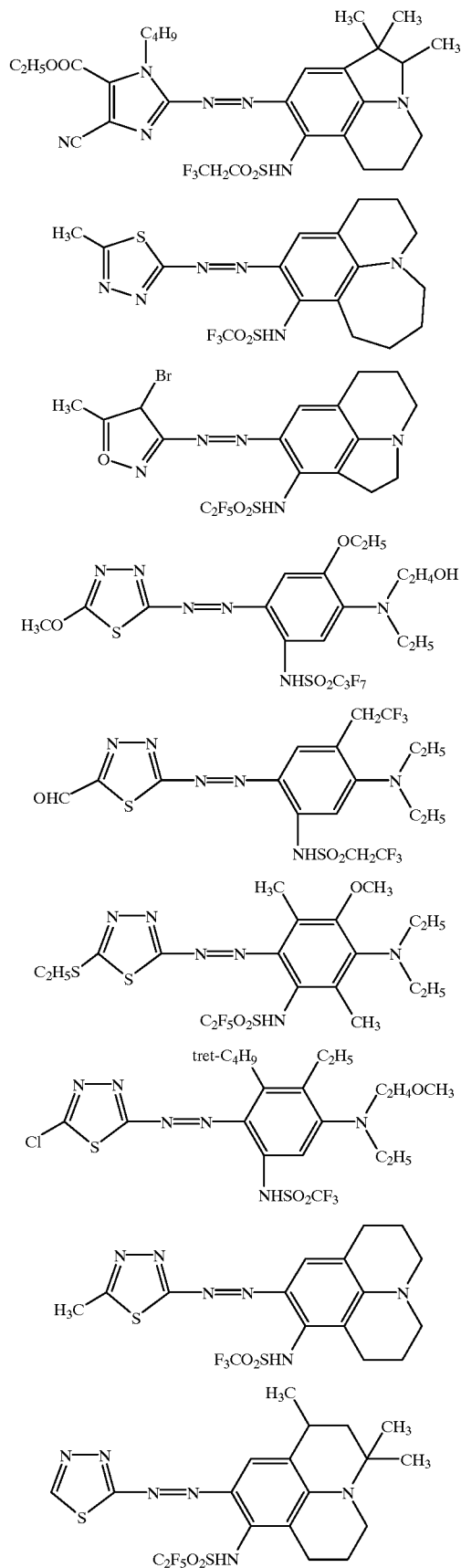

-continued
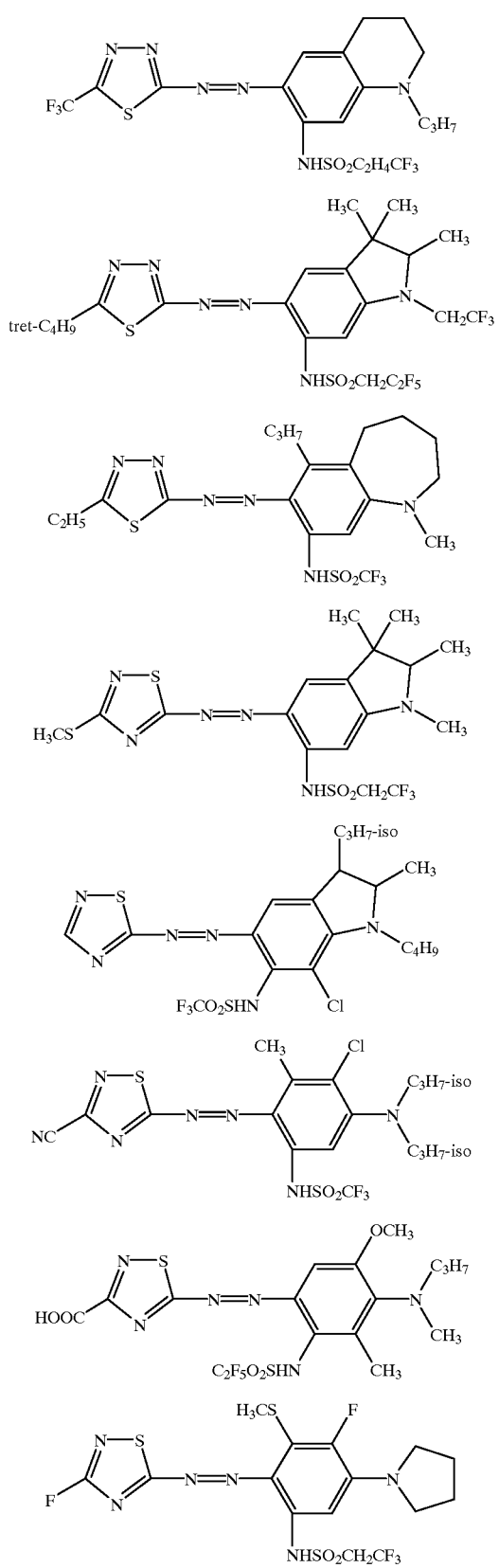
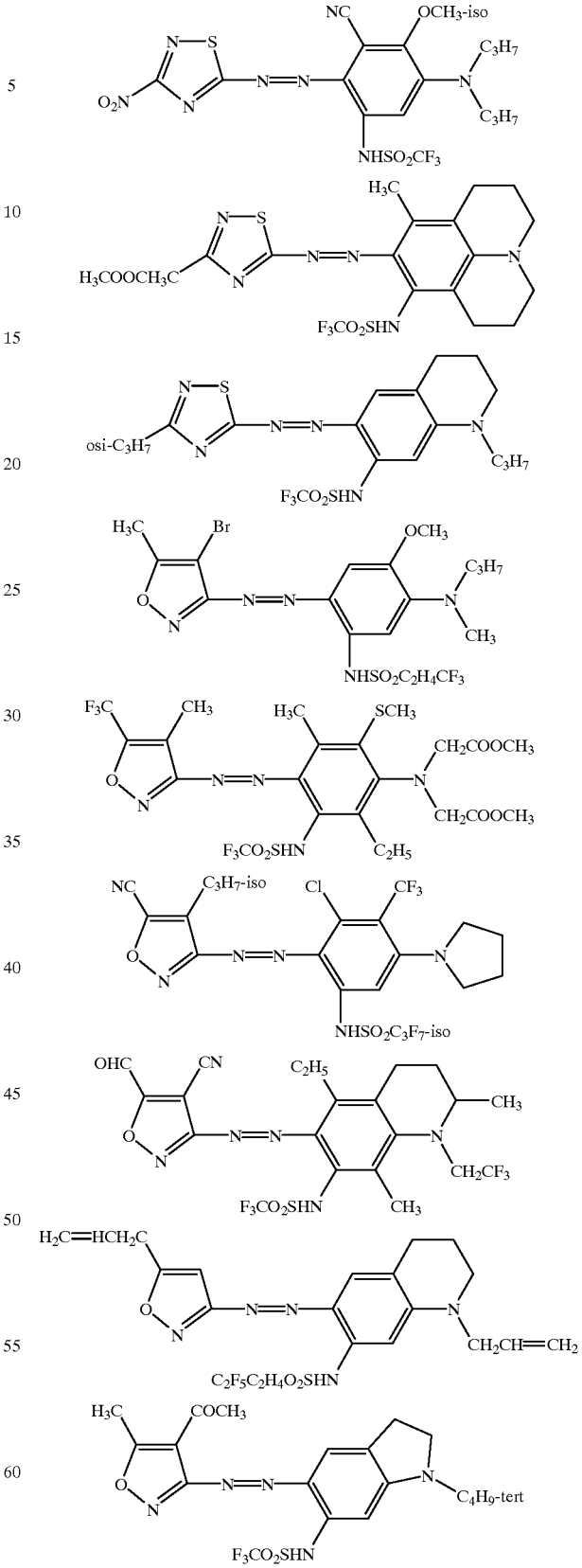

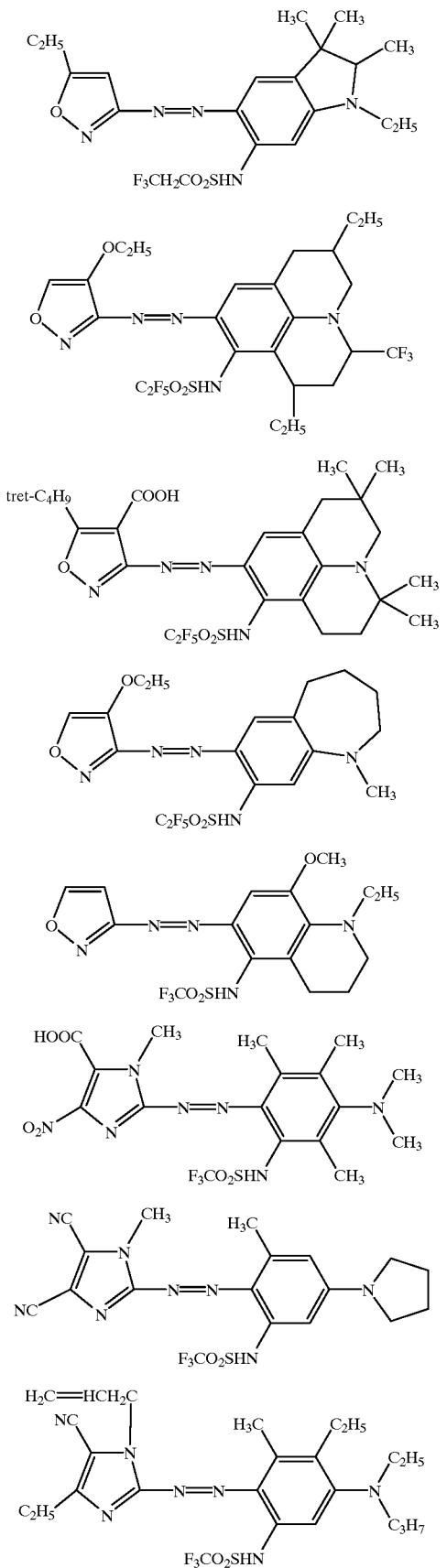
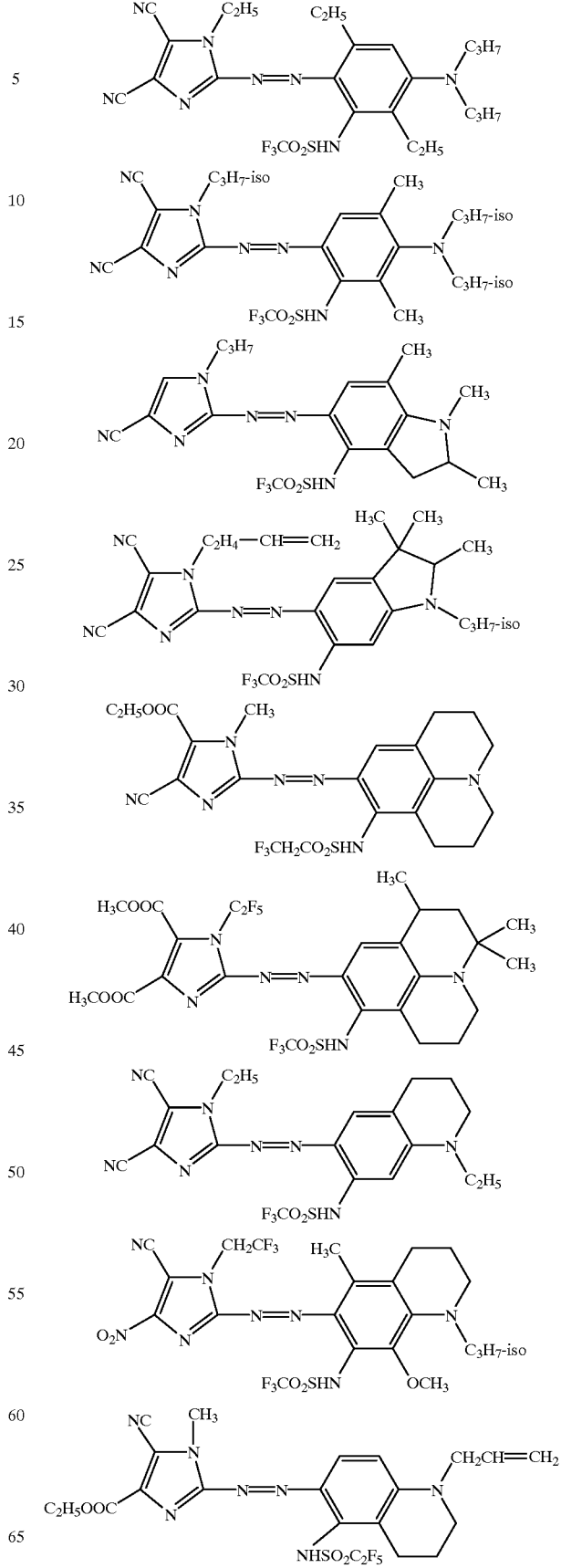

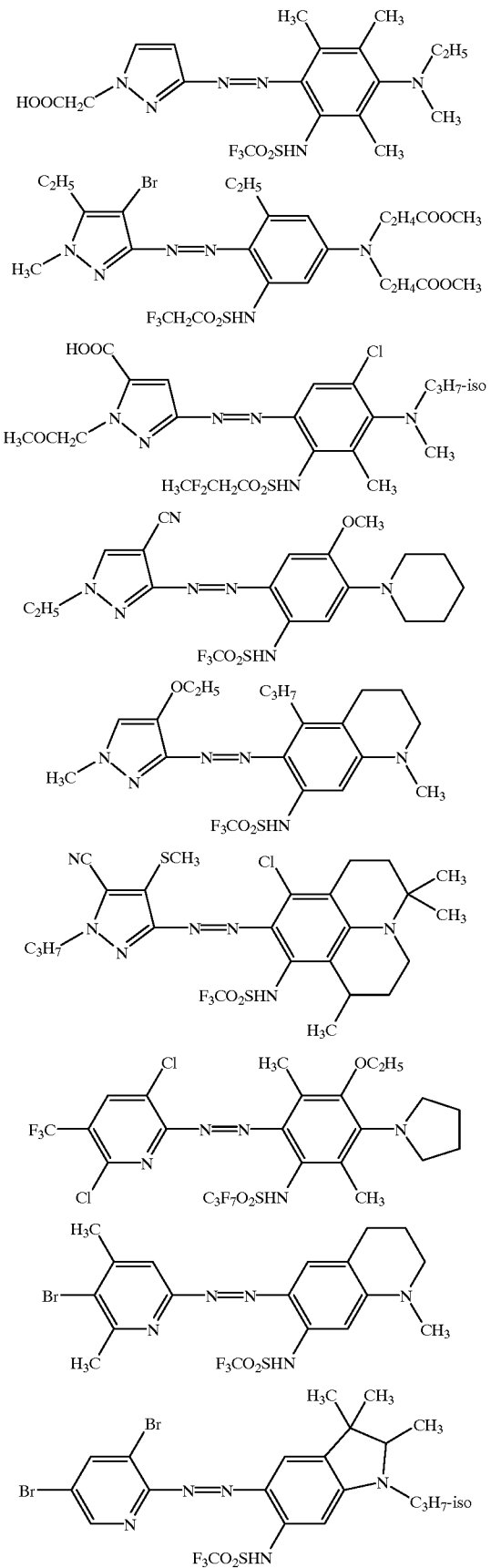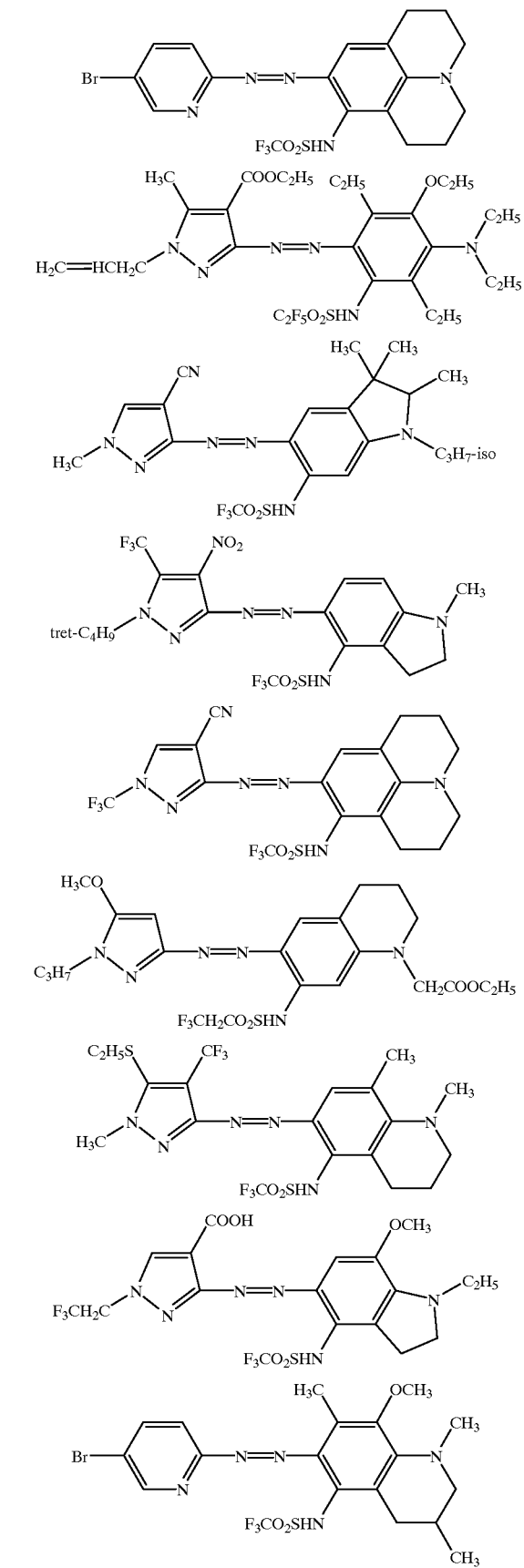

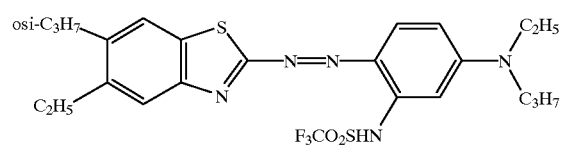
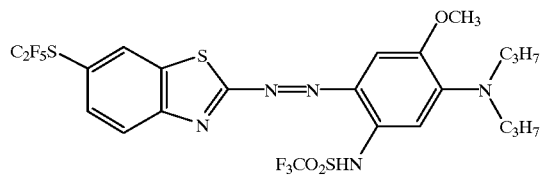
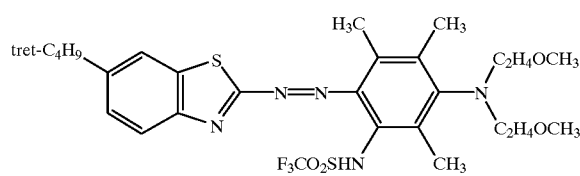
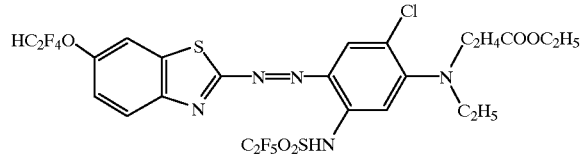
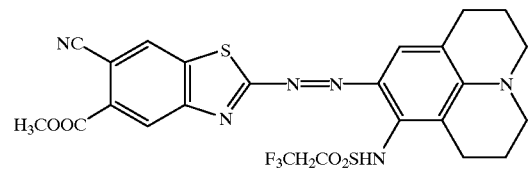
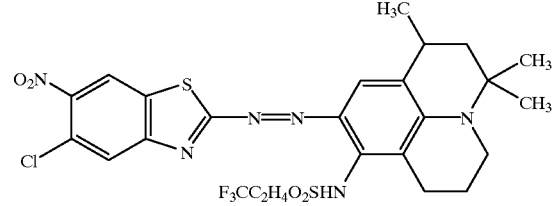
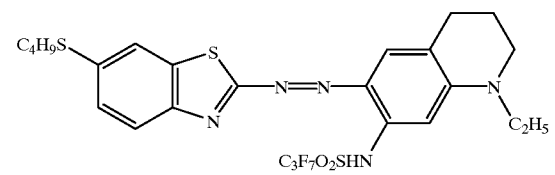
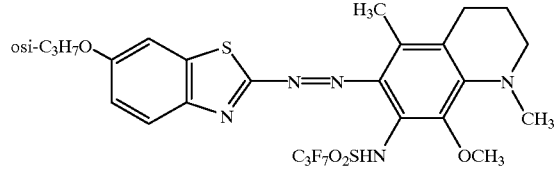
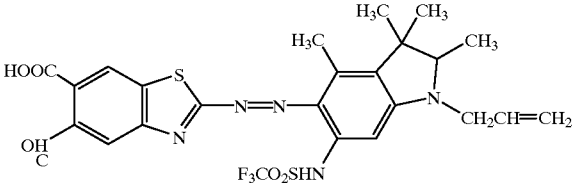
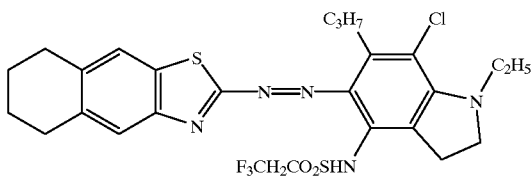
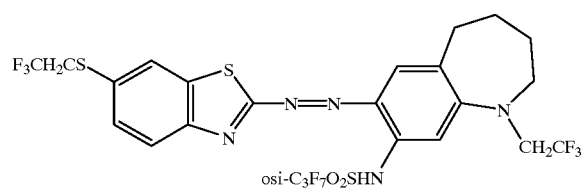
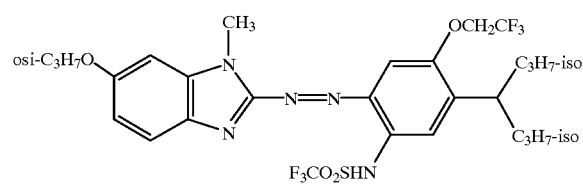
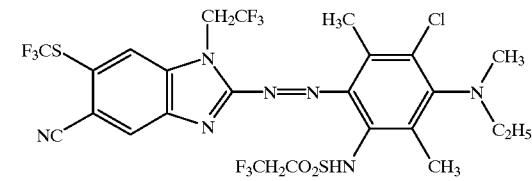
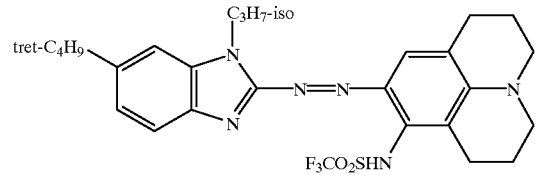
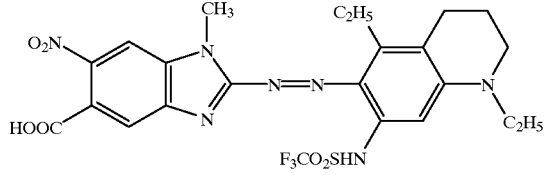
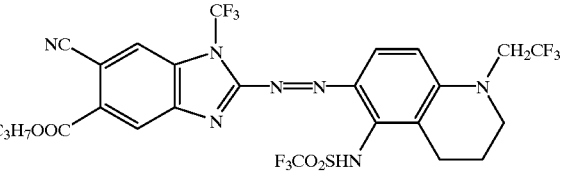
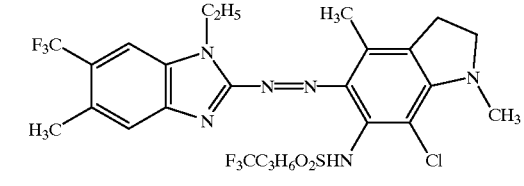

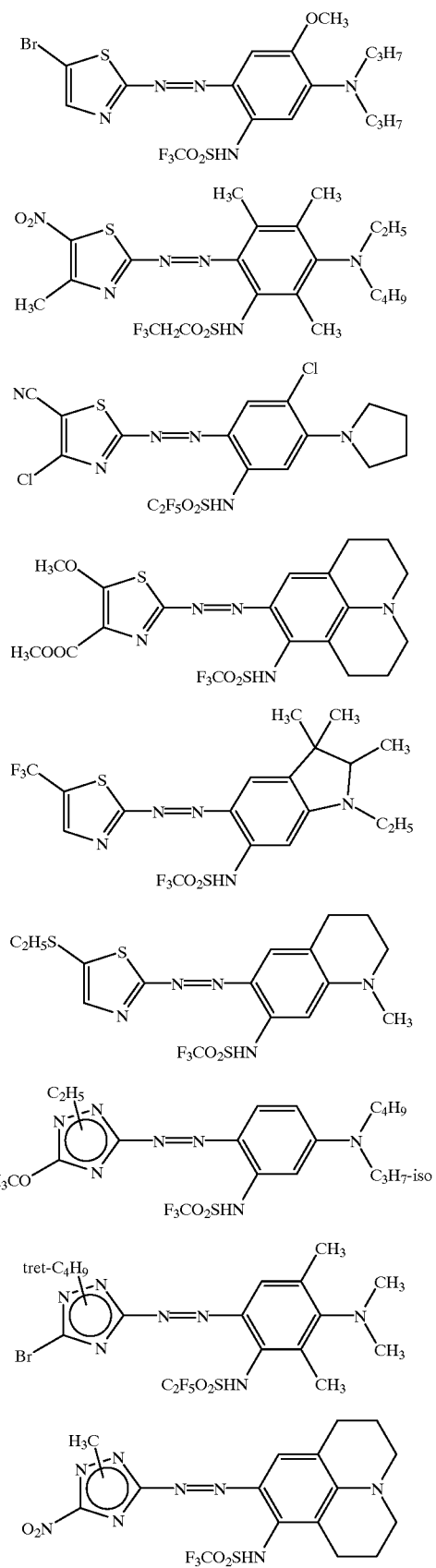
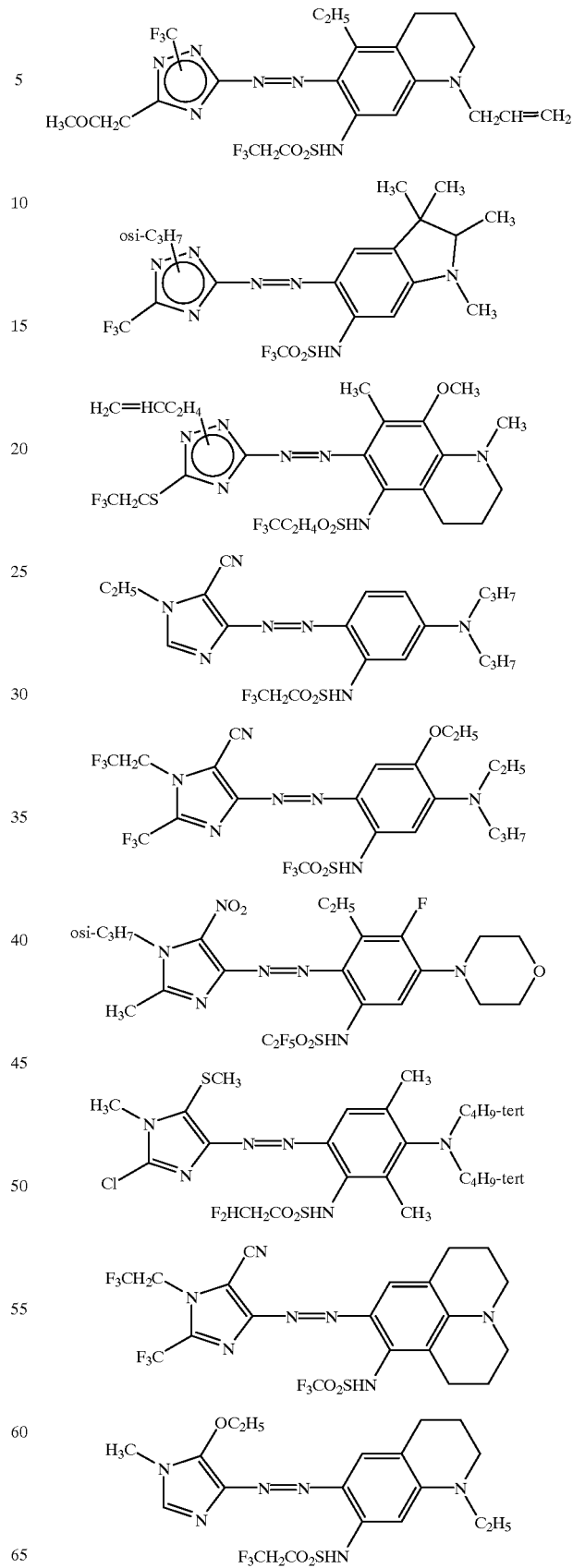

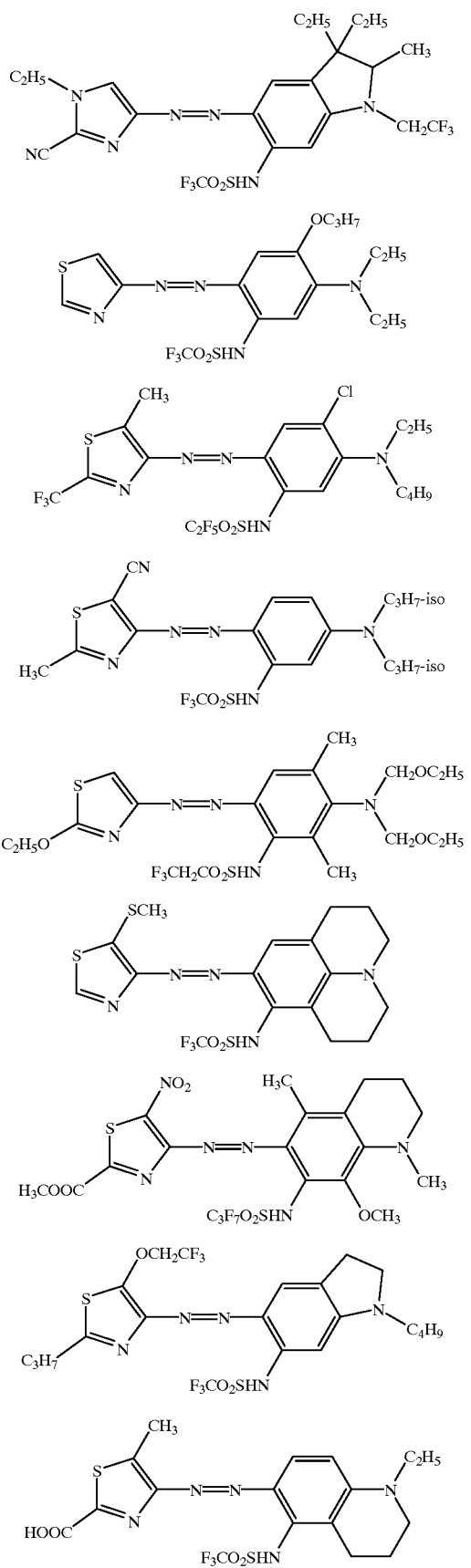
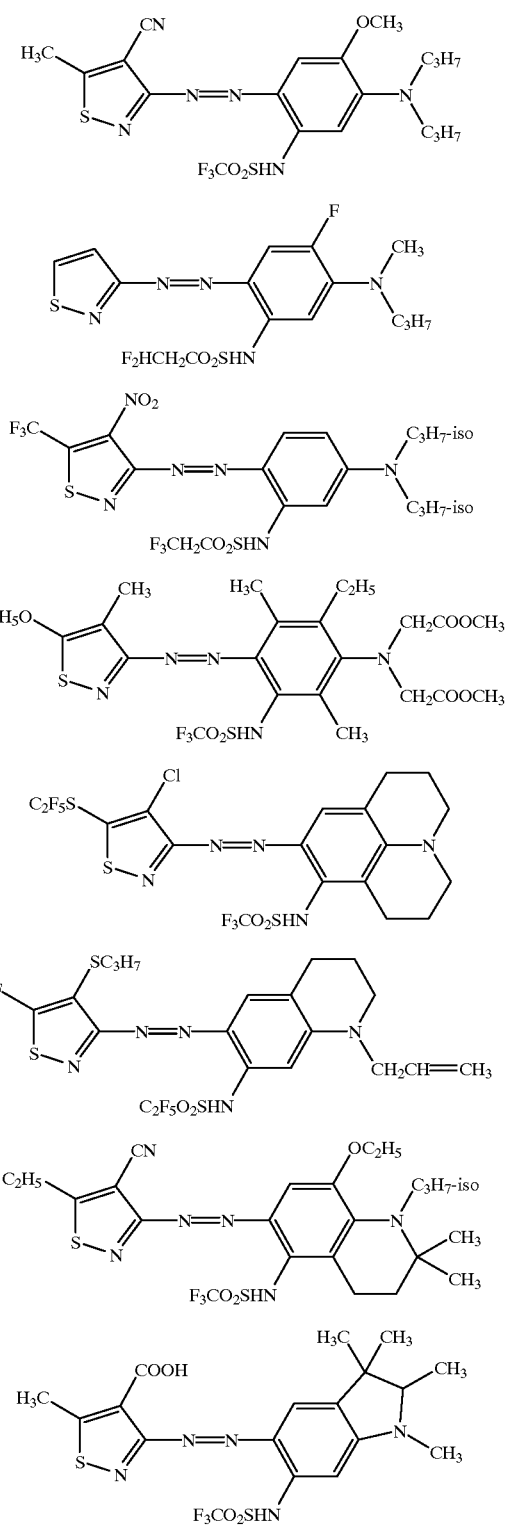
Among the above formulae, a particularly preferable structure having a B1 residue is shown below:

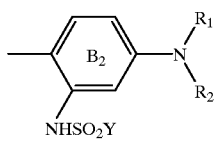

wherein each of $R_1$ and $R_2$ which are independent of each other, is a hydrogen atom; or a $C_{1-20}$ linear or branched alkyl group, such as a methyl group, an ethyl group, a n-propyl group, an isopropyl group, a n-butyl group, a tert-butyl group, a sec-butyl group, a n-pentyl group, a n-hexyl group, a n-heptyl group, a n-octyl group, a n-decyl group, a n-dodecyl group or a n-octadecyl group, preferably a $C_{1-10}$ linear or branched alkyl group, more preferably a $C_{1-6}$ linear or branched alkyl group. Such a $C_{1-20}$ linear or branched alkyl group may be substituted by e.g. a $C_{1-10}$ alkoxy group such as a methoxy group, an ethoxy group, a n-propoxy group, an isopropoxy group, a n-butoxy group, a tert-butoxy group, a sec-butoxy group, a n-pentyloxy group, a n-hexyloxy group, a n-heptyloxy group, a n-octyloxy group or a n-decyloxy group; a $C_{2-12}$ alkoxyalkoxy group such as a methoxymethoxy group, an ethoxymethoxy group, a propoxymethoxy group, a methoxyethoxy group, an ethoxyethoxy group, a propoxyethoxy group, a methoxypropoxy group, an ethoxypropoxy group, a methoxybutoxy group or an ethoxybutoxy group; a $C_{3-15}$ alkoxyalkoxyalkoxy group such as a methoxymethoxymethoxy group, a methoxymethoxyethoxy group, a methoxyethoxymethoxy group, a methoxyethoxyethoxy group, an ethoxymethoxymethoxy group, an ethoxymethoxyethoxy group, an ethoxyethoxymethoxy group or an ethoxyethoxyethoxy group; an allyloxy group; a $C_{6-12}$ aryl group such as a phenyl group, a tolyl group, a xylyl group or a naphthyl group; a $C_{6-12}$ aryloxy group such as a phenoxy group, a tolyloxy group, a xylyloxy group or a naphthyloxy group; a cyano group; a nitro group; a hydroxyl group; a tetrahydrofuryl group; a $C_{1-6}$ alkylsulfonylamino group such as a methylsulfonylamino group, an ethylsulfonylamino group, a n-propylsulfonylamino group, an isopropylsulfonylamino group, a n-butylsulfonylamino group, a tert-butylsulfonylamino group, a sec-butylsulfonylamino group, a n-pentylsulfonylamino group or a n-hexylsulfonylamino group; a halogen atom such as a fluorine atom, a chlorine atom or a bromine atom; a $C_{2-7}$ alkoxycarbonyl group such as a methoxycarbonyl group, an ethoxycarbonyl group, a n-propoxycarbonyl group, an isopropoxycarbonyl group, a n-butoxycarbonyl group, a tert-butoxycarbonyl group, a sec-butoxycarbonyl group, a n-pentyloxycarbonyl group or a n-hexyloxycarbonyl group; a $C_{2-7}$ alkylcarbonyloxy group such as a methylcarbonyloxy group, an ethylcarbonyloxy group, a n-propylcarbonyloxy group, an isopropylcarbonyloxy group, a n-butylcarbonyloxy group, a tert-butylcarbonyloxy group, a sec-butylcarbonyloxy group, a n-pentylcarbonyloxy group or a n-hexylcarbonyloxy group; or a $C_{2-7}$ alkoxycarbonyloxy group such as a methoxycarbonyloxy group, an ethoxycarbonyloxy group, a n-propoxycarbonyloxy group, an isopropoxycarbonyloxy group, a n-butoxycarbonyloxy group, a tert-butoxycarbonyloxy group, a sec-butoxycarbonyloxy group, a n-pentyloxycarbonyloxy group or a n-hexyloxycarbonyloxy group.

In the formula (1),

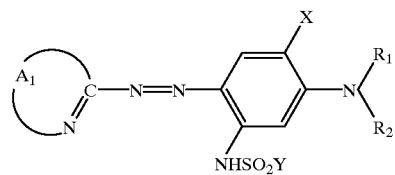

examples of heterocyclic ring having an $A_1$ residue include the following groups:

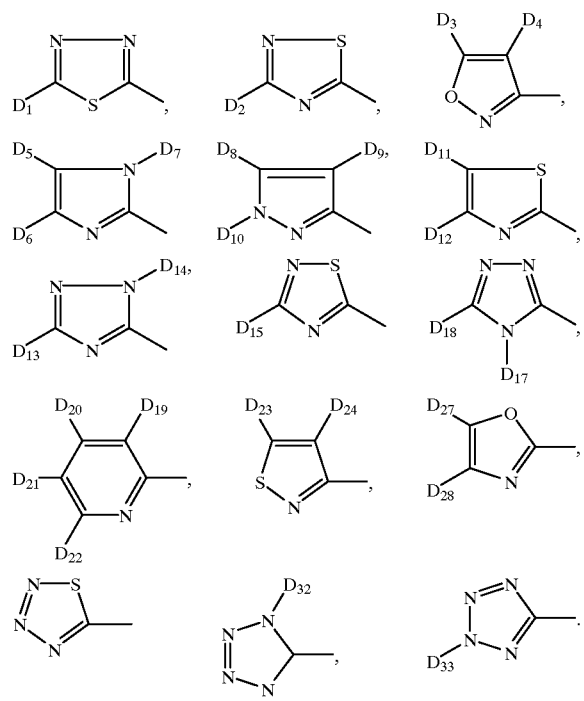

wherein each of $D_1$ to $D_{33}$ as defined above.

Among the above formulae, preferable examples of heterocyclic ring having an $A_1$ residue include thiazole, isoxazole, imidazole, pyrazole, thiadiazole, triazole and pyridine, all of which may be substituted. Also in the above-mentioned formula (I),

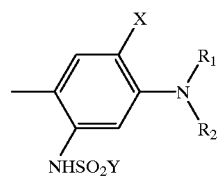

X may be a hydrogen atom, an alkyl group, an alkoxy group or a halogen atom, particularly preferably a hydrogen atom or a methoxy group.

Among the above mentioned azo compounds, those of the following formulae (II) to (X) are most preferred.

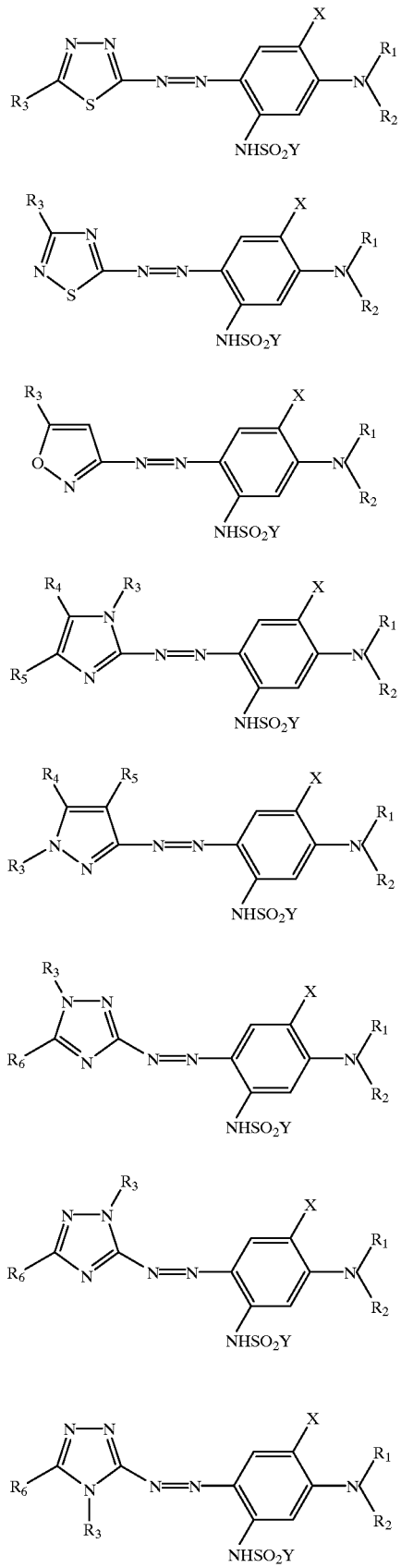

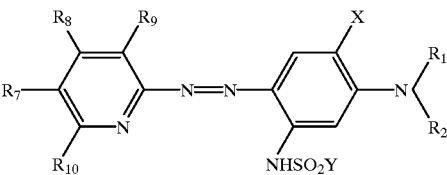

wherein, X is a hydrogen atom, atom methoxy group, an ethoxy group or a propoxy group, Y is a $C_{1-6}$ linear or branched alkyl group substituted by at least two fluorine atoms, each of $R_1$, $R_2$ and $R_3$ is a $C_{1-6}$ linear or branched alkyl group which may have a substituent, each of $R_4$ and $R_5$ is a $C_{1-6}$ linear or branched alkyl group which may have a substituent, a cyano group or a carboxylic acid ester group, $R_6$ is a $C_{1-6}$ linear or branched alkyl group which may have a substituent, an alkoxy group or an alkylthio group, and each of $R_7$ to $R_{10}$ is a $C_{1-6}$ linear or branched alkyl group which may have a substituent, a hydrogen atom or a halogen atom.

Referring to the formula (II), the following compounds may be mentioned as preferred examples of the metal chelate compound obtained from an azo compound and a metal salt.

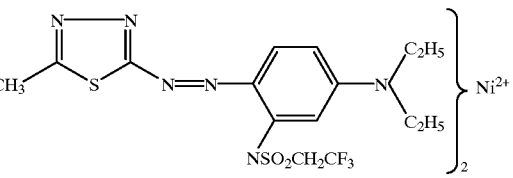

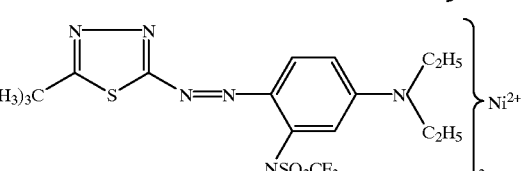

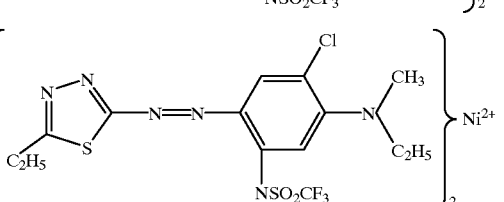

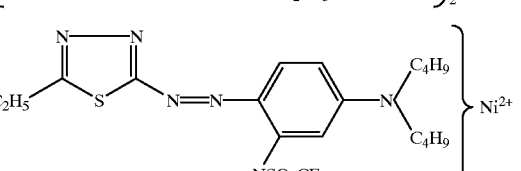

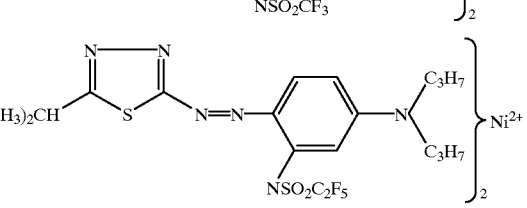

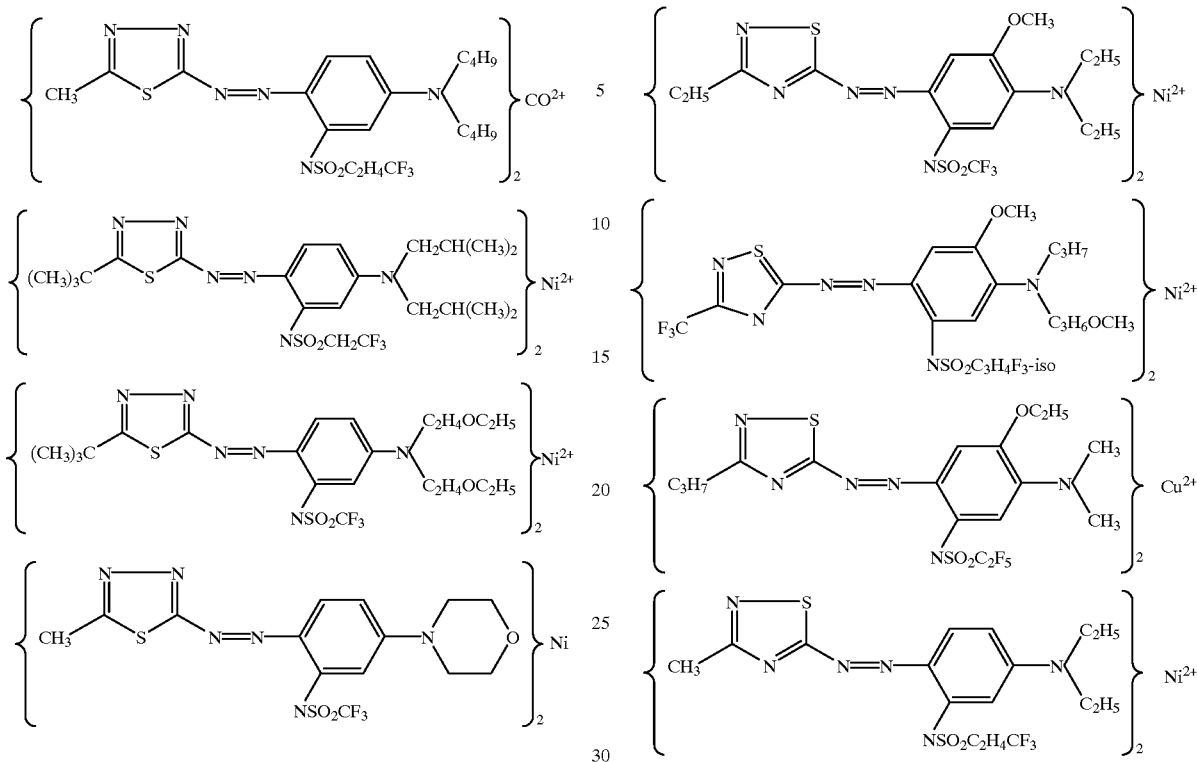
Referring to the formula (III), the following compounds may be mentioned as preferred examples of the metal chelate compound obtained by an azo compound and a metal salt.
Referring to the formula (IV), the following compounds may be mentioned as preferred examples of the metal chelate compound obtained from an azo compound and a metal salt.
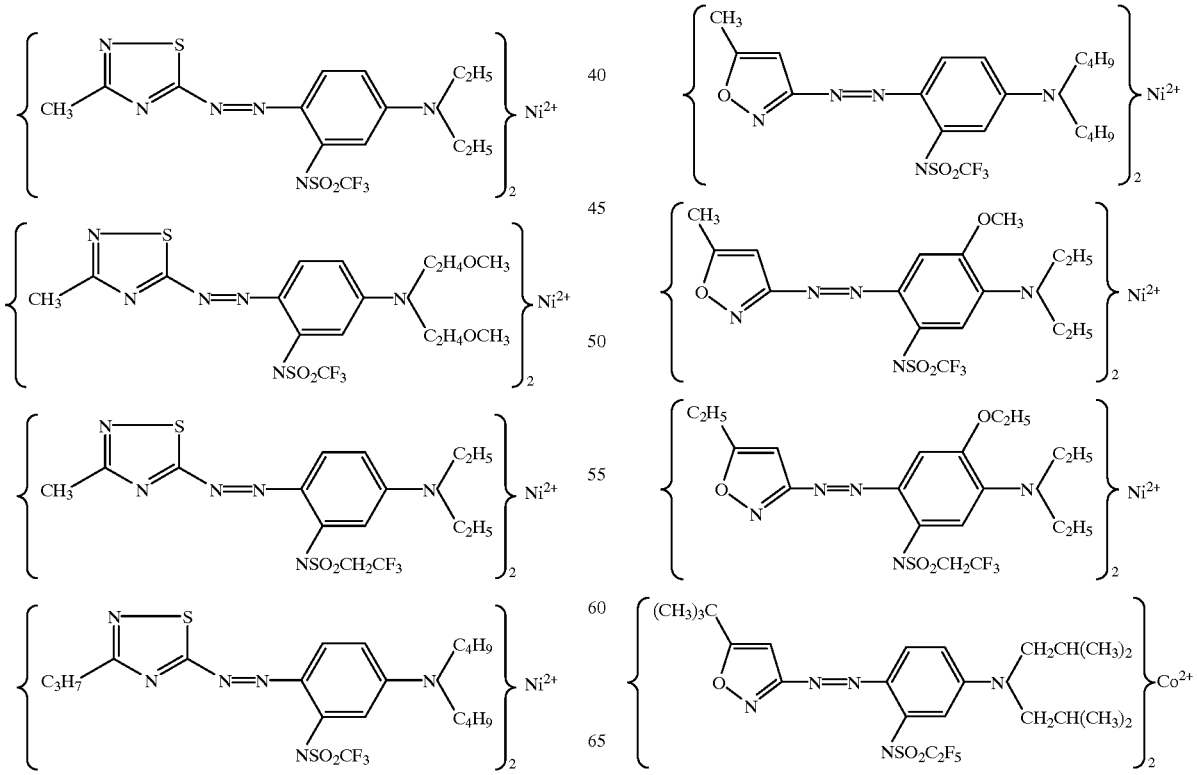

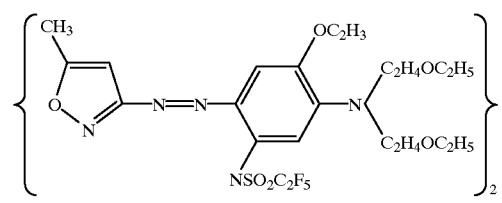
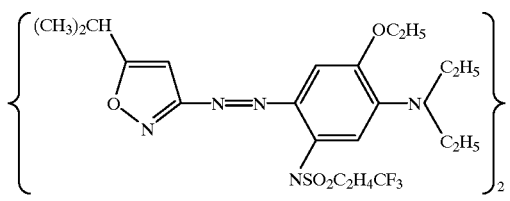
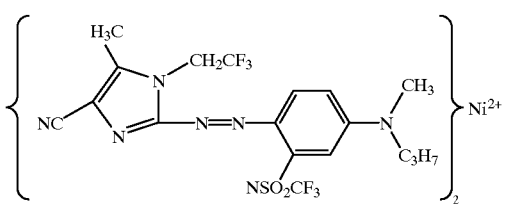
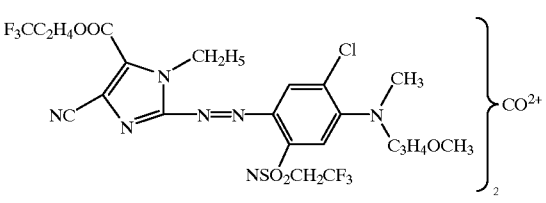
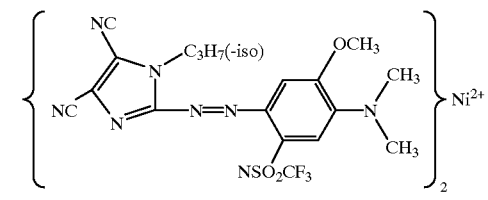
Referring to the formula (V), the following compounds may be mentioned as preferred examples of the metal chelate compound obtained from an azo compound and a metal salt.
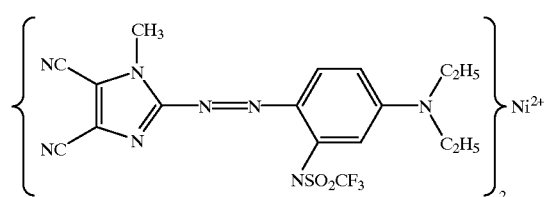
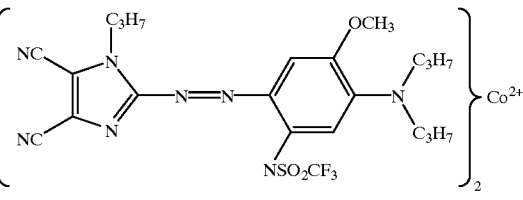
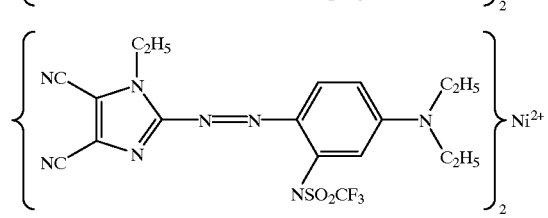
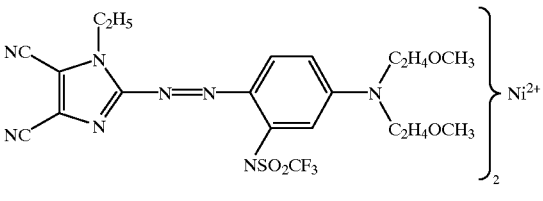
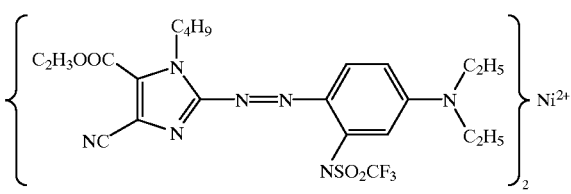
Referring to the formula (VI), the following compounds may be mentioned as preferred examples of the metal chelate compound obtained from an azo compound and a metal salt.
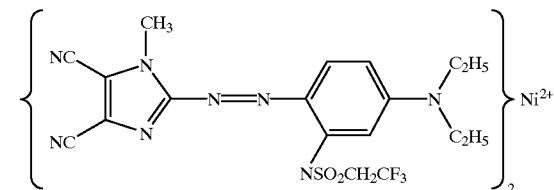
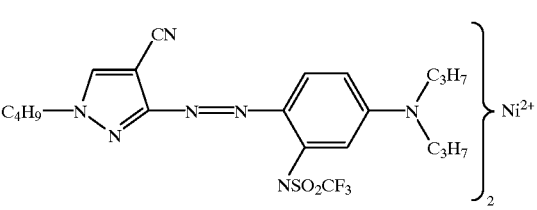
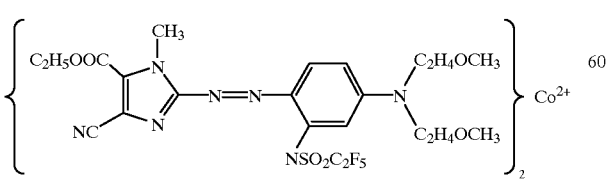
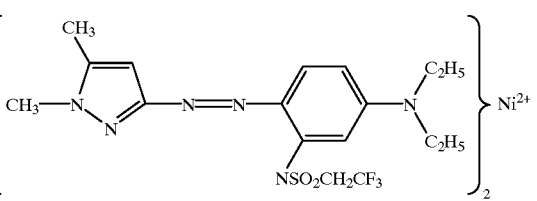

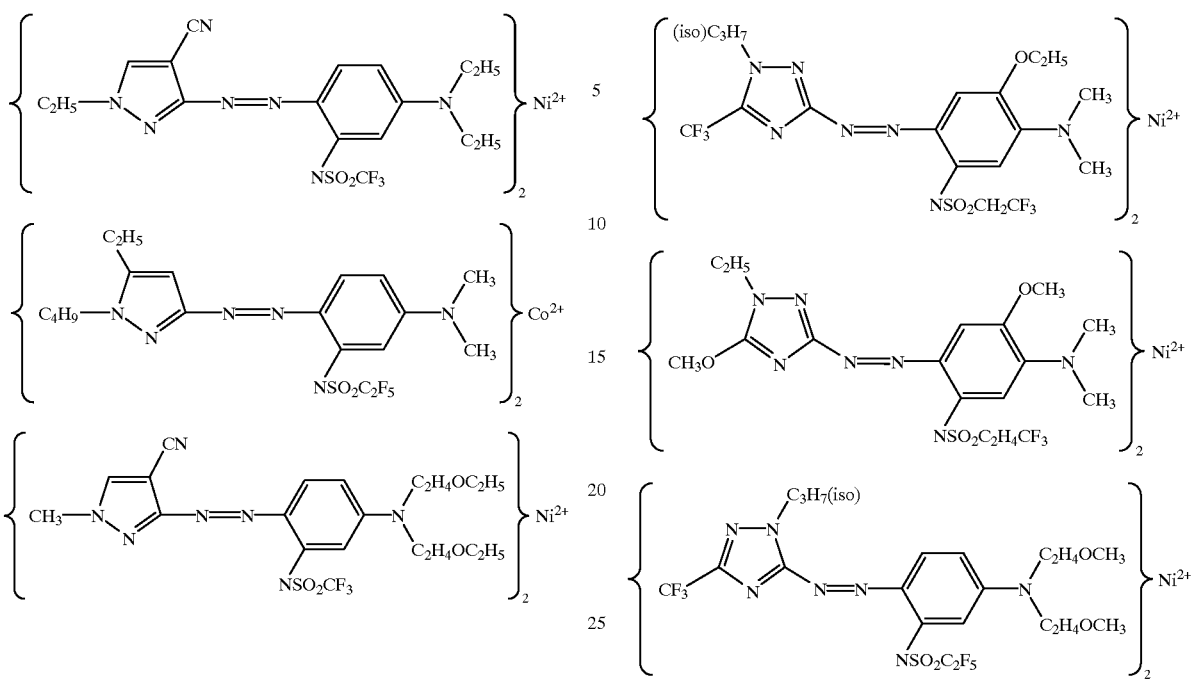
Referring to the formulae (VII), (VIII) and (IX), the following compounds may be mentioned as preferred examples of the metal chelate compound obtained from an azo compound and a metal salt.
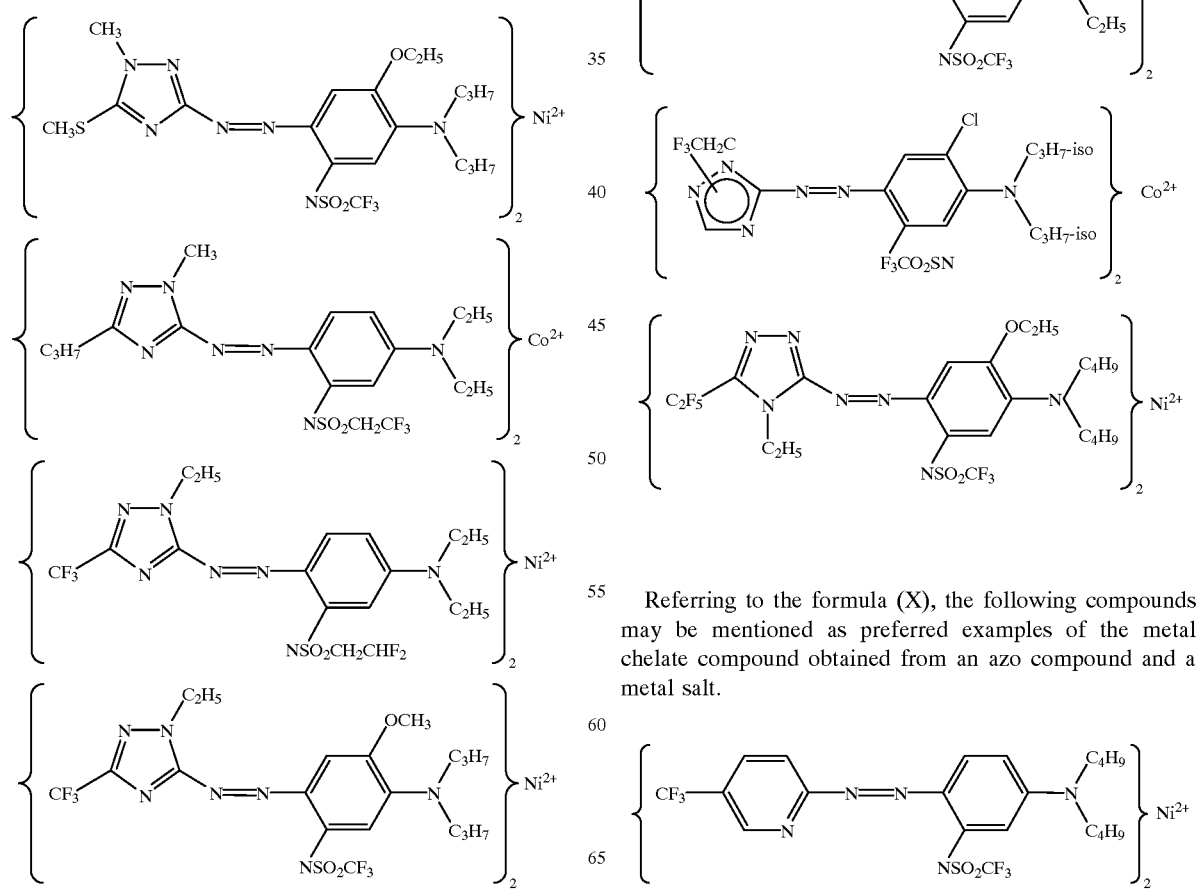
Referring to the formula (X), the following compounds may be mentioned as preferred examples of the metal chelate compound obtained from an azo compound and a metal salt.

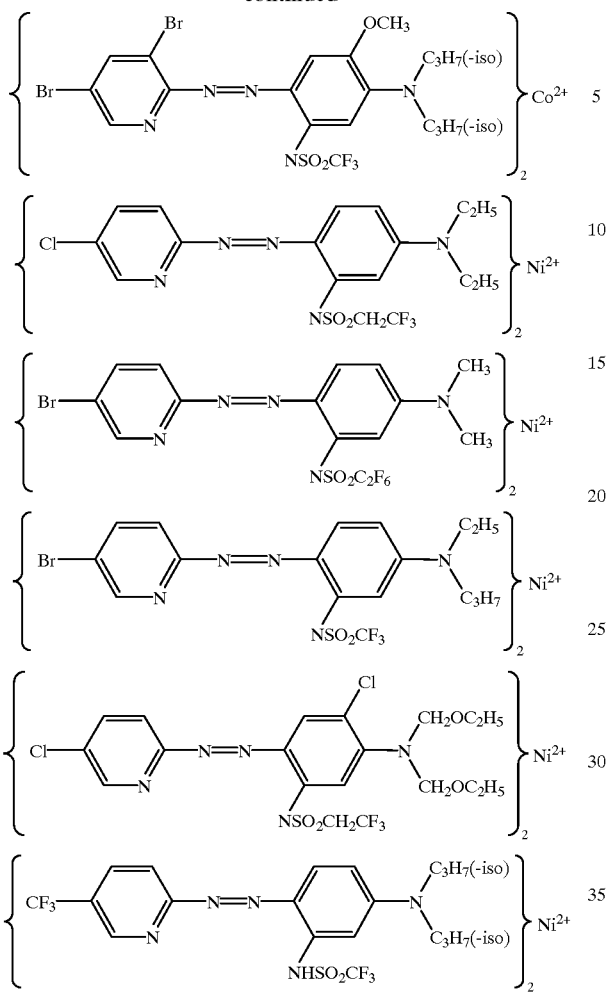

In the present invention, as the metal salt for forming a chelate compound together with the azo compound, various metal salts capable of forming complexes, can be employed. However, a salt of Ni, Co or Cu is preferred from the viewpoint of the good absorption spectrum pattern. Particularly preferred is a Ni salt from the viewpoint of the solubility in various solvents, the light resistance and the durability.

The metal chelate compound of the present invention can be obtained in such a manner that an amino compound of the formula (XI):

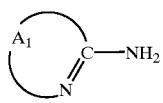

(XI)

wherein A1 is as defined in thew formula (I), is diazotized by a conventional method and then reacted with a coupling components of the formula (XII):

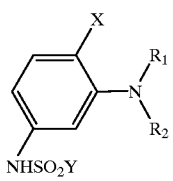

(XII)

wherein X, Y, $R_1$ and $R_2$ are as defined in the formula (I) to obtain an azo compound, and a methanol solution or aqueous solution of a metal compound is added to the azo compound in an organic solvent such as methanol, tetrahydrofuran or acetone.

The optical recording medium for short wavelength recording of the present invention consists essentially of a substrate and a recording layer comprising the metal chelate compound of the above azo compound with a metal. Further, an undercoating layer may be provided on the substrate, as the case requires. As a preferred example of the layer structure, a medium having a high reflectance may be mentioned in which a metal reflecting layer such as gold, silver or aluminum and a protective layer are formed on the recording layer. The above substrate is preferably transparent to the laser beam to be used, and glass or various plastics may be employed. The plastics include, for example, an acrylic resin, a methacrylic resin, a polycarbonate resin, a vinyl chloride resin, a vinyl acetate resin, a polyester resin, a polyethylene resin, a polypropylene resin, a polyimide resin, a polystyrene resin and an epoxy resin. However, an injection molded polycarbonate resin substrate is particularly preferred from the viewpoint of the high productivity, costs and moisture absorption resistance.

The recording film for the recording layer comprising the metal chelate compound of the azo compound with a metal in the optical recording medium of the present invention, can be formed by a convent ional film-forming method such as a vacuum deposition method, a sputtering method, a doctor blade method, a casting method, a spinning method or a dipping method. However, from the viewpoint of the mass production and costs, a spinning method is preferred.

Further, a binder may be used as the case requires. The binder may, for example, be a conventional one such as polyvinyl alcohol, polyvinylpyrrolidone, a ketone resin, nitrocellulose, cellulose acetate, polyvinylbutyral or polycarbonate. In the case of film forming by the spinning method, the rotational speed is preferably from the 500 to 5000 rpm. After the spin coating, heating or treatment such as applying a solvent vapor, may be carried out, as the case requires.

Further, in order to improve the light resistance or the stability of the recording layer, a transition metal chelate compound such as acetyl acetonate chelate, bisphenyldithiol, salicylic aldehyde oxime or bisdithio-α-diketone, may be incorporated as a singlet oxygen quencher. Further, other dyes may be used in combination, as the case requires. As such other dyes, different kinds of compounds of the same type may be used, or dyes of different types, such as triarylmethane dyes, azo dyes, cyanine dyes, squarylium dyes, metal-containing indoaniline dyes or phthalocyanine dyes, may be employed.

When the recording layer is formed by a coating method such as a doctor blade method, a casting method, a spinning method or a dipping method, particularly by a spinning method, the solvent for coating is not particularly limited so long as it is a solvent not to impair the substrate. For example, it may be a ketone alcohol type solvent such as diacetone alcohol or 3-hydroxy-3-methyl-2-butanone, a cellosolve type solvent such as methylcellosolve or ethylcellosolve, a hydrocarbon type solvent such as n-hexane or n-octane, a cyclohydrocarbon type solvent such as cyclohexane, methylcyclohexane, ethylcyclohexane, dimethylcyclohexane, n-butylcyclohexane, t-butylcyclohexane or cyclooctane, an ether type solvent such as diisopropyl ether or dibutyl ether, a perfluoroalkyl alcohol type solvent such as tetrafluoropropanol, octafluoropentanol or hexafluorobutanol, or a hydroxyester type solvent such as methyl lactate, ethyl lactate or methyl isobutyrate. The recording layer of the optical recording medium of the present invention may be provided on each side of the substrate, or on one side only. Otherwise, it may be of a structure in which two media each having a recording layer formed on a substrate, are put together by bonding.

The protective layer may be any layer so long as it is capable of protecting the recording layer and the reflective layer, and it may, for example, be formed of a ultraviolet ray curable resin.

Further, a print-receiving layer may be formed on the protective layer, as the case requires.

Recording on an optical recording medium obtained as described above, is carried out by irradiating a laser beam to a recording layer formed on each side or one side of the substrate. At the portion irradiated by the laser beam, a thermal deformation of the recording layer, such as decomposition, heat generation or fusion, will take place due to absorption of the laser beam energy. Retrieving of the recorded information is carried out by reading out the difference in reflectance between the portion where the thermal deformation took place and the portion where no such deformation took place, by means of a laser beam.

As the laser, various types may be used. However, one having a wavelength of from 600 to 700 nm is preferred from the viewpoint of the light absorption of the recording layer. Further, a semiconductor laser is preferred from the viewpoint of light weight, efficiency in handling, compactness and costs.

Further, the novel metal chelate compound of the present invention is useful for applications other than the above mentioned application for optical recording medium, such as for coloring various materials such as plastics or paper, for dying of various fibers and for coloring optical filters, and thus it is a very useful compound.

Now, the present invention will be described in detail with reference to Examples. However, it should be understood that the present invention is by no means restricted to such specific Examples.

In the following examples, $\epsilon$ (molecular extinction coefficient) was calculated on an assumption that two molecules of an azo compound were coordinated per a metal atom.

EXAMPLE 1

8.8 g (0.05 mol) of 3-N,N-diethylaminoaniline having a purity of 93%, was dissolved in 20 ml of toluene. In a nitrogen stream, 20 g of trifluoromethane sulfonic anhydride was maintained at a temperature of not higher than 20° C with stirring, and the above toluene solution was dropwise added hereto over a period of about 30 minutes. Then, the mixture was stirred for one hour, at a temperature or from: 0 to 5° C and then kept to stand overnight. The reaction solution was poured into 200 ml of ice water, and the water layer was removed by decantation. To the toluene layer in which white precipitates were formed, 50 ml of n-hexane was added to obtain slightly brown crystals. The crystals were collected by filtration, washed with water and dried to obtain 15.21 g of a trifluoromethane sulfonate of 3-N,N-diethylamino-trifluoromethane sulfonanilide, which is the compound No. 1 in Table 1. The results of its elemental analysis are as shown in Table 3.

TABLE 3

| | C | H | N | |
|---|---|---|---|---|
| Calculated Values | 32.3% | 3.6% | 6.3% | (As $C_{12}H_{16}F_6N_2O_5S_2$) |
| Analyzed Values | 32.0% | 3.5% | 6.2% | |

The results agreed to the calculated values of

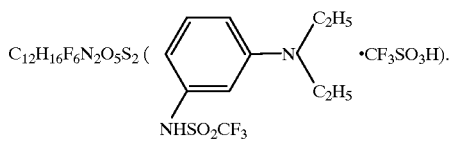

Figure 1:
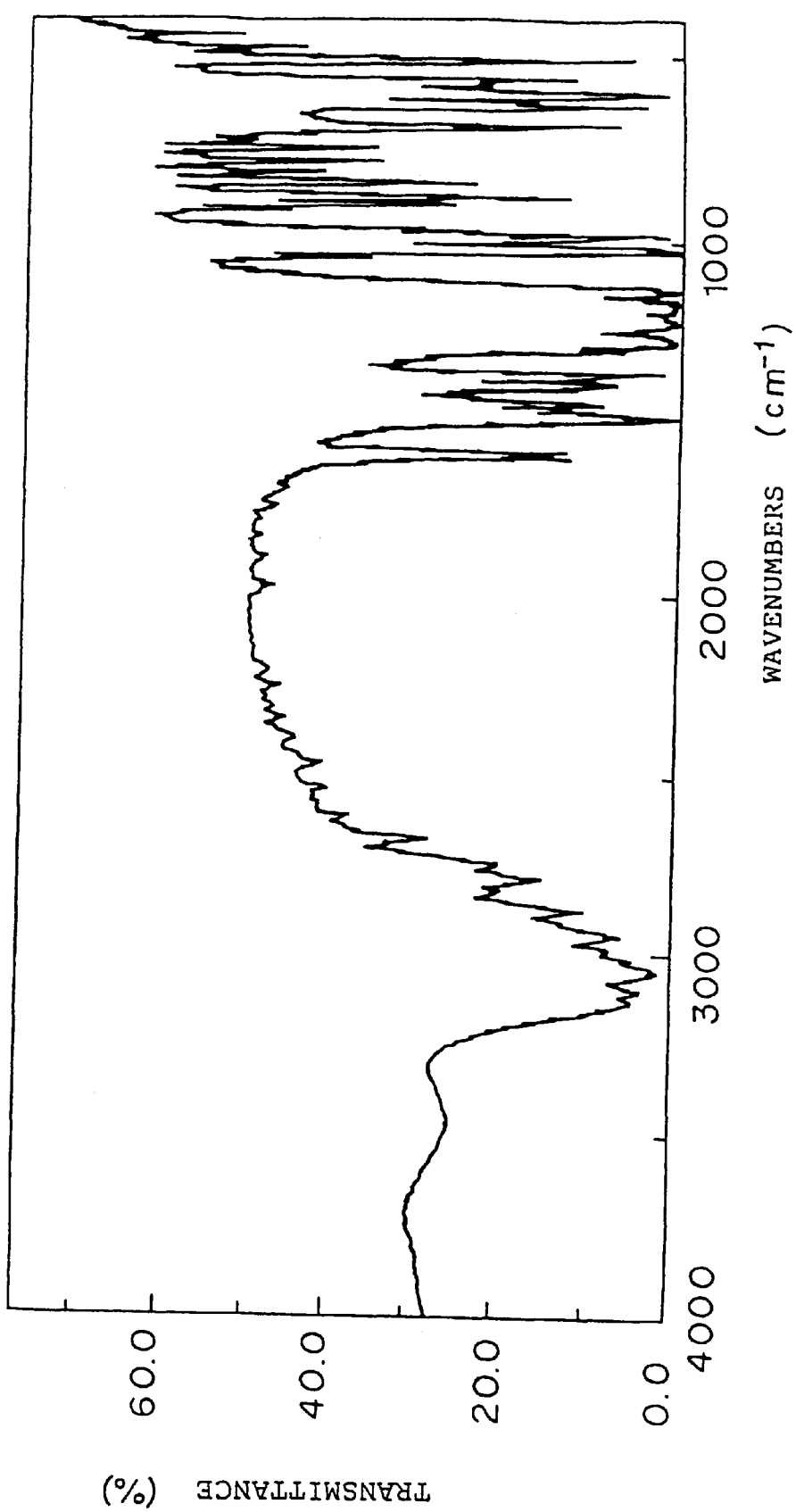
FIG. 1 is an IR spectrum of the trifluoromethane sulfonate of 3-N,N-diethylamino-trifluoromethane sulfonanilide obtained in Example 1.

Further, the mass spectrum of this compound was M⁺296, and it was detected in the form wherein the trifluoromethane sulfonic acid was removed. The IR spectrum of this compound is shown in FIG. 1.

Then, 5 g of the trifluoromethane sulfonate of 3, N,N-diethylamino-trifluoromethane sulfonanilide obtained as described above, was dissolved in 10 ml of methanol at a temperature of from 20 to 25° C. Then, 5 g of sodium acetate was added thereto, and the mixture was stirred for one hour at a temperature of from 20 to 25° C. Then, 20 ml of water was added thereto, and the mixture was extracted with 50 ml of toluene. The obtained extract solution was washed three times with 100 ml of water and then dried over sodium sulfate. Purification by column chromatography was carried out by means of a column packed with Wako gel C-200 (silica gel, manufactured by Wako Junyaku K.K.), and toluene was distilled off from the main fraction under reduced pressure to obtain 1.82 g of grayish white crystals of 3-N,N-dimethylamino-trifluoromethyl sulfonanilide, which is the compound No. 1 in Table 1.

The results of the elemental analysis of this product are as shown in Table 4 and agreed to the calculated values of $C_{11}NH_{15}F_3N_2O_2S$

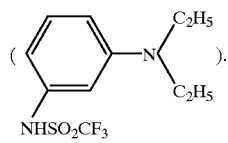

TABLE 4

| | C | H | N | |
|---|---|---|---|---|
| Calculated Values | 44.6 | 5.1 | 9.5 | (As $C_{12}H_{16}F_6N_2O_5S_2$) |
| Analyzed Values | 44.7 | 5.0 | 9.4 | |

Figure 2:
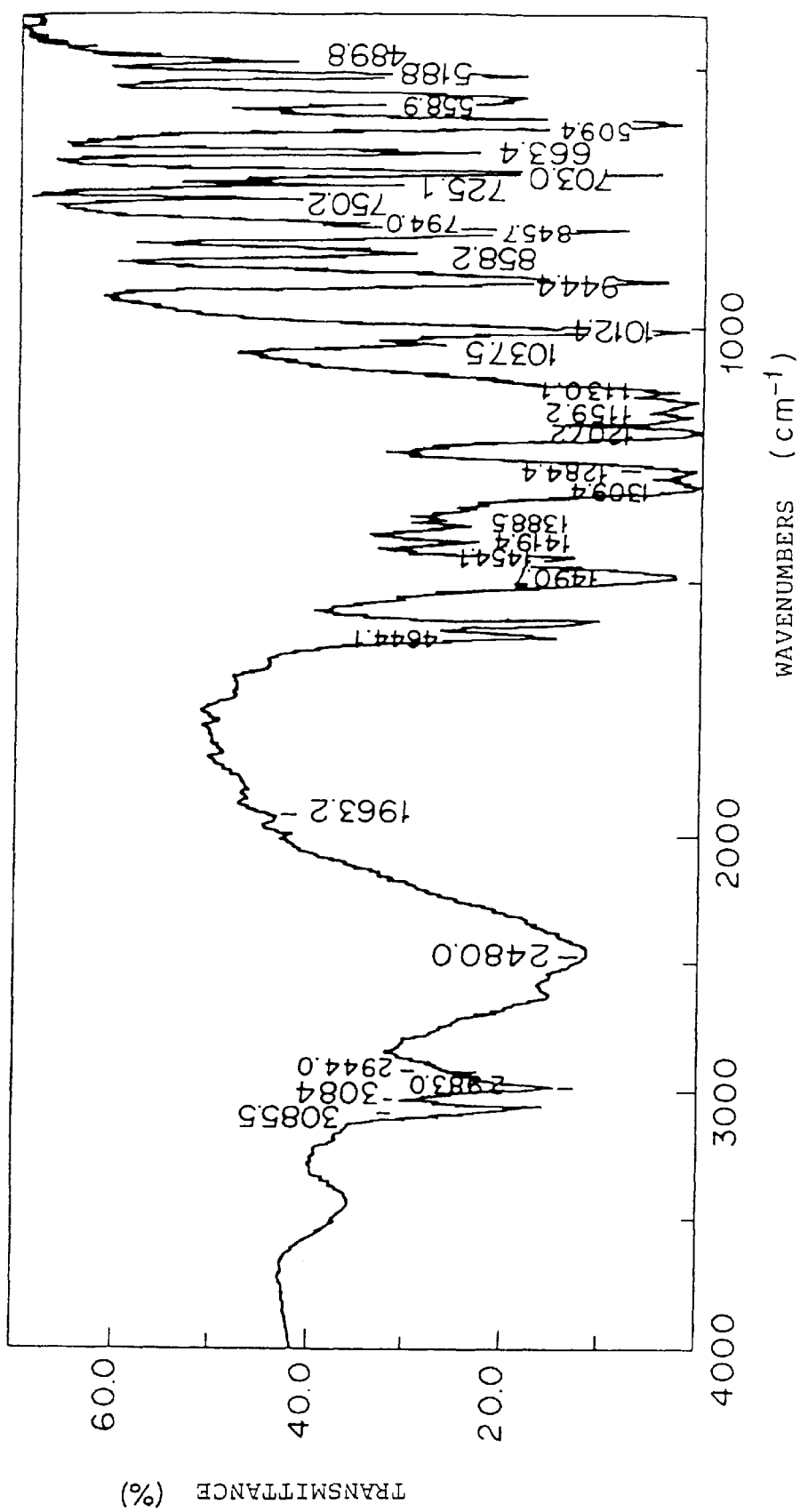
FIG. 2 is an IR spectrum of 3-N,N-diethylamino-trifluoromethane sulfonanilide obtained in Example 1.

The IR spectrum of this product is shown in FIG. 2.

EXAMPLE 2

3-aminoacetanilide and n-butyl bromide were reacted in N-methylpyrrolidone in the presence of potassium carbonate to obtain 3-N,N-di-n-butylamino-acetanilide. This product was added to and dissolved in a 10 vol % sulfuric acid aqueous solution, followed by stirring under reflux for 4 hours. Then, the reaction solution was neutralized with sodium hydroxide and extracted with toluene to obtain 3-N,N-di-n-butylaminoaniline.

In the same manner as in Example 1 except that this aniline compound was used, the trifluoromethane sulfonate of 3-N,N-di-n-butylamino-trifluoromethane sulfonanilide was obtained, which is the compound No. 2 in Table 1.

The mass spectrum of this product was measured, whereby M⁺352 in the form wherein the trifluoromethane sulfonic acid was removed, was detected. The IR spectrum of this product is shown in FIG. 3

EXAMPLE 3

In the same manner as in Example 1, 3-N,N-diethylamino-4-methoxyaniline was used instead of N,N-diethylaminoaniline, the trifluoromethane sulfonate of 3-N,N-diethylamino-4-methoxy-trifluoromethane sulfonanilide was obtained, which is the compound No. 8 in Table 1. The mass spectrum of this product was measured, whereby M⁺326 in the form wherein the trifluoromethane sulfonic acid was removed, was detected.

Figure 3:
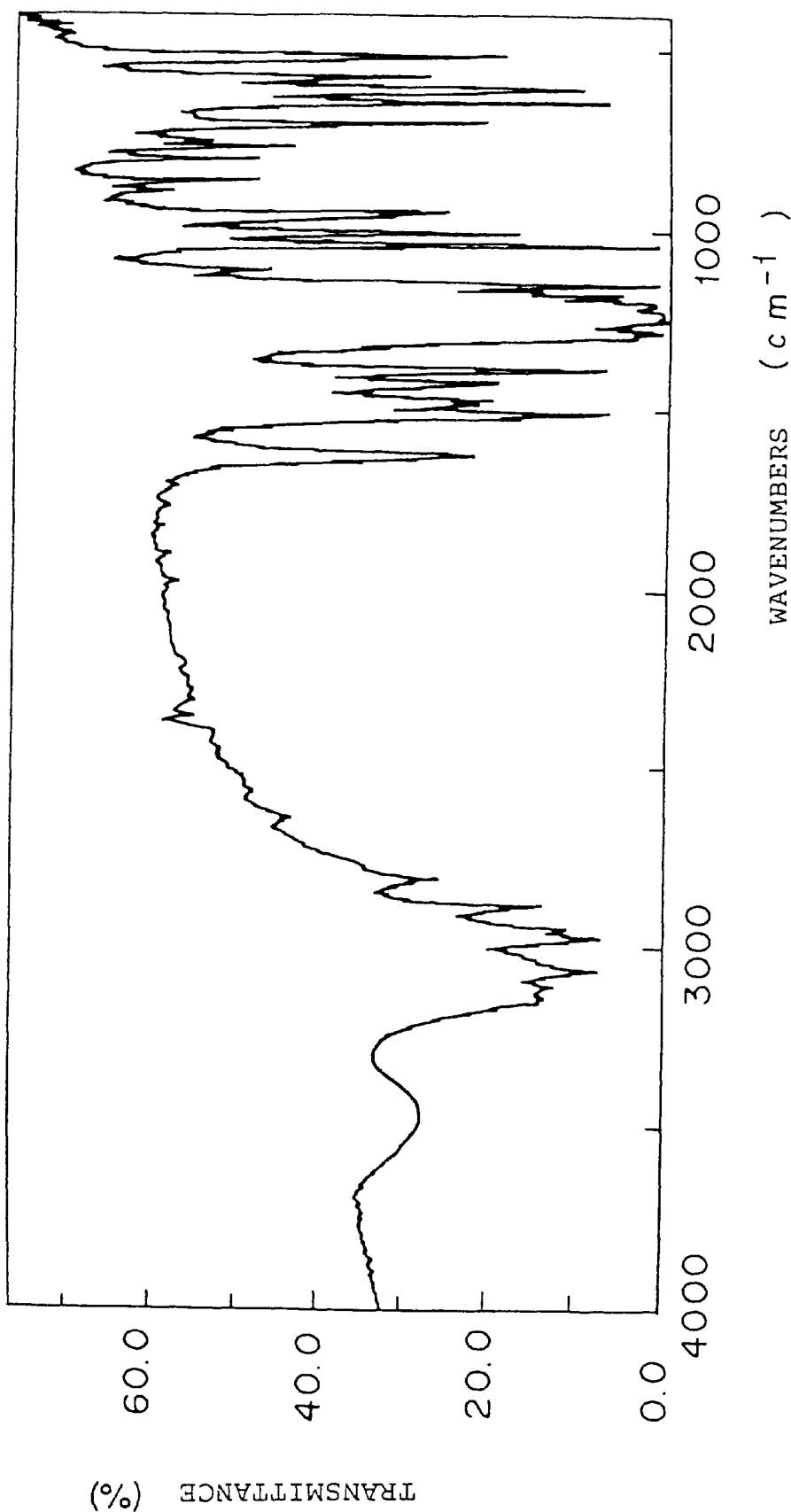
FIG. 3 is an IR spectrum of 3-N,N-di-n-butylamino-trifluoromethane sulfonanilide obtained in Example 2.
Figure 4:
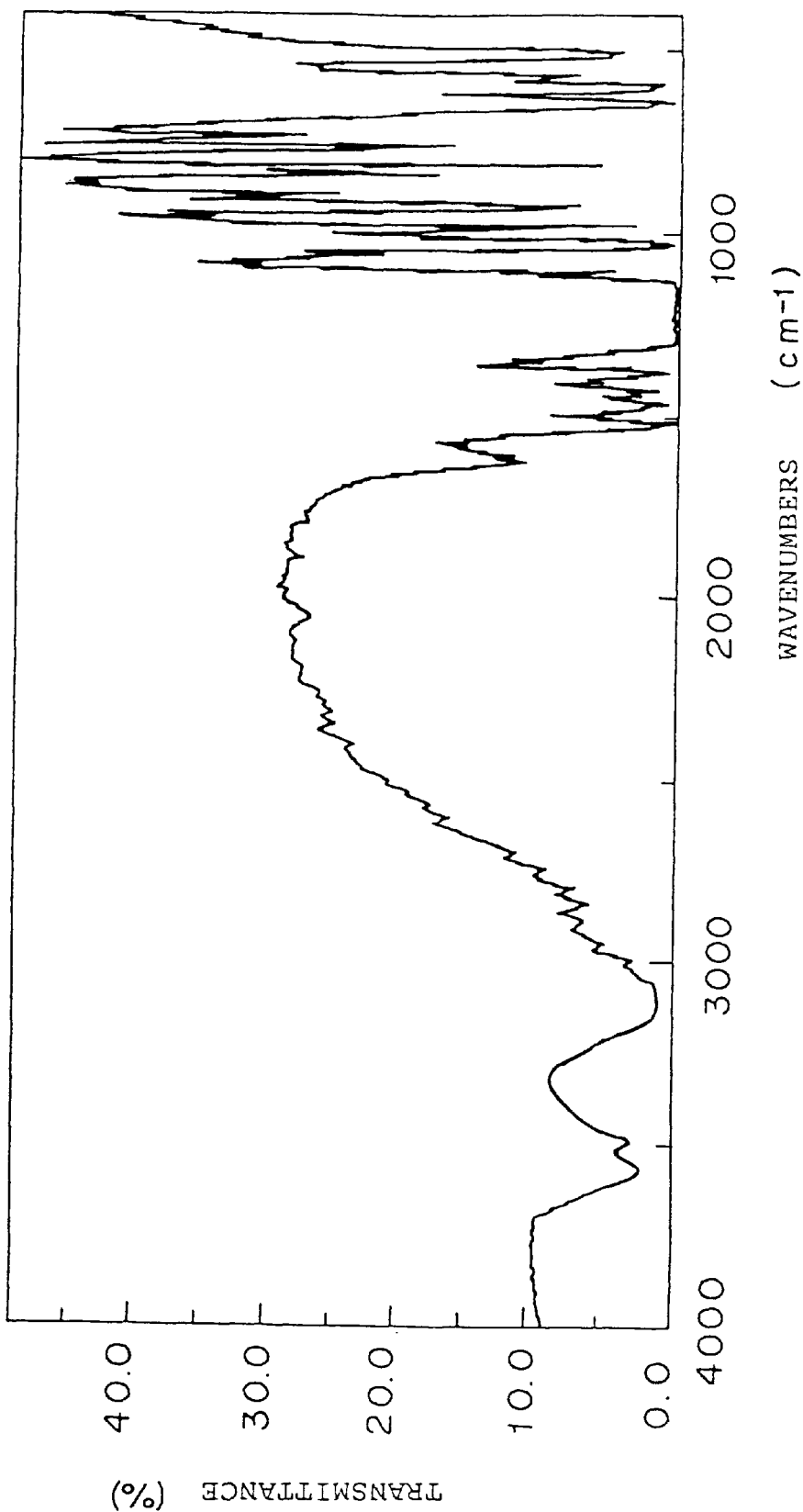
FIG. 4 is an IR spectrum of 3-N,N-diethylamino-4-ethoxy-trifluoromethane sulfonanilide obtained in Example 3.

The IR spectrum of this product is shown in FIG. 3.

EXAMPLE 4

(Sulfonamide Compund)

4.08 g (0.025 mol) of 3-N,N-diethylaminoaniline and 6.29 g (0.062 mol) of triethylamine were dissolved in 100 ml of dichloromethane at room temperature. Then, a solution having 5.0 g (0.027 mo) of 2,2,2-trifluoroethyl sulfonyl chloride dissolved in 30 ml of dichloromethane, was dropwise added thereto. The mixture was stirred at room temperature for 30 minutes, and then 50 ml of water was added thereto, followed by further stirring for 30 minutes. The reaction solution was extracted with -dichloromethane, and from the extract solution, 3-N,N-diethylamino(2,2,2-trifluoroethyl)sulfonanilide was -obtained, which is the compound No. 5 in Table 1. The molecular weight of this product was confirmed by the mass spectrum as 3-N,N-diethylamino-(2,2,2-trifluoroethyl) sulfonanilide.

EXAMPLE 5

(10)

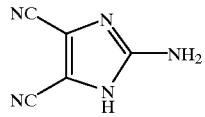

2.00 g of 2-amino-4,5-dicyanoimidazole of the above formula (10) was dissolved in 60 ml of water and 10 ml of 35% hydrochloric acid, and then 4.5 ml of an aqueous solution containing 1.14 g of sodium sulfite, was dropwise added thereto at a temperature of from 1 to 5° C. for diazotization. The obtained diazotized solution was dropwise added at a temperature of From 0 to 5° C. to a solution having 5.33 g of 3-N,N-diethylamino trifluoromethane sulfonanilide-trifluoromethane sulfonate, 0.6 g of urea and 6.0 g or sodium acetate dissolved in 65 ml of methanol, and the mixture was stirred for 3 hours and then left to stand overnight. Precipitated crystals were collected by filtration and dried to obtain 5.23 g of red crystals represented by the following formula (11):

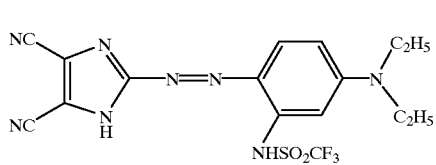

(11)

The absorption λmax in a methanol solution, of this compound, was 487 nm.

Figure 5:
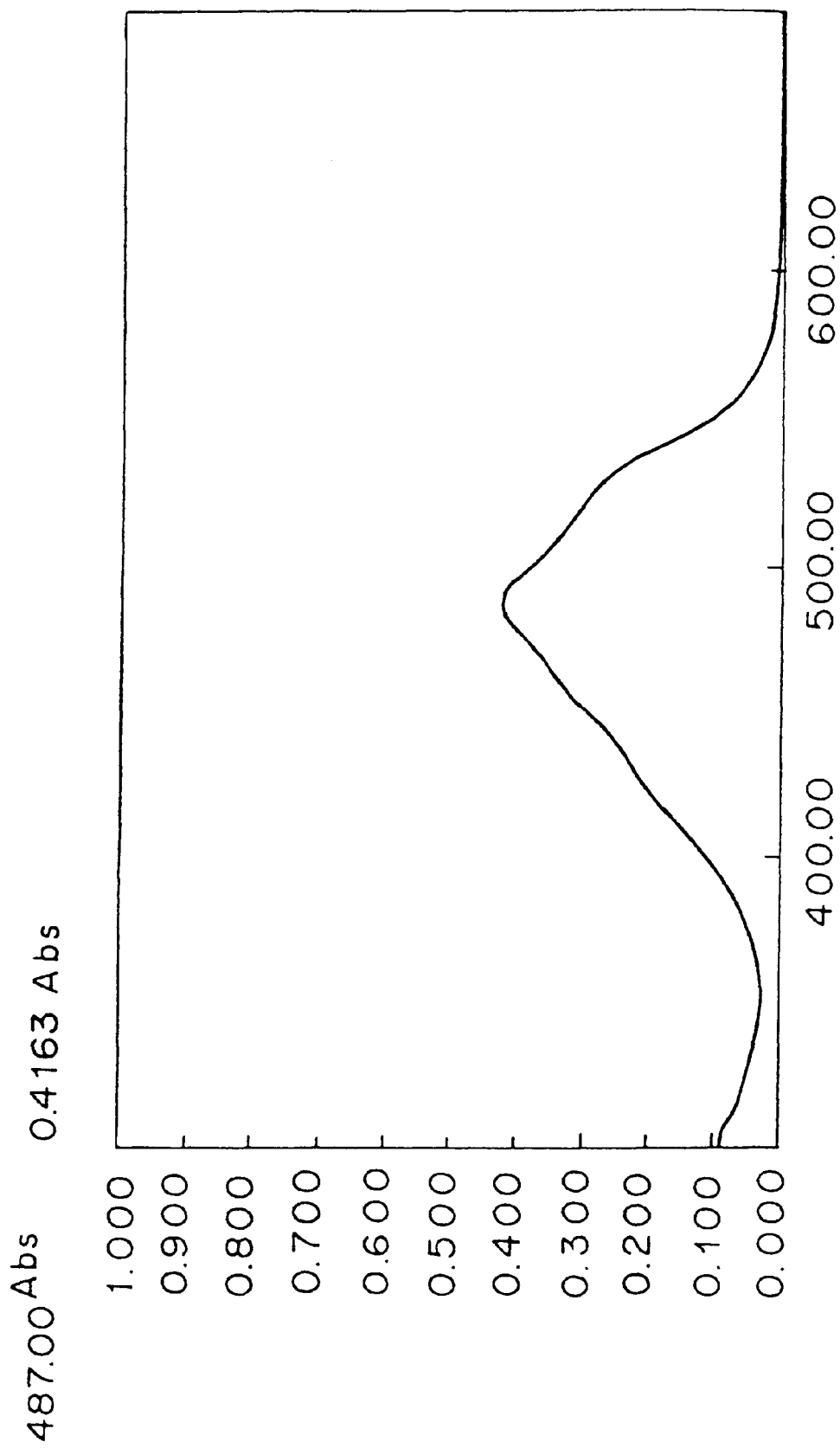
FIG. 5 is an absorption spectrum in a methanol solution, of the substance obtained in Example 5.

The absorption spectrum is shown in FIG. 5.

EXAMPLE 6

Figure 6:
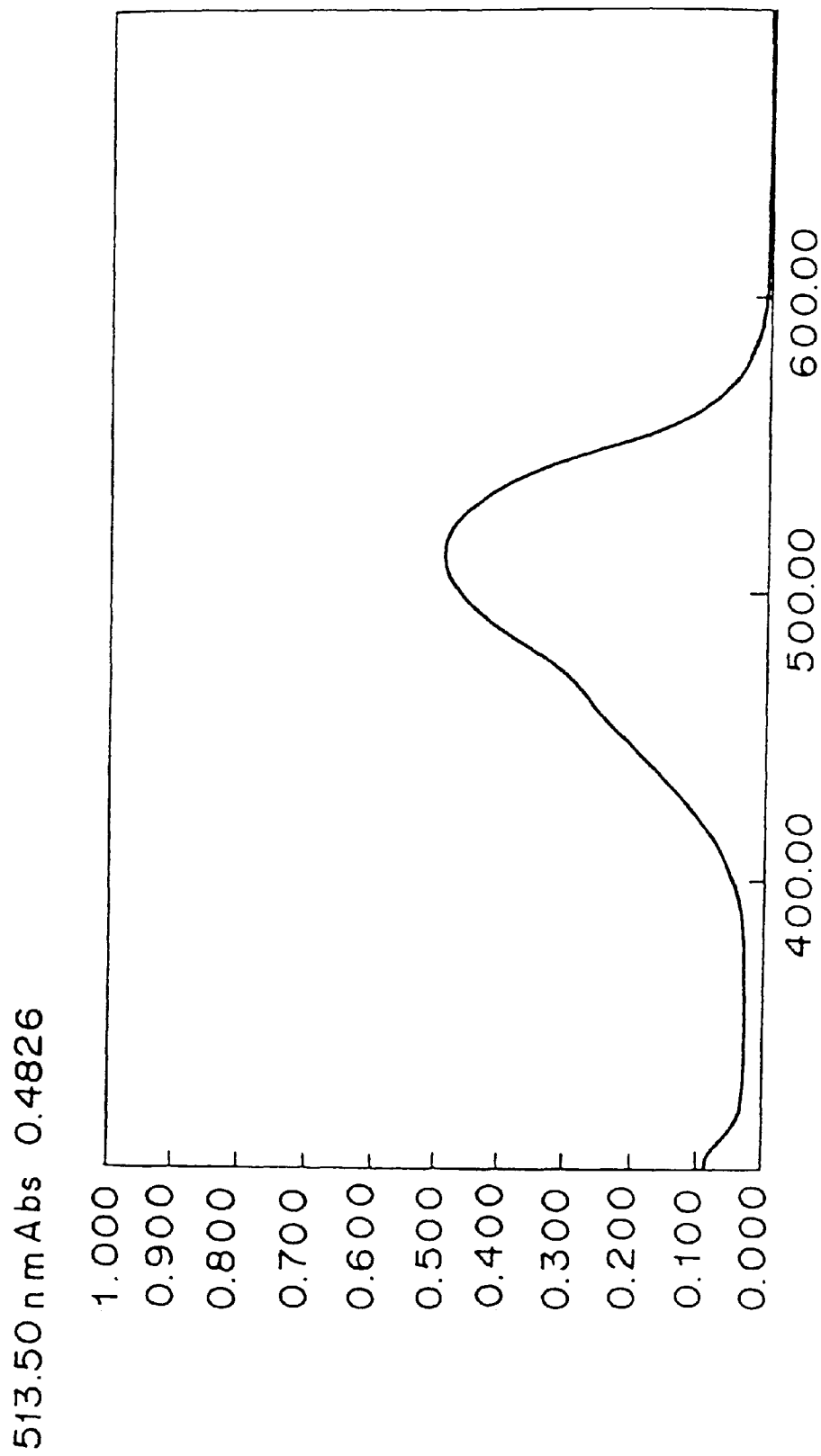
FIG. 6 is an absorption spectrum in a methanol solution, of the substance obtained in Example 6.

6.6 g of the compound of the present invention represented by the formula (11) prepared by the method of Example 5, was dissolved in 150 ml of methanol. While stirring the mixture at 20° C., 2.0 g of dimethyl sulfate was dropwise added thereto in two minutes, whereby the reaction temperature rose to 24° C. due to heat generation. Stirring was carried out at a temperature of from 24 to 25° C. for one hour, and then 2.2 g of potassium carbonate was added thereto, followed by stirring for 5 hours at a temperature of from 24 to 25° C. The formed crystals were collected by filtration and dried to obtain 2.56 g of red crystals represented by the following formula (12). The absorption λmax in a methanol solution, of this compound was 513.5 nm. The absorption spectrum is shown FIG. 6.

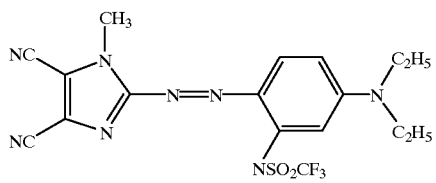

(12)

EXAMPLE 7

4.4 g of the compound of the present invention represented by the structural formula (11) prepared by the method as described in Example 5, was dissolved in 35 ml of N,N-dimethylformamide (hereinafter referred to simply as DMF), and 1.38 g of potassium carbonate was added thereto. While stirring at a temperature of from 15 to 25, 1.87 g of ethyl iodide was dropwise added thereto in ten minutes. The mixture was heated to a temperature of from 60 to 63° C. and reacted for 3 hours. Then, after cooling to a temperature of from 10 to 15° C., 25 ml of deionized water was dropwise added thereto in about 15 minutes. The mixture was left to stand overnight, and then crystals were collected by filtration and washed with water. The obtained crystals were dispersed in 100 ml of methanol and stirred for one hour at a temperature of from 15 to 25° C. Then, the crystals were collected by filtration, washed with methanol and dried to obtain 2.37 g of a red compound represented by the following structural formula (13).

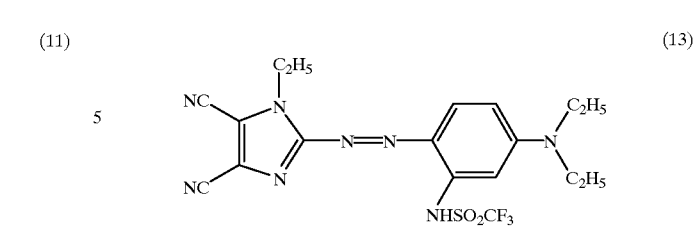

(13)

The absorption λmax of this compound in a mixed solution of DMF/methanol (5/95), was 517.5 nm.

Figure 7:
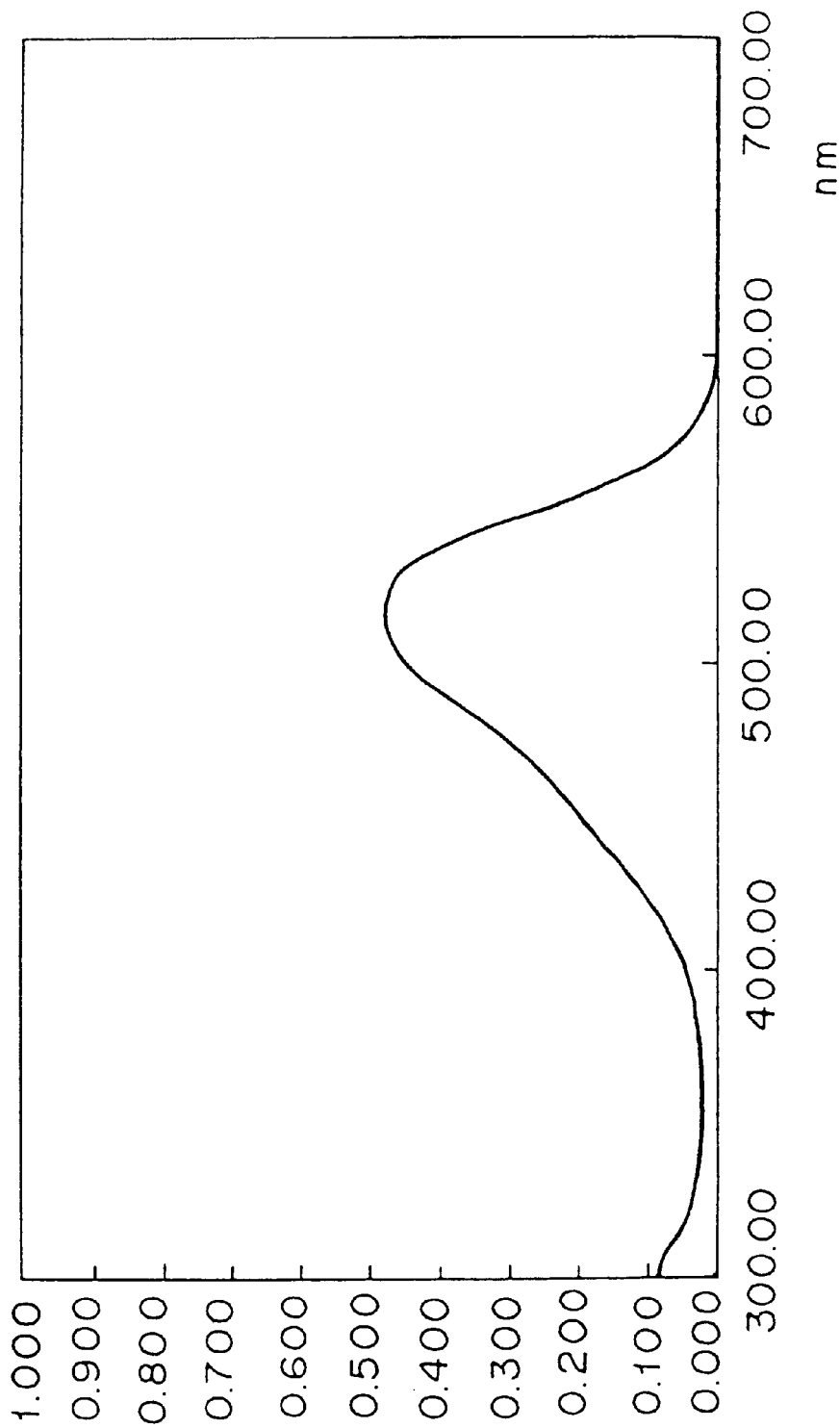
FIG. 7 is an absorption spectrum in a methanol solution, of the substance obtained in Example 7.

The absorption spectrum is shown in FIG. 7.

EXAMPLES 8 TO 10

Compounds of the following formulae (14) to (1a) were prepared with reference to Journal of American Chemical Society Vol. 73, p 4606–4608 (1951).

With respect to the absorption λmax in a methanol solution, the compound (14) had 459 nm, compound (15) had 476 nm, and compound (16) had 485 nm.

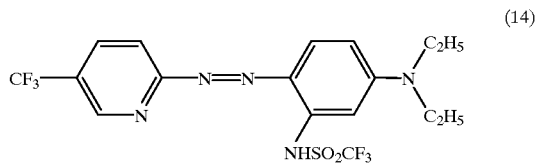

(14)

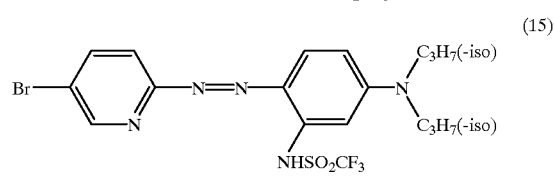

(15)

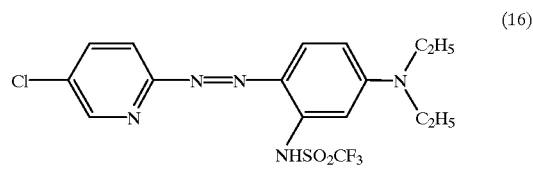

(16)

EXAMPLE 11

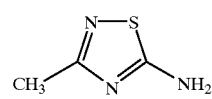

(17)

1.15 g of 2-amino-5-methyl-1,2,4-thiadiazole of the above structural formula (17) was dissolved in 10 ml of acetic acid and 5 ml of propionic acid, and while stirring, 1 ml of sulfuric acid was dropwise added at a temperature of from 0 to 5° C., and 3.55 g of 43% nitrosylsulfuric acid was further added at a temperature of from 0 to 5° C. for diazotization.

The obtained diazotized solution was dropwise added at a temperature of from 0 to 5° C. to a solution having 5.0 g of 3-N,N-dibutylamino trifluoromethane sulfonanilide-trifluoromethane sulfonate, 0.4 g of urea and 4.0 g of sodium sulfate dissolved in 30 ml of methanol, and the mixture was stirred for 3 hours and then left to stand overnight.

Precipitated crystals were collected by filtration and dried to obtain 1.6 g of a reddish brown compound of the following structural formula (18):

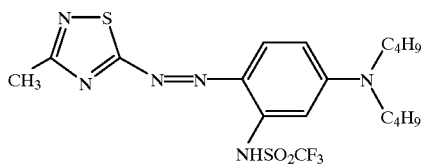
(18)

The absorption λmax in the methanol solution was 523 nm.

Figure 8:
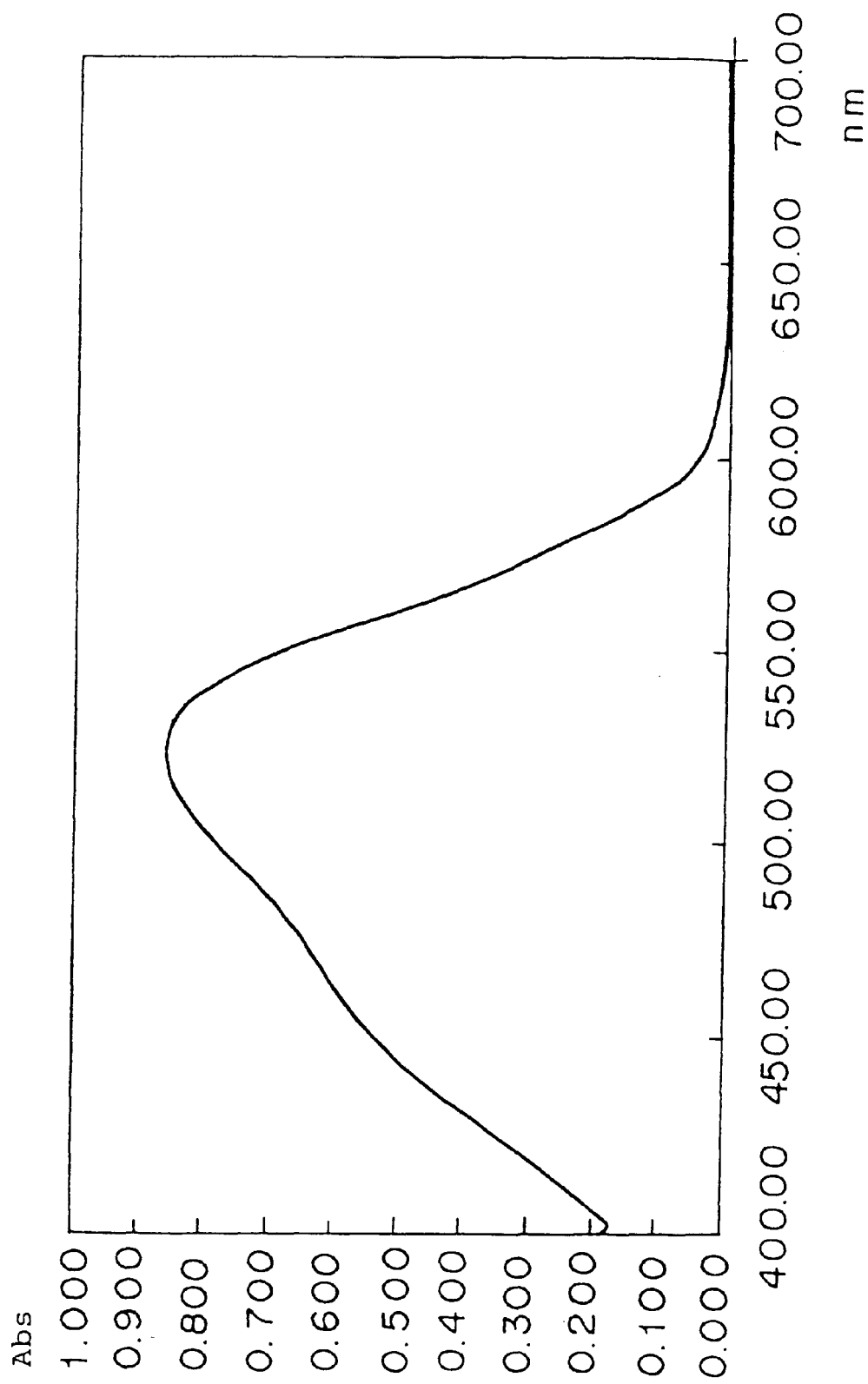
FIG. 8 is an absorption spectrum in a methanol solution, of the substance obtained in Example 11.

The absorption spectrum is shown in FIG. 8.

EXAMPLE 12

Preparation of Amino-trifluoromethyl-1,2,4-triazole

The preparation was carried out with reference to Zh. Obshch. Khim, Vol. 53, 1984 (1983). 23.1 g of trifluoroacetic acid was added to 25 g (0.184 mol) of an aminoguanidine dicarbonate, followed by mixing for 30 minutes from 20 to 25° C. 500 ml of toluene was added thereto, and the mixture was mixed under reflux for 15 hours while distilling off toluene and water formed by the reaction. The reaction mixture was left to stand overnight, and precipitated crystals were collected by filtration to obtain 14 g of white crystals of the following structural formula (19). The structure of this compound was confirmed by measuring the molecular ion peak 152 by mass spectrum.

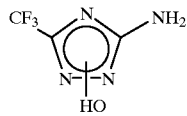
(19)

1.52 g of the compound of the formula (19) thus obtained, was dissolved in a mixed solution comprising 7.5 ml of acetic acid and 24.5 ml of propionic acid. The solution was cooled to a temperature of not higher than 5° C. while stirring. 3.6 g of a sulfuric acid solution containing 43 wt % of nitrosylsulfuric acid was added thereto at a temperature of from 3 to 5° C., and She mixture was further stirred for two hours at a temperature of from 0 to 5° C.

This reaction solution was added to a mixture preliminarily prepared by dissolving 5.24 g of 2-methoxy-5-trifluoromethylsulfonylamino-N,N-diethylaniline trifluoromethanesulfonate, 0.4 g of urea and 4 g of sodium acetate in 40 ml of methanol, at a temperature of not higher than 5° C. in about 20 minutes. At that time, ice and a 20% sodium acetate aqueous solution were optionally added not to let the pH become lower than 2 and not to let the temperature become higher than 5° C. The obtained reaction solution was further stirred for two hours at a temperature of not higher than 5° C., and then left to stand overnight. This reaction solution was subjected to filtration to obtain 3.62 g of red crystals of the following structural formula (20).

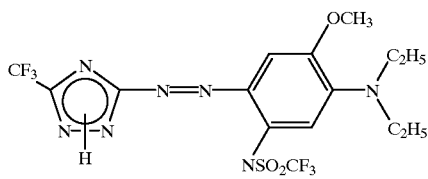
(20)

The absorption λmax in a methanol solution, of this compound, was 519.5 nm.

Figure 9:
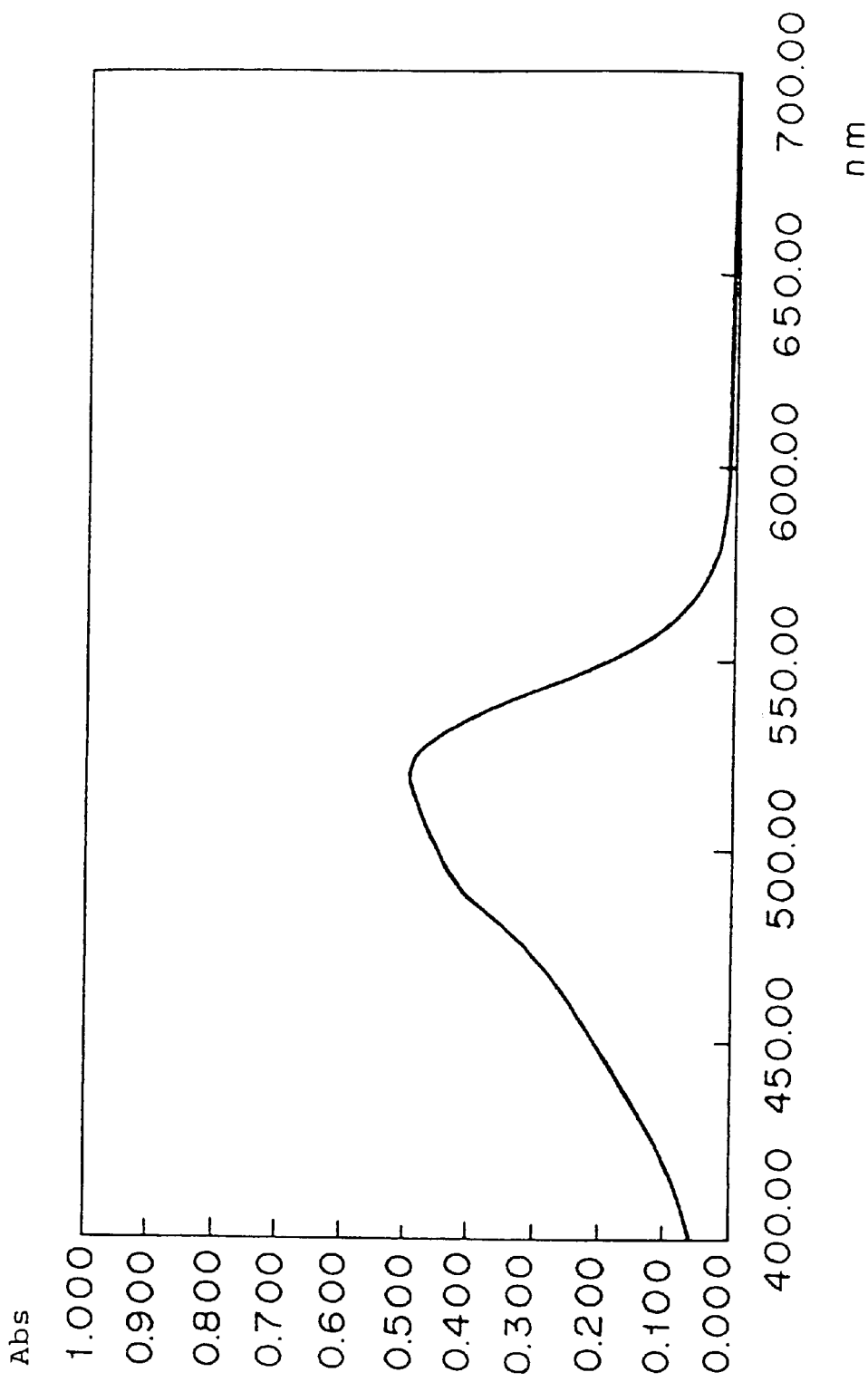
FIG. 9 is an absorption spectrum in a methanol solution, of the substance obtained in Example 12.

The absorption spectrum is shown in FIG. 9.

EXAMPLE 13

3.42 g of a azo compound of the structural formula (20) prepared by the method as described in example 12, was dispersed in 20 ml of DI-F, and 0.97 g of potassium carbonate was added thereto while stirring. A solution having 1.31 g of ethyl iodide dissolved in 5 ml of DMF, was dropwise added thereto at a temperature of from 20 to 25° C. in about 3 minutes. This reaction solution was further mixed for two hours at a temperature of from 20 to 25° C and then cooled to a temperature of not higher than 20° C. Then, 30 ml of water was dropwise added thereto in about 10 minutes. Precipitated crystals were subjected to filtration to obtain 3.0 g of red crystals of the following structural formula (21):

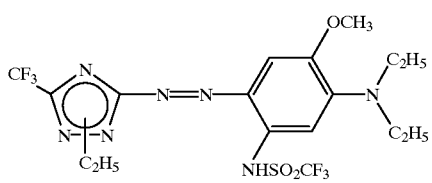
(21)

The absorption λmax in a methanol solution, of this compound, was 521 nm.

Figure 10:
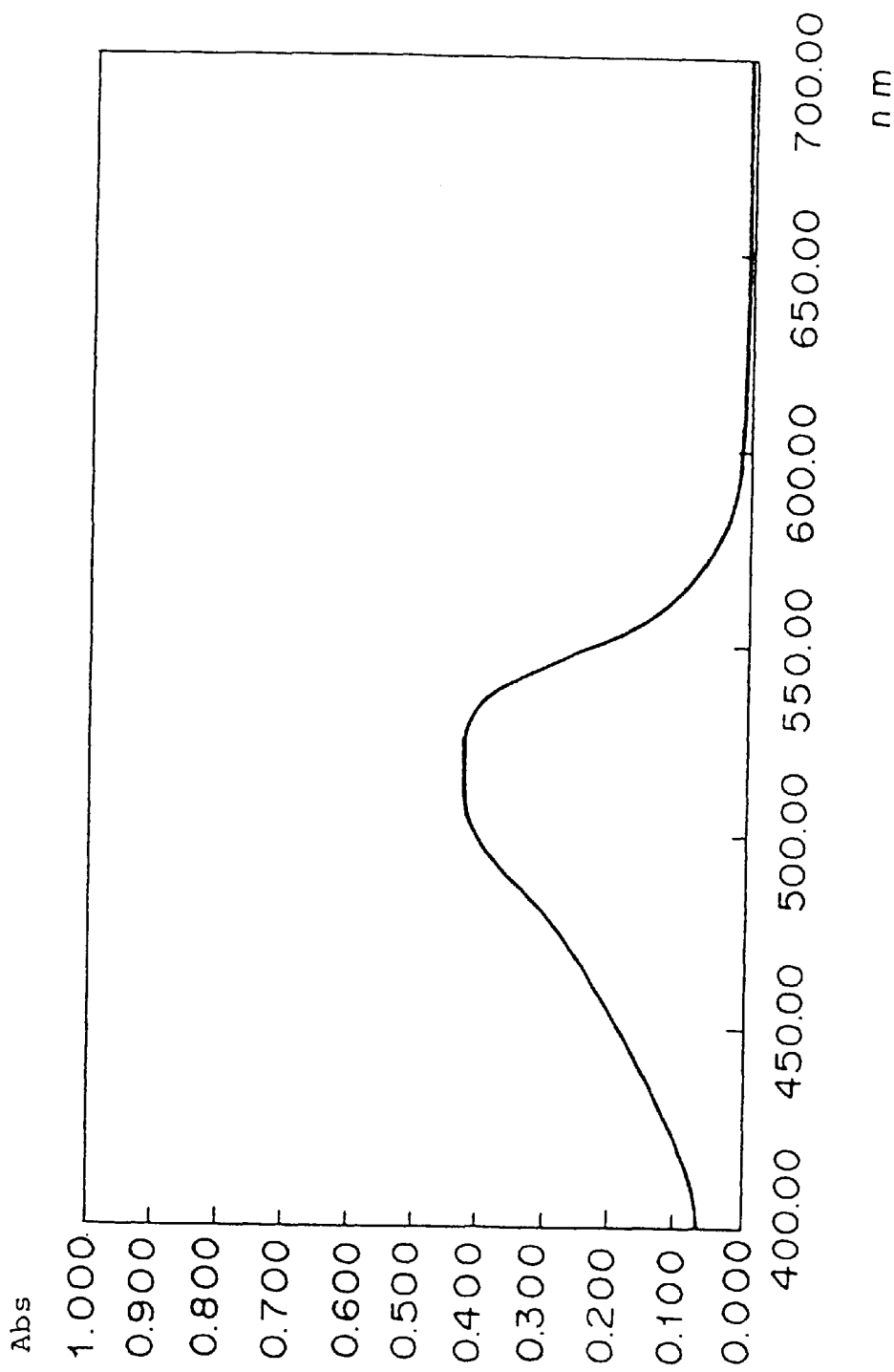
FIG. 10 is an absorption spectrum in a methanol solution, of the substance obtained in Example 13.

The absorption spectrum is shown in FIG. 10.

EXAMPLE 14

4.89 g of the azo compound of the structural formula (20) prepared by the method as described in Example 12, was dissolved in 50 ml of DMF, and 1.27 g of allyl bromide was dropwise added thereto at a temperature of from 15 to 20° C., while stirring. The mixture was stirred for 3 hours at a temperature of from 15 to 20° C., and then 50 ml of water was added thereto, followed by stirring for further two hours.

Formed crystals were collected by filtration, washed with water and dried to obtain 4.0 g of red crystals or the following structural formula (22).

The absorption λmax in a methanol solution, of this product, was 528 urn.

Figure 11:
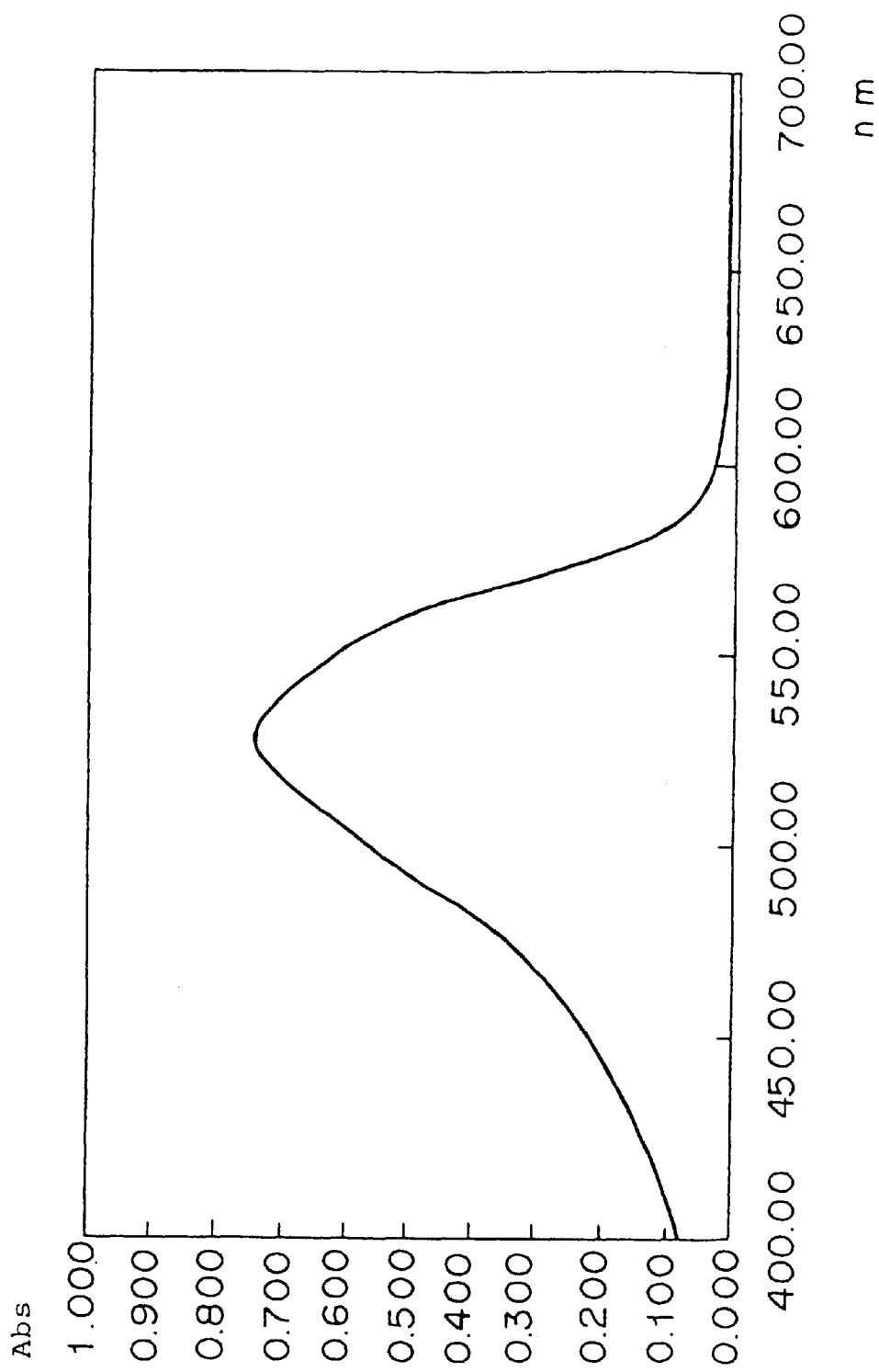
FIG. 11 is an absorption spectrum in a methanol solution, of the substance obtained in Example 14.
Figure 12:
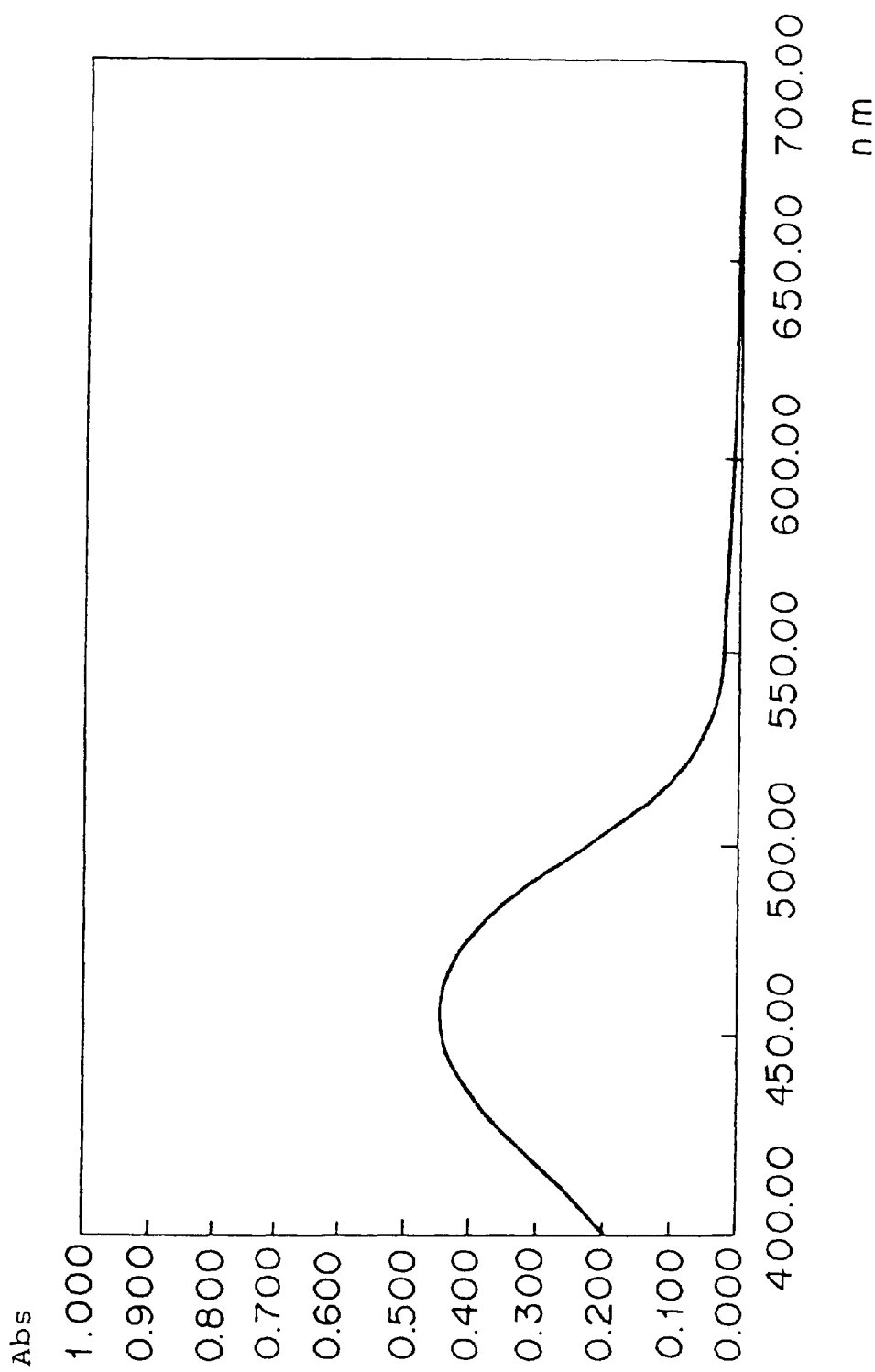
FIG. 12 is an absorption spectrum in a methanol solution, of the substance obtained in Example 15.
Figure 13:
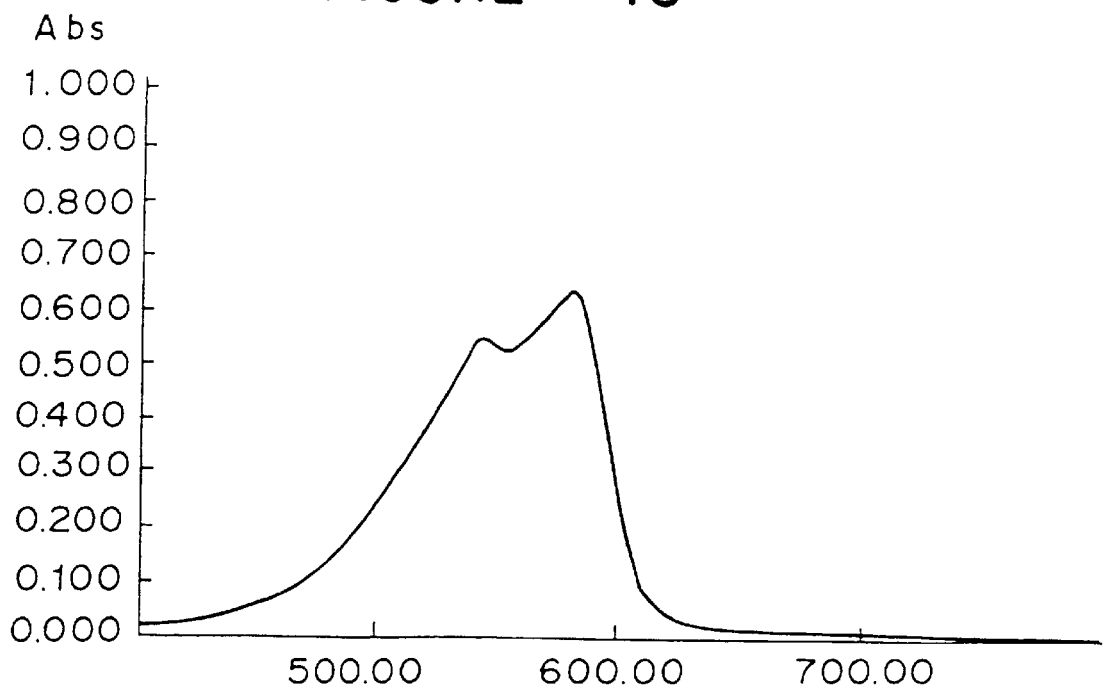
FIG. 13 is an absorption spectrum in a chloroform solution, of the metal chelate compound in Example 16.
Figure 14:
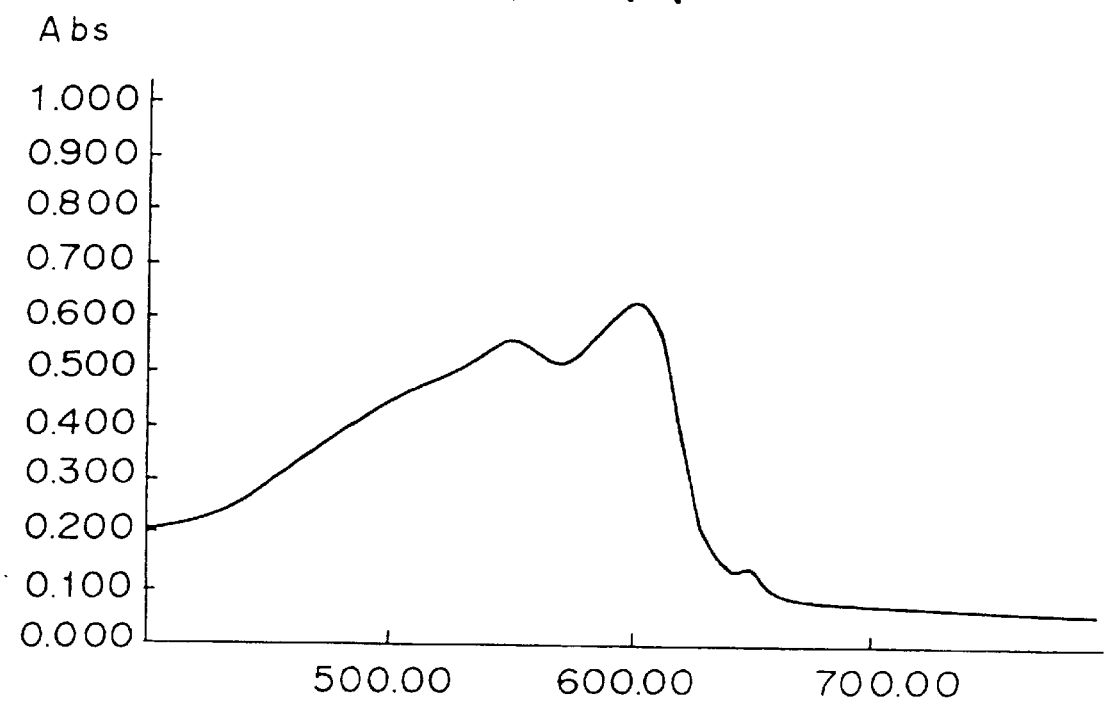
FIG. 14 is an absorption spectrum in a coating film, of the metal chelate compound of Example 16.
Figure 15:
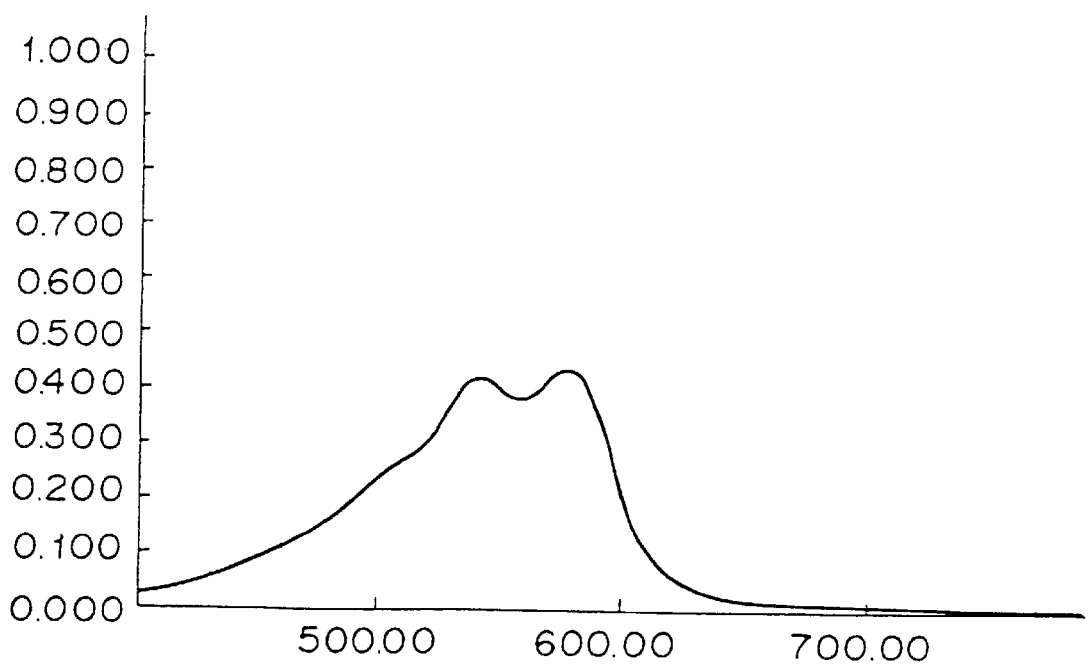
FIG. 15 is an absorption spectrum in a chloroform solution, of the metal chelate compound of Example 17.
Figure 16:
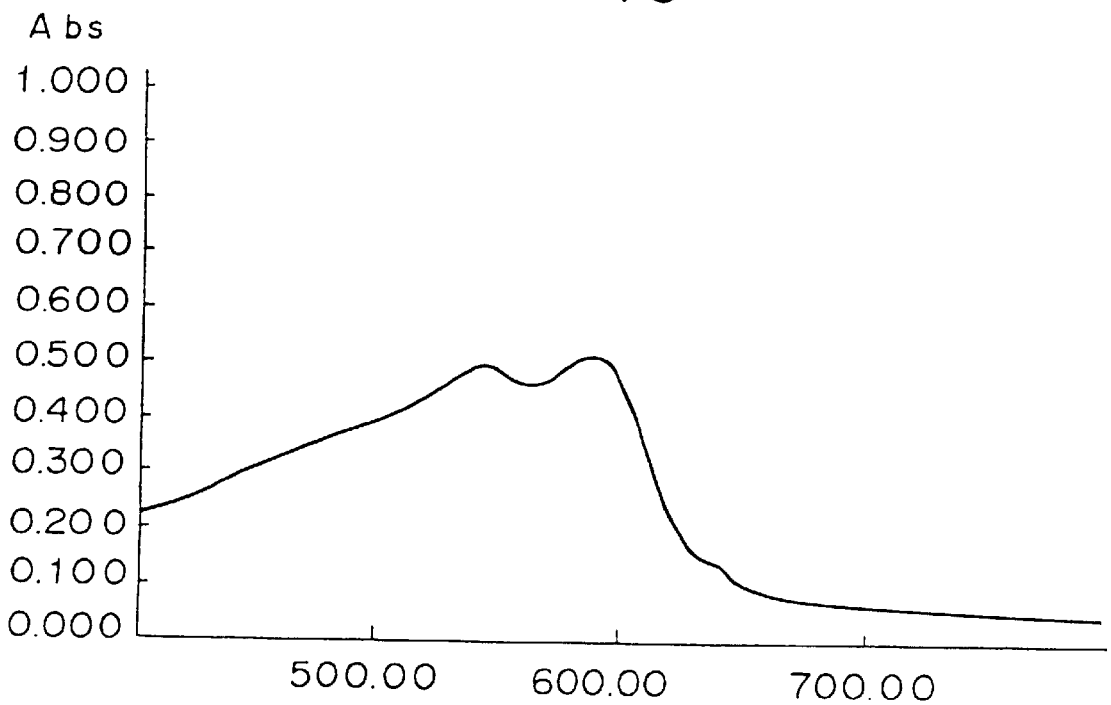
FIG. 16 is an absorption spectrum in the coating film, of the metal chelate compound of Example 17.
Figure 17:
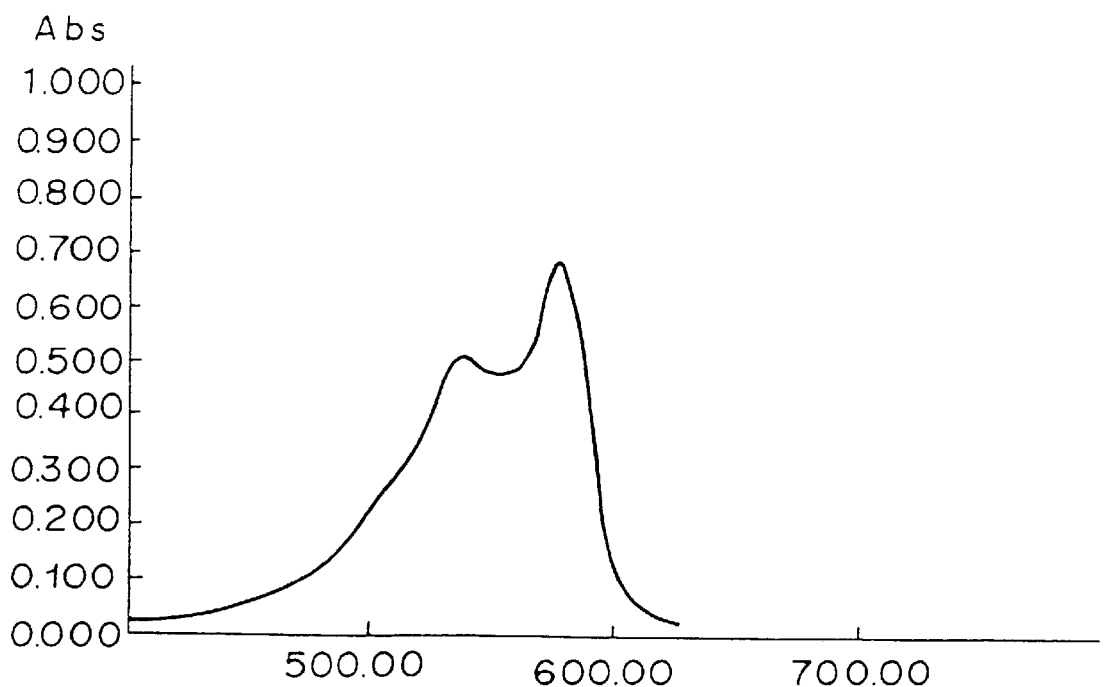
FIG. 17 is an absorption spectrum in a chloroform solution, of the metal chelate compound of Example 18.
Figure 18:
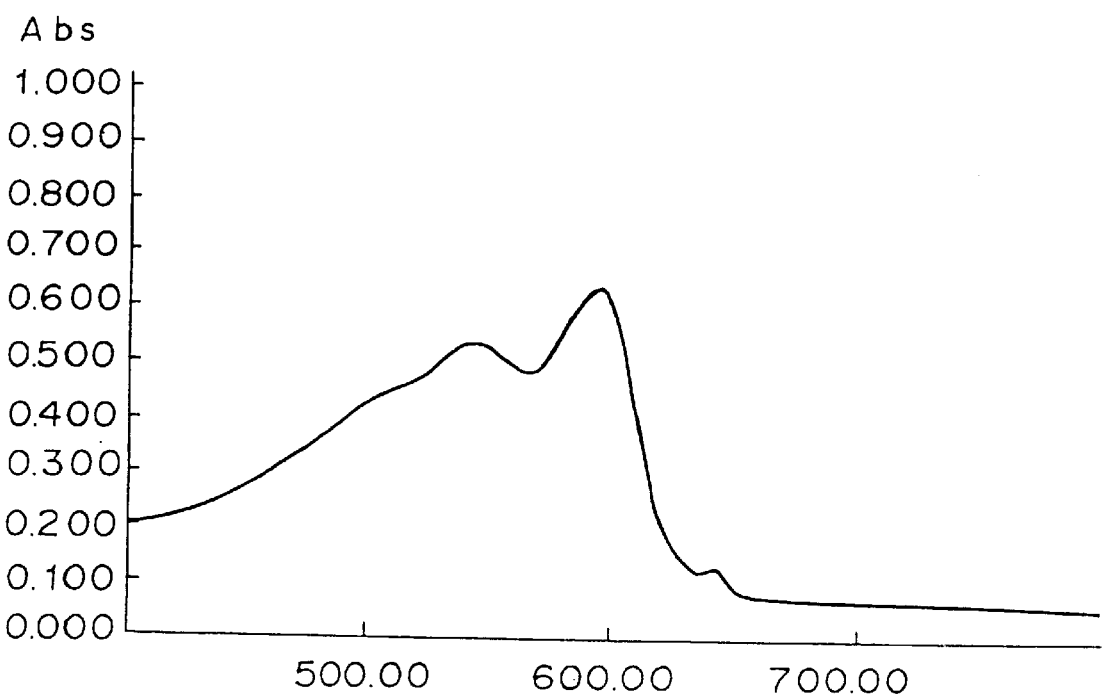
FIG. 18 is an absorption spectrum in the coating film, of the metal chelate compound of Example 18.

The absorption spectrum is shown in FIG. 11.

(22)

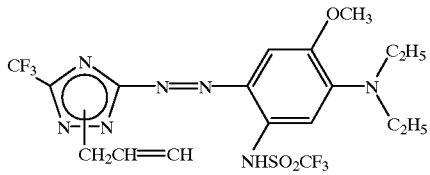

EXAMPLE 15

(23)

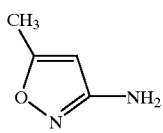

0.98 g of 3-amino-5-methylisoxazole of the above structural formula (23) was dissolved in 10 ml of acetic acid and 5 ml of propionic acid, and 1 ml of sulfuric acid was dropwise added thereto at a temperature of from 0 to 5° C., and 3.55 g of 43% nitrosylsulfuric acid was further added at a temperature of from 0 to 5° C., for diazotization. The obtained diazotized solution was dropwise added at a temperature of from 0 to 5° C. to a solution having 3.91 g of 3N,N-diethylamino-4-methoxy-trifluoromethanesulfonilide, 0.4 g of urea and 4.0 g of sodium acetate dissolved in 40 ml of methanol, and the mixture was stirred for 3 hours and then left to stand overnight. Precipitated crystals were collected by filtration and dried to obtain 2.95 g of red crystals of the following structural formula (24):

(24)

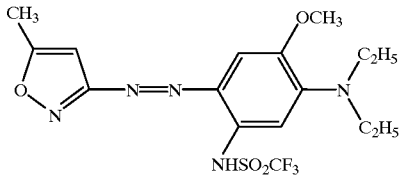

The absorption λmax in a methanol solution, of this product, was 455.5 nm.

The absorption spectrum is shown in FIG. 11.

EXAMPLE 16

(Metal Chelate Compound)
(a) Preparation example (25)

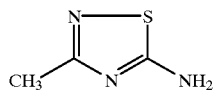

1.15 g of 2-amino-5-methyl-1,2,4-thiadiazole of the above structural formula (25) was dissolved in 10 ml of acetic acid and 5 ml of propionic acid, and 1 ml of sulfuric acid was dropwise added thereto at a temperature of from 0 to 5° C., and 3.55 g of 43% nitrosylsulfuric acid was further added at a temperature of from 0 to 5° C., for diazotization. The obtained diazotized solution was dropwise added at a temperature of from 0 to 5° C. to a solution having 4.00 g of 3-(2,2,2-trifluoromethylsulfonylamino)-N,N-diethylamino, 0.4 g of urea and 4.0 g of sodium acetate dissolved in 30 ml of methanol, and the mixture was stirred for 3 hours and then left to stand overnight. Precipitated crystals were collected by filtration and dried to obtain 1.38 g of reddish brown crystals of the following structural formula (26).

(26)

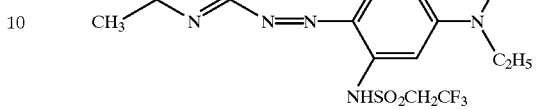

1.00 g of the azo compound of the structural formula (2) thus obtained and 0.18 g of anhydrous sodium sulfate were dissolved in 30 ml of tetrahydrofuran (THF) and 15 ml of water, and a solution having 0.34 g of nickel acetate tetrahydrate dissolved in 6 ml of methanol, was added thereto at room temperature. Then, the mixture was stirred at room temperature for two hours, and 15 ml of water was added thereto. Precipitated crystals were collected by filtration, washed with water and dried to obtain 0.70 g of a nickel chelate compound as greenish brown crystals. The absorption λmax (in chloroform) of this compound was 582 nm ($\epsilon=11.8\times10^4$)

(b) Recording medium

The nickel chelate compound obtained as described above, was dissolved in octafluoropentanol to a concentration of 1.2 wt %. This solution was subjected to supersonic dispersion at 50° C. for 30 minutes and then subjected to filtration by a filter of 0.2 μm. This solution was spin-coated on a polycarbonate substrate having a thickness of 0.6 mm at a rotational speed of 800 rpm. The groove width of this substrate was 0.35 μm (track pitch: 0.8 μm), and the groove depth was 140 nm. Then, this coated film was dried in an oven at 80° C. Then, a Au film having a thickness of 100 nm was formed on the coated film, by sputtering, to form a reflective layer. Further, on this reflective layer, an ultraviolet ray curable resin was spin-coated in a thickness of 3 μm and cured by irradiation of ultraviolet rays, to obtain a recording medium. Further, a hot melt adhesive was applied thereto, and the recording media prepared in the same manner were bonded to each other to obtain an optical disc. The absorption λmax of the coating film was 601 nm. The film thickness of the recording layer was about 120 nm.

(c) Optical recording method

EFM signals for quadruple speed recording of CD-R were input and recorded by a semiconductor laser of 635 nm (NA=0.6) at a linear speed of 2.6 m/s with a retrieving power of 0.7 mW, whereby the $I_{top}$ reflectance was 45%, and good recording characteristics were obtained with a degree of modulation of 60% with a recording power of 5 mW.

EXAMPLE 17

(Metal Chelate Compound)
(a) ?reparation example (27)

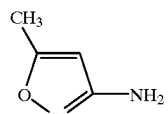

0.98 g of 3-amino-5-methylisoxazole of the above structural formula (27) was dissolved in 10 ml of acetic acid and 5 ml of propionic acid, and 1 ml of sulfuric acid was dropwise added at a temperature of from 0 to 5° C., and 3.55 g of 43% nitrosylsulfuric acid was further added at a temperature of from 0 to 5° C., for diazotization. The obtained diazotized solution was dropwise added at a temperature of from 0 to 5° C. to a solution having 3.91 g of 2-methoxy-5-trifluoromethylsulfonylamino-N,N-diethylaniline trifluoromethanesulfonate, 0.4 g of urea and 4.0 g of sodium acetate dissolved in 40 ml of methanol, and the mixture was stirred for 3 hours and then left to stand overnight. Precipitated crystals were collected by filtration and dried to obtain 2.95 g of red crystals of the following structural formula (28).

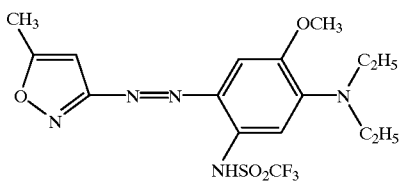

(28)

2.18 g of the azo compound of the structural formula (28) thus obtained and 0.41 g of anhydrous sodium acetate were dissolved in 80 ml of tetrahydrofuran (THF) and 40 ml of water, and a solution having 0.75 g of nickel acetate tetrahydrate dissolved in 10 ml of methanol, was added thereto at room temperature. Then, the mixture was stirred at room temperature for two hours, and 40 ml of water was added thereto. Precipitated crystals were collected by filtration, washed with water and dried to obtain 1.23 g of a nickel chelate compound as greenish brown crystals. The absorption λmax (in chloroform) of this compound was 579 nm ($\epsilon=8.1\times10^4$)

(b) Recording medium

In the same manner as in Example 16, a recording medium was prepared by using the nickel chelate compound obtained as described above. The absorption λmax of the coated film was 591 nm. The thickness of the recording layer was substantially the same as in Example 16.

(c) Optical recording method

Recording was carried out under the same conditions as in Example 16, whereby with a recording power of 5 mW, the Itop reflectance was 50%, and good recording characteristics were obtained with a degree of modulation of 55%.

EXAMPLE 18

(Metal Chelate Compound)
(a) Preparation example

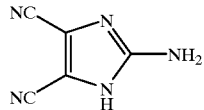

(29)

2.00 g of 2-amino-4,5-dicyanoimidazole of the above structural formula (29) was dissolved in 60 ml of water and 10 ml of 35% hydrochloric acid, and 4.5 ml of an aqueous solution containing 1.14 g of sodium sulfite, was dropwise added thereto at a temperature of from 0 to 5° C., for diazotization. The obtained diazotized solution was dropwise added at a temperature of from 0 to 5° C. to a solution having 5.33 g of 3-trifluoromethylsulfonylamino-N,N-diethylaniline trifluoromethanesulfonate, 0.6 g of urea and 6.0 g of sodium acetate dissolved in 65 ml of methanol, and the mixture was stirred for 3 hours and then left to stand overnight. Precipitated crystals were collected by filtration and dried to obtain 5.23 g of red crystals of the following structural formula (30).

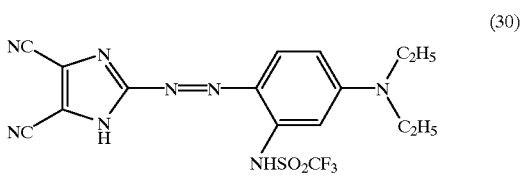

(30)

3.08 g of the azo compound of the structural formula (30) obtained as described above, and 0.96 g of potassium carbonate were dissolved in 25 ml of DMF, and 1.55 g of butyl iodide was dropwise added thereto. Then, the mixture was heated to 70° C. After stirring at 70° C. for 3 hours, the mixture was left to cool, and 10 ml of water was added thereto. Precipitated crystals were collected by filtration and dried to obtain 2.37 g of red crystals of the following structural formula (31).

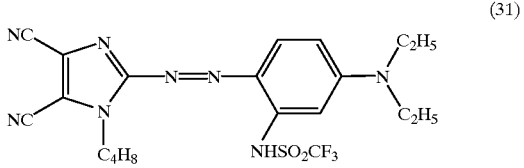

(31)

2.23 g of the azo compound of the structural formula (31) obtained as described above, and 0.37 g of anhydrous sodium acetate were dissolved in 72 ml of THF and 436 ml of water, and a solution having 0.67 g of nickel acetate tetrahydrate dissolved in 9 ml of methanol was added thereto at room temperature. Then, the mixture was stirred at room temperature for two hours, and 36 ml of water was added thereto. Precipitated crystals were collected by filtration, washed with water and dried to obtain 1.91 g of a nickel chelate compound as greenish brown crystals. The absorption λmax (in chloroform) of this compound was 578 nm ($\epsilon=14.4\times10^4$)

(b) Recording medium

In the same manner as in Example 16, a recording medium was prepared by using the nickel chelate compound obtained as described above. The absorption λmax of the coated film was 595 nm. The thickness of the recording layer was substantially the same as in Example 16.

(c) Optical recording method

Recording was carried out under the same recording conditions as in Example 16, whereby with a recording power of 5.8 mW, the Itop reflectance was 65%, and good recording characteristics were obtained with a degree of modulation of 60%.

EXAMPLES 19 TO 28

(Metal Chelate Compounds)

Figure 21:
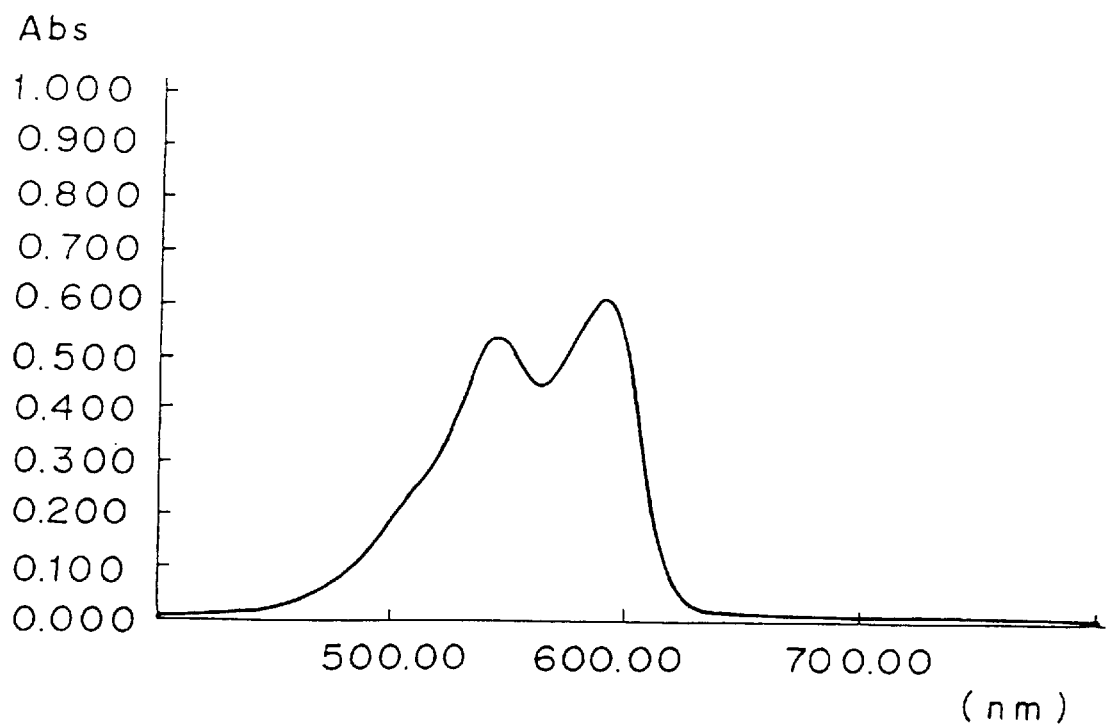
FIG. 21 is an absorption spectrum in a chloroform solution, of the metal chelate compound of Example 25.
Figure 22:
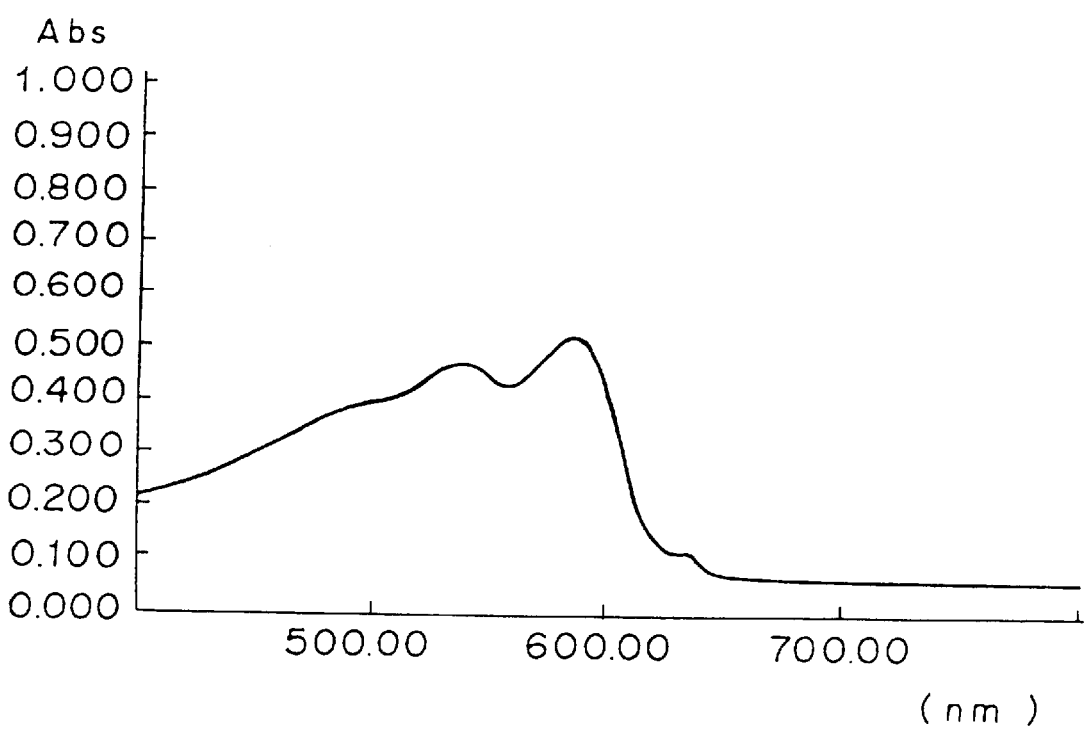
FIG. 22 is an absorption spectrum in a coating film, of the metal chelate compound of Example 25.

Examples 19 to 28 were carried out in the same manner as in Examples 16 to 18. λmax (in chloroform) of the solutions of the nickel chelate compounds of Examples 16 to 28 and λmax of the coated films are shown in Table 1. With respect to Examples 16 to 18, the absorption spectra in chloroform and the absorption spectra of the coated films are shown in FIGS. 13 to 18, respectively. Also with respect to Example 25, the absorption spectra are shown in FIGS. 21 and 22.

TABLE 1

| Example No. | Metal chelate compound | Solution λmax (nm) | Coated film λmax (nm) |
|---|---|---|---|
| 16 | {[3-methyl-1,2,4-thiadiazol-5-yl]–N=N–[4-(N,N-diethylamino)-2-(⁻NSO₂CH₂CF₃)phenyl]}₂Ni²⁺ | 582 | 601 |
| 17 | {[5-methylisoxazol-3-yl]–N=N–[2-methoxy-4-(N,N-diethylamino)-5-(⁻NSO₂CF₃)phenyl]}₂Ni²⁺ | 579 | 591 |
| 18 | {[1-butyl-4,5-dicyanoimidazol-2-yl]–N=N–[4-(N,N-diethylamino)-2-(⁻NSO₂CF₃)phenyl]}₂Ni²⁺ | 578 | 595 |
| 19 | {[1-butyl-5-ethoxycarbonyl-4-cyanoimidazol-2-yl]–N=N–[4-(N,N-diethylamino)-2-(⁻NSO₂CF₃)phenyl]}₂Ni²⁺ | 579 | 596 |
| 20 | {[3-propyl-1,2,4-thiadiazol-5-yl]–N=N–[4-(N,N-diethylamino)-2-(⁻NSO₂CF₃)phenyl]}₂Ni²⁺ | 585 | 605 |
| 21 | {[5-tert-butyl-1,3,4-thiadiazol-2-yl]–N=N–[4-(N,N-diethylamino)-2-(⁻NSO₂CF₃)phenyl]}₂Ni²⁺ | 583 | 601 |
| 22 | {[5-butyl-3-cyanopyrrol-2-yl]–N=N–[4-(N,N-diethylamino)-2-(⁻NSO₂CF₃)phenyl]}₂Ni²⁺ | 562 | 575 |

TABLE 1-continued

| Example No. | Metal chelate compound | Solution λmax (nm) | Coated film λmax (nm) |
|---|---|---|---|
| 23 | {thiazol-2-yl-N=N-C6H3(NSO2CF3⁻)-N(C2H5)2}2 Ni²⁺ | 580 | 611 |
| 24 | {1-CH3-5-(CH3S)-1,2,4-triazol-3-yl-N=N-C6H3(NSO2CF3⁻)-N(C2H5)2}2 Ni²⁺ | 561 | 572 |
| 25 | {5-Br-pyridin-2-yl-N=N-C6H3(NSO2CF3⁻)-N(C3H7(-iso))2}2 Ni²⁺ | 583 | 600 |
| 26 | {5-CF3-pyridin-2-yl-N=N-C6H3(NSO2CF3⁻)-N(C2H5)2}2 Ni²⁺ | 579 | 596 |
| 27 | {1-CH3-4,5-dicyano-imidazol-2-yl-N=N-C6H3(NSO2CF3⁻)-N(C2H5)2}2 Zn | 575 | 594 |
| 28 | {1-CH3-4,5-dicyano-imidazol-2-yl-N=N-C6H3(NSO2CF3⁻)-N(C2H5)2}2 Cu | 583 | 602 |

COMPARATIVE EXAMPLE 1

(a) Preparation example

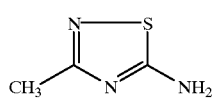

(32)

1.15 g of 2-amino-5-methyl-1,2,4-thiadiazole of the above structural formula (32) was dissolved in 10 ml of acetic acid and 5 ml of propionic acid. Then, 1 ml of sulfuric acid was dropwise added thereto at a temperature of from 0 to 5° C., and 3.55 g of 43% nitrosylsulfuric acid was added thereto at a temperature of from 0 to 5° C., for diazotization. The obtained diazotized solution was dropwise added at a temperature of from 0 to 5° C. to a solution having 3.24 g of 3-N,N-diethylpropanesulfonamide, 0.4 g of urea and 4.0 g of sodium acetate dissolved in 30 ml of methanol, and the mixture was stirred for 3 hours and then left to stand overnight. Precipitated crystals were collected by filtration and dried to obtain 1.13 g of red crystals of the following structural formula (33).

(33)

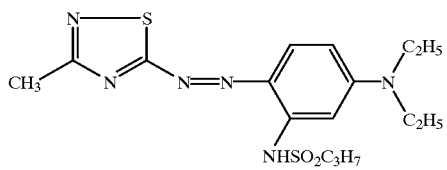

0.80 g of the azo compound of the structural formula (33) obtained as described above, was dissolved in 100 ml of methanol and 10 ml of THF. A solution having 0.60 g of nickel acetate tetrahydrate dissolved in 15 ml of methanol, was added thereto at room temperature, followed by stirring at room temperature for 3 hours. Then, 80 ml of water was added thereto. Precipitated crystals were collected by filtration, washed with water and dried to obtain 0.29 g of a nickel chelate compound as green crystals. The absorption λmax (in chloroform) of this compound was 552 nm ($\epsilon$=9.8× $10^4$).

(b) Recording medium

A recording medium was prepared in the same manner as in Example 16 using the nickel chelate compound obtained as described above. The absorption λmax of the coated film was 594 nm. The thickness of the recording layer was substantially the same as in Example 16.

(c) Optical recording method

Recording was carried out under the same conditions as in Example 16, whereby with a recording power of 5 mW, the degree of modulation was 60%, but the Itop reflectance was 40%, and thus the reflectance was not adequate.

Figure 19:
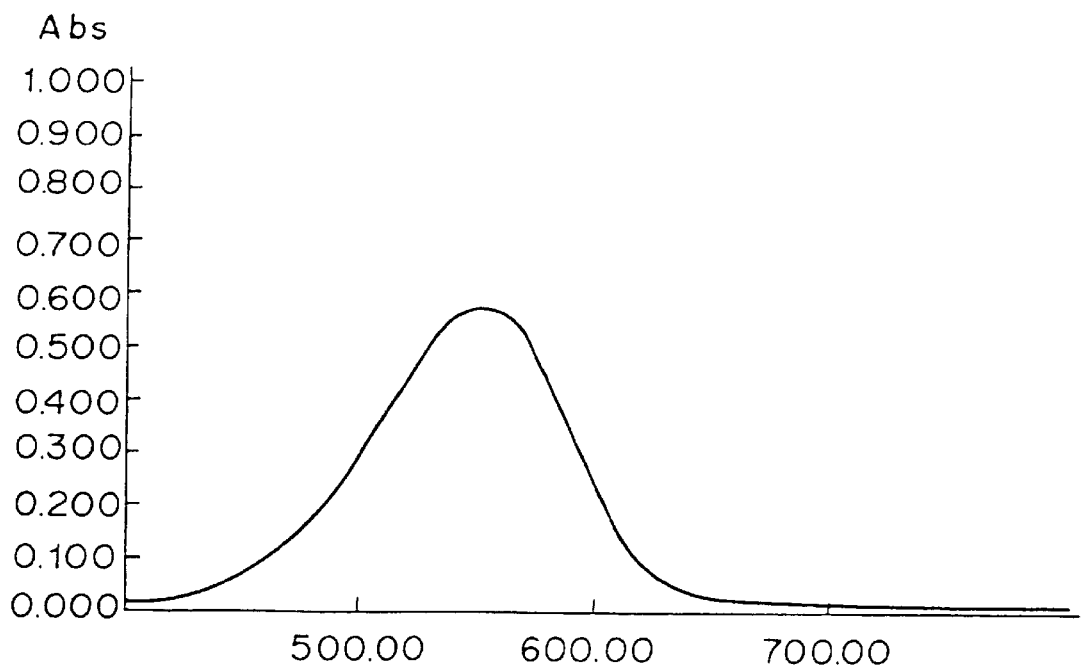
FIG. 19 is an absorption spectrum in a chloroform solution, of the metal chelate compound of Comparative Example 1.
Figure 20:
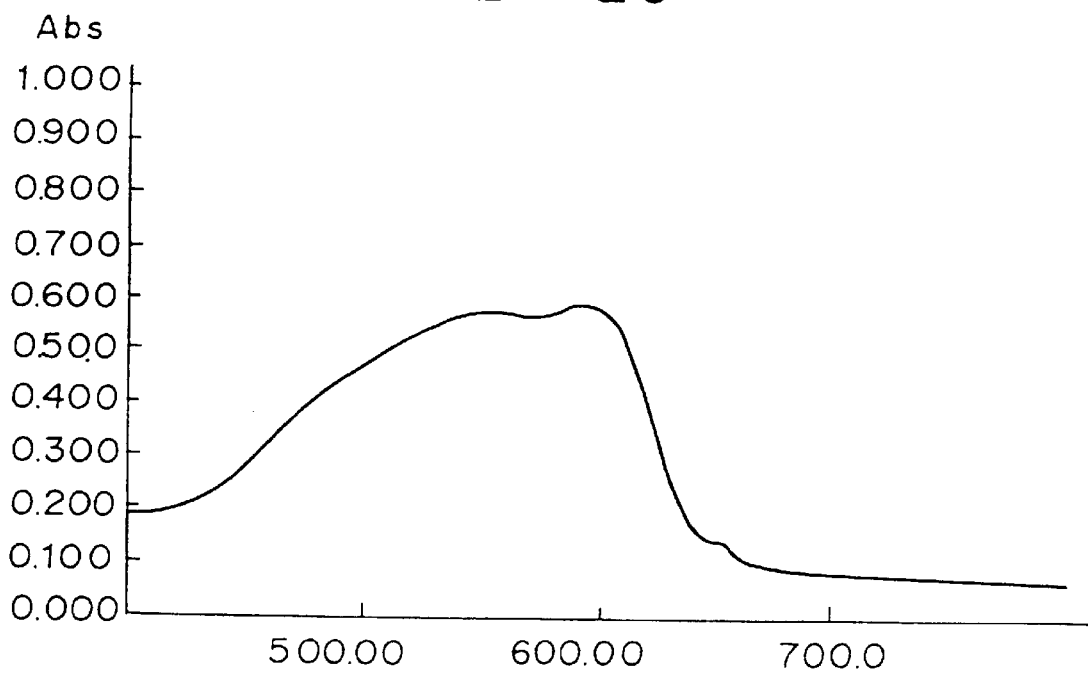
FIG. 20 is an absorption spectrum in a coating film, of the metal chelate compound of Comparative Example 1.

With respect to Comparative Example 1, the absorption spectrum in chloroform and the absorption spectrum of the coated film are shown in FIGS. 19 and 20, respectively.

With respect to recording media wherein the metal chelate compounds of Comparative Example 1 and Example 16 were respectively used, the light resistance and the storage stability were compared. Tests on light resistance (accelerated test by a xenon fade meter: 40 hours) and on storage stability (at 25° C. under a relative humidity of 85% for 200 hours) were carried out, whereupon the remaining ratio of the absorption peak. height at λmax was measured. The nickel chelate compound of Example 16 was found to be excellent in both light resistance and storage stability. The results are shown in Table 2.

EXAMPLE 29

(a) Preparation example 3.08 g of the azo compound of the structural formula (30) obtained in the same manner as in Example 18, and 0.96 g of potassium carbonate, were dissolved in 25 ml of DMF, and 1.31 g of ethyl iodide was dropwise added thereto. Then, the mixture was heated to 60° C. After stirring at 60° C. for 3 hours, the mixture was left to cool, and 10 ml of water was added thereto. Precipitated crystals were collected by filtration and dried to obtain 2.30 g of red crystals of the following structural formula (34).

(34)

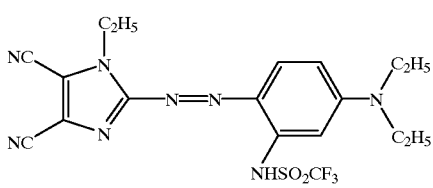

2.19 g of the azo compound of the structural formula (34) obtained as described above and 0.38 g of anhydrous sodium acetate was dissolved in 170 ml of THF and 85 ml of water. A solution having 0.70 g of nickel acetate tetrahydrate dissolved in 10 ml of methanol, was added thereto at room temperature, followed by stirring at room temperature for two hours. Then, 85 ml of water was added thereto. Precipitated crystals were collected by filtration, washed with water and dried to ob ain 1.86 g of a nickel chelate compound as deep green crystals. The absorption λmax (in chloroform) of this compound was 577 nm ($\epsilon$=15.9×$10^4$).

The mass spectrum was measured by a MALDI-TOF method, and the molecular weight 92.2 was confirmed.

(b) Recording medium

Figure 23:
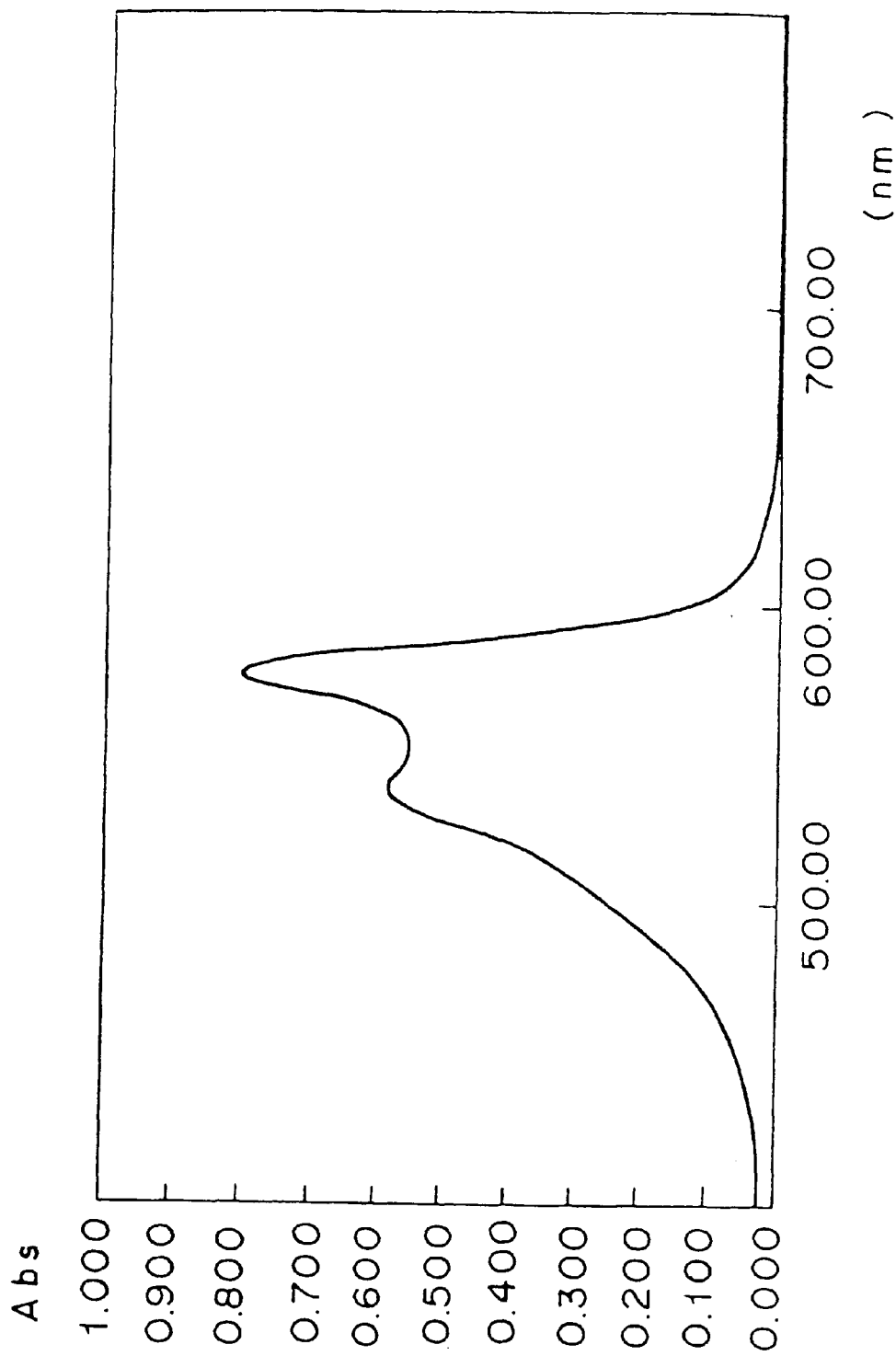
FIG. 23 is an absorption spectrum in a chloroform solution, of the metal chelate compound of Example 29.
Figure 24:
FIG. 24 is an absorption spectrum in a coating film, of the metal chelate compound of Example 29.
Figure 27:
FIG. 27 is a mass spectrum of the metal chelate compound of Example 29.

A recording medium was prepared in the same manner as in Example 16 using the nickel chelate compound obtained as described above. The absorption λmax of the coated film was 595 nm. The absorption spectra and the mass spectrum are shown in FIG. 23, 24 and 27. The thickness of the recording layer was substantially the same as in Example 16.

(c) Optical recording method

Recording was carried out under the same recording conditions as in Example 16, whereby with a recording

TABLE 2

| | Metal chelate compound | Light resistance | Storage stability |
|---|---|---|---|
| Comparative Example 1 | [structure with NSO$_2$C$_3$H$_7$, Ni$^{2+}$] | 86% | 88% |
| Example 16 | [structure with NSO$_2$CH$_2$CF$_3$, Ni$^{2+}$] | 96% | 99% | power of 5.3 mW, the $I_{top}$ reflectance was 60%, and good recording characteristics were obtained with a degree of modulation of 60%.

EXAMPLE 30

(a) Preparation example 3.08 g of the azo compound of the structural formula (30) obtained in the same manner as in Example 18, and 0.96 g of potassium carbonate, were dissolved in 70 ml of methanol. Then, 1.06 g of dimethyl sulfate was dropwise added thereto, and then the mixture was heated to 50° C. After stirring at 50° C. for 3 hours, the mixture was left to cool. Precipitated crystals were collected by filtration and dried to obtain 1.72 g of red crystals of the following structural formula (35).

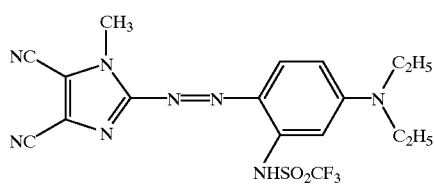

(35)

1.70 g of the azo compound of the structural formula (35) obtained as described above and 0.31 g of anhydrous sodium acetate were dissolved in 170 ml of THF and 85 ml of water. A solution having 0.56 g of nickel acetate tetrahydrate dissolved in 8 ml of methanol, was added thereto at room temperature, followed by stirring at room temperature for two hours. Then, 85 ml of water was added thereto. Precipitated crystals were collected by filtration, washed with water and dried to obtain 1.47 g of a nickel chelate compound as deep green crystals. The absorption λmax (in chloroform) of this compound was 577 nm ($\epsilon$=15.7×10$^4$).

(b) Recording medium

Figure 25:
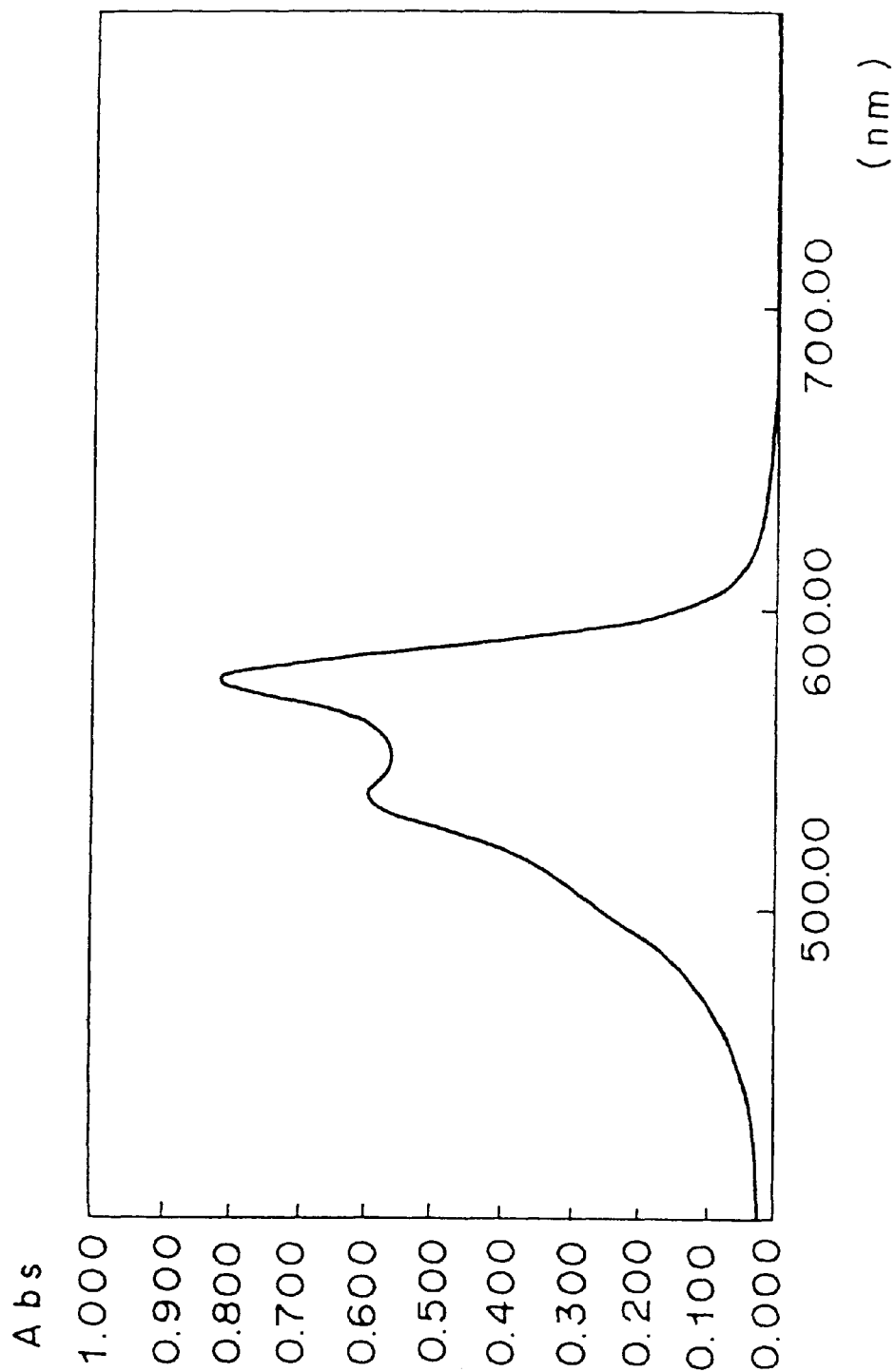
FIG. 25 is an absorption spectrum in a chloroform solution, of the metal chelate compound of Example 30.
Figure 26:
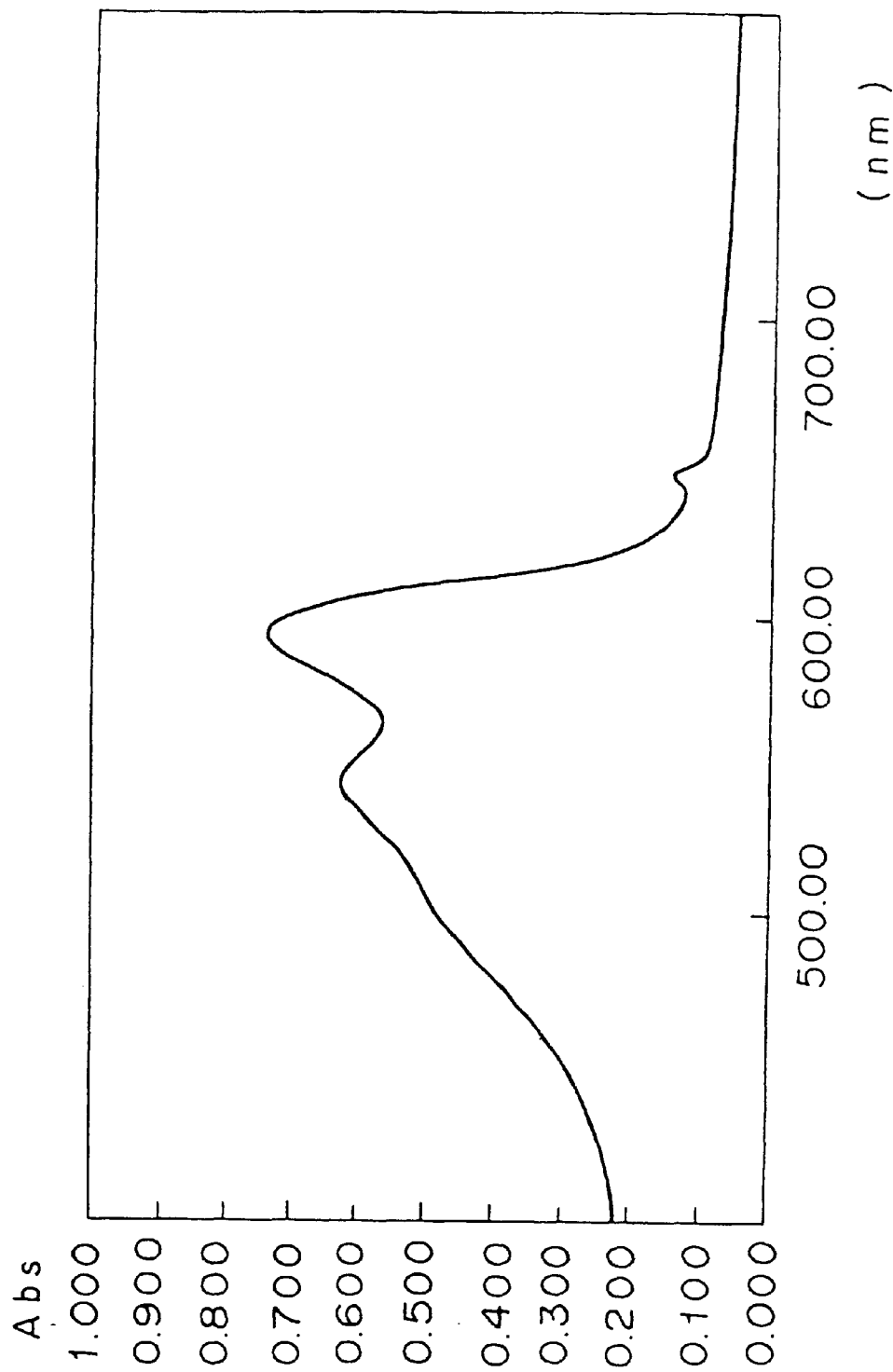
FIG. 26 is an absorption spectrum in a coating film, of the metal chelate compound of Example 30.

A recording medium was prepared in the same manner as in Example 1 using the nickel chelate compound obtained as described above. The absorption λmax of the coated film was 595 nm. The absorption spectra are shown in FIGS. 25 and 26. The thickness of the recording layer was substantially the same as in Example 16.

(c) Optical recording method

Recording was carried out under the same recording conditions as in Example 16, whereby with a recording power of 5.8 mW, the $I_{top}$ reflectance was 60%, and good recording characteristics were obtained with a degree of modulation of 60%.

Table 3

TABLE 3

| Example No. | Metal chelate compound | Solution λmax (nm) | Coated film λmax (nm) |
|---|---|---|---|
| 29 | ![structure] | 577 | 595 |
| 30 | ![structure] | 577 | 595 |

The metal chelate compounds of azo compounds with metals of the present invention respectively have absorptions within a range of from 600 to 700 nm, and they have good light resistance, storage stability and heat resistance and are very useful as absorbing materials for optical recording media, as described hereinafter.

Further, as their applications other than for optical recording media, various optical filters or colorants for plastics may be mentioned.

The optical recording medium of the present invention comprising the metal chelate compound of the azo compound with metal, is excellent in recording and retrieving characteristics with a laser beam of from 600 to 700 nm, whereby high reflectance and high density recording can be accomplished, and further, it is excellent in light resistance and durability.

EXAMPLE 31

(a) Preparation example

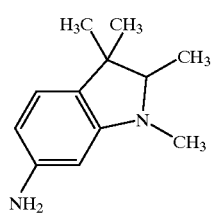

(36)

In a nitrogen stream, 7.90 g of trifluoromethane sulfonic anhydride was maintained at a temperature of not higher than 20° C. with stirring, and a solution having 3.81 g of a compound of the above formula (36) (which is obtained in accordance with such a method as described in U.S. Pat. No. 5,543,086) dissolved in 35 ml of toluene, was dropwise added thereto. Then, the mixture was stirred for two hours at a temperature of from 10 to 15° C. and left to stand overnight. 2 ml of water was added to the mixture at a temperature of from 10 to 25° C. and the mixture was stirred for one hour to precipitate a solid. The formed solid was collected by filtration, dissolved in acetone. To the resultant solution, was added 200 ml of water and extracted with ethyl acetate. The obtained extract was dried over anhydrous sodium sulfate, and then ethyl acetate was distilled off from the obtained extract. Thereafter, n-hexane was added to the extract to precipitate a crystal which was then collected by filtration. The crystal was dried to obtain 5.37 a of a brown crystal of the formula (37).

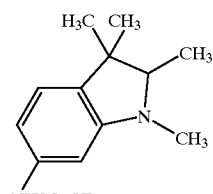

(37)

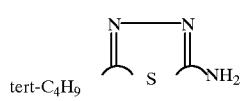

(38)

0.39 g of 2-amino-5-tert-butyl-1,3,4-thiadiazole of the above structural formula (38) was dissolved in 5 ml of acetic acid and 3 ml of propionic acid, and 1 ml of sulfuric acid was dropwise added thereto at a temperature of from 0 to 5° C., and 0.89 g of 43% nitrosylsulfuric acid was further added at a temperature of from 0 to 5° C. for diazotization. The obtained diazotized solution was dropwise added at a temperature of from 0 to 5° C. to a solution having 0.97 g of the above compound of the formula (37), 0.1 g of urea and 1.0 g of sodium acetate dissolved in 20 ml of methanol, and the mixture was stirred for 3 hours and then left to stand overnight to precipitate a crystal. The crystal was then collected by filtration and dried to obtain 0.69 g of a red crystal of the following structural formula (39).

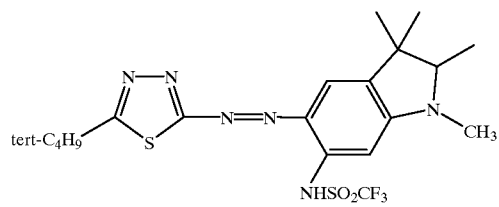

(39)

0.60 g of the azo compound of the structural formula (39) thus obtained was dissolved in 40 ml of tetrahydrofuran (THF) and a solution having 0.18 g of nickel acetate tetrahydrate dissolved in 3 ml of methanol, was added thereto at room temperature. Then, the mixture was stirred at room temperature for three hours, and 40 ml of water was added thereto to precipitate a crystal. The precipitated crystal was collected by filtration, washed with water and dried to obtain 0.29 g of a nickel chelate compound. The absorption λmax (in chloroform) of this compound was 589 nm ($\epsilon=9.5\times10^4$).

(b) Recording medium

A recording medium was prepared by using the above obtained nickel chelete compound in the same manner as in Example 16, except the nickel chelete compound was dissolved in octafluoropentanol to a concentration of 1.1 wt % and an Ag film having a thickness of 100 nm was coated to form a reflective layer. The absorption λmax of the coated film was 601 nm. The thickness of the recording layer was about 90 nm.

(c) Optical recording method

Recording was carried out under the same conditions as in Example 16, whereby with a recording power of 5.0 mW, the $I_{top}$ reflectance was 49%, and good recording characteristics were obtained with a degree of modulation of 60%.

What is claimed is:

1. An optical recording medium comprising a grooved transparent substrate and a recording layer capable of writing and/or reading out information by a light beam, formed on the substrate, wherein the recording layer contains a metal chelate compound obtained from an azo compound of the following formula (a) or (b) and a metal salt:

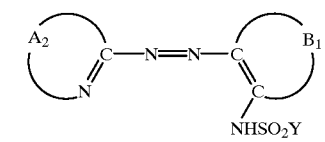

(a)

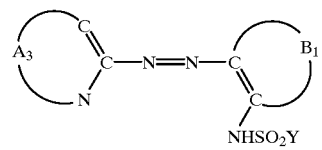

(b)

wherein each of $A_2$ and $A_3$ is a residue forming, together with the carbon atom and the nitrogen atom to which $A_2$ or $A_3$ is bonded, a heterocyclic ring which may have a substituent, $B_1$ is a residue forming, together with the carbon atoms to which $B_1$ is bonded, an aromatic or heterocyclic ring which may have a substituent, and Y is a $C_{1-6}$ linear or branched alkyl group substituted by at least two fluorine atoms.

2. The optical recording medium according to claim 1, wherein in the azo compound $A_2$ or $A_3$ is a residue forming, together with the carbon atom and the nitrogen atom to which $A_2$ or $A_3$ is bonded, a heterocyclic ring selected from the group consisting of thiadiazole, isoxazole, imidazole, pyrazole, thiazole, triazole and pyridine.

3. The optical recording medium according to claim 1, wherein the azo compound of the formula (I) is an azo compound of the following formula (II) or (III):

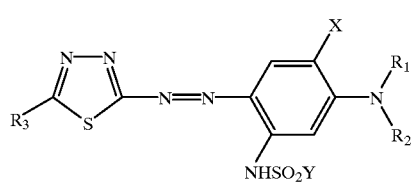

(II)

-continued (III)

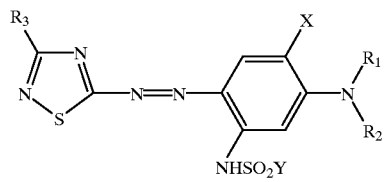

(VI)

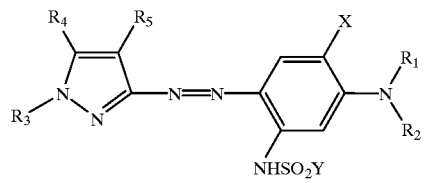

wherein X is a hydrogen atom, a methoxy group, an ethoxy group or a propoxy group, Y is a $C_{1-6}$ linear or branched alkyl group substituted by at least two fluorine atoms, and each of $R_1$, $R_2$ and $R_3$ is a $C_{1-6}$ linear or branched alkyl group which may be substituted.

4. The optical recording medium according to claim 1, wherein the azo compound of the formula (I) is an azo compound of the following formula (IV):

(IV)

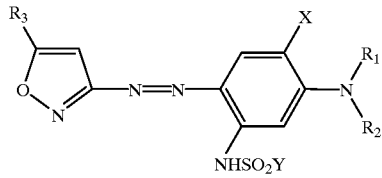

wherein X is a hydrogen atom, a methoxy group, an ethoxy group or a propoxy group, Y is a $C_{1-6}$ linear or branched alkyl group substituted by at least two fluorine atoms, and each of $R_1$, $R_2$ and $R_3$ is a $C_{1-6}$ linear or branched alkyl group which may be substituted.

5. The optical recording medium according to claim 1, wherein the azo compound of the formula (I) is an azo compound of the following formula (V):

(V)

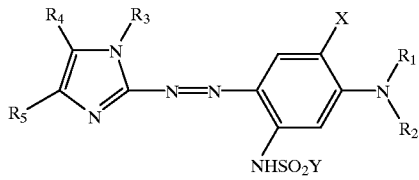

wherein X is a hydrogen atom, a methoxy group, an ethoxy group or a propoxy group, Y is a $C_{1-6}$ linear or branched alkyl group substituted by at least two fluorine atoms, each of $R_1$, $R_2$ and $R_3$ is a $C_{1-6}$ linear or branched alkyl group which may be substituted, and each of $R_4$ and $R_5$ is a $C_{1-6}$ linear or branched which may be substituted, a cyano group or a carboxylate group.

6. The optical recording medium according to claim 1, wherein the azo compound of the formula (I) is an azo compound of the following formula (VI):

wherein X is a hydrogen atom, a methoxy group, an ethoxy group or a propoxy group, Y is a $C_{1-6}$ linear or branched alkyl group substituted by at least two fluorine atoms, each of $R_1$, $R_2$ and $R_3$ is a $C_{1-6}$ linear or branched alkyl group which may be substituted, and each of R4 and R5 is a $C_{1-6}$ linear or branched which may be substituted, a cyano group or a carboxylate group.

7. The optical recording medium according to claim 1, wherein the azo compound of the formula (I) is an azo compound of the following formula (VII), (VIII) or (IX):

(VII)

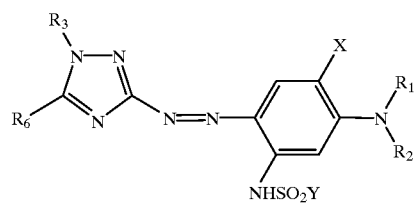

(VIII)

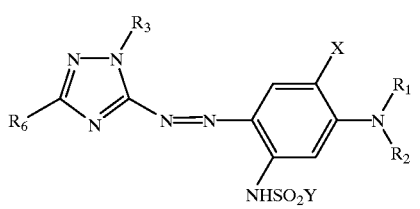

(IX)

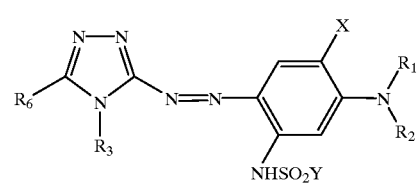

wherein X is a hydrogen atom, a methoxy group, an ethoxy group or a propoxy group, Y is a $C_{1-6}$ linear or branched alkyl group substituted by at least two fluorine atoms, each of $R_1$, $R_2$ and $R_3$ is a $C_{1-6}$ linear or branched alkyl group which may be substituted, and $R_6$ is a $C_{1-6}$ linear or branched alkyl group which may be substituted, an alkoxy group or an alkylthio group.

8. The optical recording medium according to claim 1, wherein the azo compound of the formula (I) is an azo compound of the following formula (X):

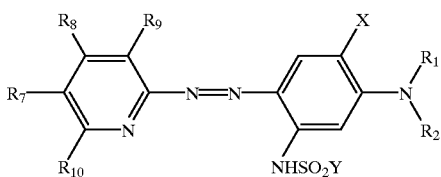

(X)

wherein X is a hydrogen atom, a methoxy group, an ethoxy group or a propoxy group, Y is a $C_{1-6}$ linear or branched alkyl group substituted by at least two fluorine atoms, each of $R_1$ and $R_2$ is a $C_{1-6}$ linear or branched alkyl group which may be substituted, and each of $R_7$ to $R_{10}$ is a $C_{1-6}$ linear or branched alkyl group which may be substituted, a hydrogen atom or a halogen atom.

9. The optical recording medium according to claim 1, wherein the metal is Ni, Co or Cu.

10. The optical recording medium according to claim 1, wherein a metal reflective layer and a protective layer are formed on the recording layer.

11. A process comprising retrieving a record by a laser beam having a center wavelength of from 600 to 700 nm from an optical recording medium according to claim 1.

12. An optical recording medium comprising a grooved transparent substrate and a recording layer capable of writing and/or reading out information by a light beam, formed on the substrate, wherein the recording layer contains a metal chelate compound obtained from an azo compound of the following formula (c) or (d) and a metal salt:

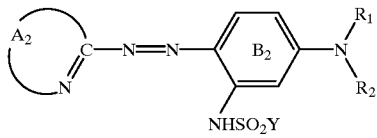

(c)

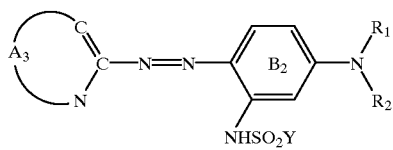

(d)

wherein each of $A_2$ and $A_3$ is a residue forming, together with the carbon atom or the nitrogen atom to which $A_2$ or $A_3$ is bonded, a heterocyclic ring which may have a substituent, $B_2$ is a benzene ring which may have a substituent, in addition to the —$NR_1R_2$ and the —$NHSO_2Y$ groups, Y is a $C_{1-6}$ linear or branched alkyl group substituted by at least two fluorine atoms, and each of $R_1$ and $R_2$ is independently an alkyl group which may have a substituent, or $R_1$ and $R_2$ together form a ring.

13. The optical recording medium according to claim 12, wherein the metal is Ni, Co or Cu.

14. A process comprising retrieving a record by a laser beam having a center wavelength of from 600 to 700 nm from an optical recording medium according to claim 12.

15. An optical recording medium comprising a grooved transparent substrate and a recording layer capable of writing and/or reading out information by a light beam, formed on the substrate, wherein the recording layer contains a metal chelate compound obtained from an azo compound of the following formula (I) and a metal salt:

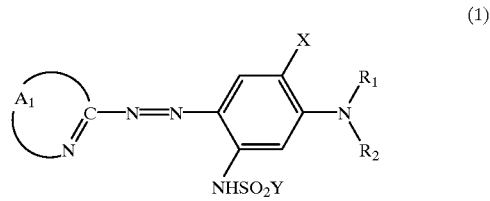

(1)

wherein $A_1$ or $A_2$ is a residue forming, together with the carbon atom and the nitrogen atom to which $A_1$ or $A_2$ is bonded, a 5- or 6-membered heterocyclic ring, X is a hydrogen atom, an alkyl group, an alkoxy group or a halogen atom, Y is a $C_{1-6}$ linear or branched alkyl group substituted by at least two fluorine atoms, and each of $R_1$ and $R_2$ which are independent of each other, is an alkyl group which may be substituted, or $R_1$ and $R_2$ together form a ring.

16. The optical recording medium according to claim 15, wherein the metal is Ni, Co or Cu.

17. A process comprising retrieving a record by a laser beam having a center wavelength of from 600 to 700 nm, from an optical recording medium according to claim 15.

* * * * *